United States Patent
Thompson et al.

(12) 
(10) Patent No.: US 6,503,901 B1
(45) Date of Patent: Jan. 7, 2003

(54) AMINO LACTAM SULFONAMIDES AS INHIBITORS OF Aβ PROTEIN PRODUCTION

(75) Inventors: Lorin Andrew Thompson, Wilmington, DE (US); Amy Qi Han, Hockessin, DE (US)

(73) Assignee: Bristol Myers Squibb Pharma Company

( * ) Notice: Subject to any disclaimer, the term of this patent is extended or adjusted under 35 U.S.C. 154(b) by 0 days.

(21) Appl. No.: 09/684,718

(22) Filed: Oct. 7, 2000

Related U.S. Application Data

(60) Provisional application No. 60/158,565, filed on Oct. 8, 1999.

(51) Int. Cl.[7] .................... C07D 413/12; C07D 409/12; C07D 401/12; A61K 31/55; A61P 25/28
(52) U.S. Cl. ....................................... 514/221; 540/509
(58) Field of Search .......................... 540/509; 514/221

(56) References Cited

U.S. PATENT DOCUMENTS

| | | | |
|---|---|---|---|
| 4,929,614 A | * 5/1990 | Calvet et al. ................ | 514/214 |
| 5,283,241 A | 2/1994 | Bochis et al. | |
| 5,389,631 A | 2/1995 | Claremon | |
| 5,532,359 A | 7/1996 | Marsters et al. | |
| 5,550,126 A | 8/1996 | Horwell et al. | |
| 5,578,629 A | 11/1996 | Ciccarone et al. | |
| 5,595,990 A | 1/1997 | Baldwin et al. | |
| 5,602,145 A | 2/1997 | Samanen | |
| 5,618,812 A | 4/1997 | Pineiro et al. | |
| 5,672,596 A | 9/1997 | Wyvratt et al. | |
| 5,710,153 A | 1/1998 | Ohmoto et al. | |
| 5,710,171 A | 1/1998 | Dinsmore et al. | |
| 5,756,528 A | 5/1998 | Anthony et al. | |
| 5,763,437 A | 6/1998 | Sato et al. | |
| 5,852,010 A | * 12/1998 | Graham et al. ............ | 514/221 |
| 5,856,326 A | 1/1999 | Anthony et al. | |
| 5,859,012 A | 1/1999 | Dinsmore et al. | |
| 5,869,682 A | 2/1999 | DeSolms | |
| 5,872,135 A | 2/1999 | DeSolms | |
| 5,885,995 A | 3/1999 | Dinsmore | |
| 5,891,889 A | 4/1999 | Anthony et al. | |
| 5,905,077 A | 5/1999 | Jungheim et al. | |
| 5,919,785 A | 7/1999 | Dinsmore et al. | |
| 5,936,089 A | 8/1999 | Carpino et al. | |
| 5,965,578 A | 10/1999 | Graham et al. | |

FOREIGN PATENT DOCUMENTS

| | | |
|---|---|---|
| DE | 2934355 | 3/1981 |
| EP | 0421802 | 4/1991 |
| EP | 0434360 | 6/1991 |
| EP | 0842944 | 5/1998 |
| WO | WO 9403437 | 2/1994 |
| WO | WO 9405634 | 3/1994 |
| WO | WO 9414776 | 7/1994 |
| WO | WO 9509633 | 4/1995 |
| WO | WO 9617833 | 6/1996 |
| WO | WO 9618602 | 6/1996 |
| WO | WO 9620918 | 7/1996 |
| WO | WO 9633165 | 10/1996 |
| WO | WO 9639137 | 12/1996 |
| WO | WO 9719053 | 5/1997 |
| WO | WO 9727852 | 8/1997 |
| WO | WO 9736877 | 10/1997 |
| WO | WO 9736879 | 10/1997 |
| WO | WO 9736900 | 10/1997 |
| WO | WO 9738664 | 10/1997 |
| WO | WO 9745412 | 12/1997 |
| WO | WO 9816523 | 4/1998 |
| WO | WO 9822430 | 5/1998 |
| WO | WO 9822433 | 5/1998 |
| WO | WO 9822441 | 5/1998 |
| WO | WO 9822493 | 5/1998 |
| WO | WO 9827053 | 6/1998 |
| WO | WO 9828268 | 7/1998 |
| WO | WO 9828980 | 7/1998 |
| WO | WO 9837079 | 8/1998 |
| WO | WO 9841510 | 9/1998 |
| WO | WO 9844797 | 10/1998 |
| WO | WO 9858915 | 12/1998 |
| WO | WO 9900654 | 1/1999 |
| WO | WO 9903826 | 1/1999 |
| WO | WO 9907730 | 2/1999 |
| WO | WO 9907731 | 2/1999 |
| WO | WO 9917777 | 4/1999 |
| WO | WO 9918951 | 4/1999 |
| WO | WO 9919305 | 4/1999 |
| WO | WO 9932453 | 7/1999 |
| WO | WO 9966934 | 12/1999 |
| WO | WO 9967219 | 12/1999 |
| WO | WO 9967220 | 12/1999 |
| WO | WO 9967221 | 12/1999 |
| WO | WO 0007995 | 2/2000 |
| WO | WO 0038618 | 7/2000 |

OTHER PUBLICATIONS

Dingwall; J. Clinical Invest., 108, Nov. 2001, 1243–1246.
Selkoe; J. Alzheimer's Disease, 3, 2001, p. 75–81.
Tanzi and Parson, "Decoding Darkness, The Search for the Genetic Causes of Alzheimer's Disease", Perseus Publishing, 2000, pp. xvii–xviii.
Olson et al., Current Opinion in Drug Discovery and Development, 4, 2001, p. 390–401.

* cited by examiner

Primary Examiner—Bruck Kifle

(57) ABSTRACT

This invention relates to novel lactams having the Formula (I):

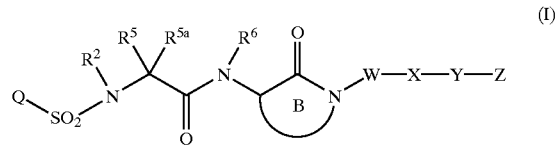

to their pharmaceutical compositions and to their methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

42 Claims, No Drawings

AMINO LACTAM SULFONAMIDES AS INHIBITORS OF Aβ PROTEIN PRODUCTION

This application claims the benefit of U.S. Provisional Application No. 60/158,565, filed Oct. 8, 1999.

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Dennis J. Selkoe; Cell Biology of the amyloid (beta)-protein precursor and the mechanism of Alzheimer's disease, Annu Rev Cell Biol, 1994, 10: 373–403).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885–890). The isolation and sequence data for the first 28 amino acids are described in U.S. Pat. No. 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, β secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or ysecretases could thereby reduce production of Aβ, which, thereby, could reduce or prevent the neurological disorders associated with Aβ protein.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

or pharmaceutically acceptable salt or prodrug forms thereof, wherein Q, $R^2$, $R^3$, $R^5$, $R^{5a}$, $R^6$, B, W, X, Y, and Z are defined below, are effective inhibitors of the production of Aβ.

DETAILED DESCRIPTION OF PREFERRED EMBODIMENTS

Thus, in one embodiment, the present invention provides a novel compound of Formula (I):

(I)

or a pharmaceutically acceptable salt or prodrug thereof, wherein:

Q is $C_1$–$C_6$ alkyl substituted with 0–3 $R^{1a}$;
  $C_2$–$C_6$ alkenyl substituted with 0–3 $R^{1a}$;
  $C_2$–$C_6$ alkynyl substituted with 0–3 $R^{1a}$;
  $C_3$–$C_{10}$ cycloalkyl substituted with 0–3 $R^{1b}$;
  $C_3$–$C_{10}$ carbocycle substituted with 0–3 $R^{1b}$;
  $C_6$–$C_{10}$ aryl substituted with 0–3 $R^{1b}$; or
  5 to 10 membered heterocycle substituted with 0–3 $R^{1b}$;

$R^{1a}$, at each occurrence, is independently selected from H, $R^{1b}$, Cl, F, Br, I, $OR^{14}$, CN, $NO_2$, =O, $NR^{19}R^{20}$, $CF_3$, $C_1$–$C_4$ alkyl; $C_2$–$C_4$ alkenyl; $C_2$–$C_4$ alkynyl; $C_1$–$C_4$ haloalkyl; $C_1$–$C_4$ haloalkoxy;
  $C_3$–$C_{10}$ carbocycle substituted with 0–3 $R^{1b}$;
  $C_6$–$C_{10}$ aryl substituted with 0–3 $R^{1b}$; and
  5 to 10 membered heterocycle substituted with 0–3 $R^{1b}$;

$R^{1b}$, at each occurrence, is independently selected from H, $OR^{14}$, Cl, F, Br, I, CN, $NO_2$, =O, $NR^{19}R^{20}$, $CF_3$, $C_1$–$C_4$ alkoxy, $C_1$–$C_4$ haloalkoxy;
  —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)NR$^{19b}$R$^{1d}$, —NR$^{19b}$C(=O)—$R^{1d}$, —NR$^{19b}$S(=O)$_2$—$R^{1d}$, —S(=O)$_2$NR$^{19b}$—$R^{1d}$, —NR$^{19b}$S(=O)—$R^{1d}$, —S(=O)NR$^{19b}$—$R^{1d}$, —C(=O)O—$R^{1d}$, —OC(=O)—$R^{1d}$;
  $C_1$–$C_6$ alkyl substituted with 0–3 $R^{1c}$;
  $C_2$–$C_6$ alkenyl substituted with 0–2 $R^{1c}$;
  $C_2$–$C_6$ alkynyl substituted with 0–2 $R^{1c}$;
  $C_3$–$C_{10}$ cycloalkyl substituted with 0–3 $R^{1f}$;
  $C_3$–$C_{10}$ carbocycle substituted with 0–3 $R^{1f}$;
  $C_6$–$C_{10}$ aryl substituted with 0–3 $R^{1f}$; and
  5 to 10 membered heterocycle substituted with 0–3 $R^{1f}$;

$R^{1c}$, at each occurrence, is independently selected from H, $OR^{14}$, Cl, F, Br, I, CN, $NO_2$, $NR^{19}R^{20}$, $CF_3$, $C_1$–$C_4$ alkoxy, $C_1$–$C_4$ haloalkoxy;
  —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)NR$^{19b}$R$^{1d}$, —NR$^{19b}$C(=O)—$R^{1d}$, —NR$^{19b}$S(=O)$_2$—$R^{1d}$, —S(=O)$_2$NR$^{19b}$—$R^{1d}$, —NR$^{19b}$S(=O)—$R^{1d}$, —S(=O)NR$^{19b}$—$R^{1d}$, —C(=O)O—$R^{1d}$, —OC(=O)—$R^{1d}$;
  $C_3$–$C_{10}$ cycloalkyl substituted with 0–3 $R^{1f}$;
  $C_3$–$C_{10}$ carbocycle substituted with 0–3 $R^{1f}$;
  $C_6$–$C_{10}$ aryl substituted with 0–3 $R^{1f}$; and
  5 to 10 membered heterocycle substituted with 0–3 $R^{1f}$;

$R^{1d}$, at each occurrence, is independently selected from H,
  $C_1$–$C_6$ alkyl substituted with 0–3 $R^{1e}$;
  $C_2$–$C_6$ alkenyl substituted with 0–2 $R^{1e}$;
  $C_2$–$C_6$ alkynyl substituted with 0–2 $R^{1e}$;
  $C_3$–$C_{10}$ cycloalkyl substituted with 0–3 $R^{1f}$;
  $C_3$–$C_{10}$ carbocycle substituted with 0–3 $R^{1f}$;
  $C_6$–$C_{10}$ aryl substituted with 0–3 $R^{1f}$;
  5 to 10 membered heterocycle substituted with 0–3 $R^{1f}$;

$R^{1e}$, at each occurrence, is independently selected from H, $OR^{14}$, Cl, F, Br, I, CN, $NO_2$, =O, $NR^{19}R^{20}$, $CF_3$, $C_1$–$C_4$ alkyl, $C_1$–$C_4$ haloalkyl, $C_1$–$C_4$ alkoxy, $C_1$–$C_4$ haloalkoxy;
  $C_3$–$C_{10}$ cycloalkyl substituted with 0–3 $R^{1f}$;
  $C_3$–$C_{10}$ carbocycle substituted with 0–3 $R^{1f}$;
  $C_6$–$C_{10}$ aryl substituted with 0–3 $R^{1f}$;
  5 to 10 membered heterocycle substituted with 0–3 $R^{1f}$;

$R^{1f}$, at each occurrence, is independently selected from H, $OR^{14}$, Cl, F, Br, I, CN, $NO_2$, =O, $NR^{19}R^{20}$, $CF_3$, $C_1$–$C_4$ alkyl, $C_1$–$C_4$ haloalkyl, $C_1$–$C_4$ alkoxy, and $C_1$–$C_4$ haloalkoxy;

$R^2$ is H, $C_1$–$C_6$ alkyl, ($C_1$–$C_6$ alkoxy) $C_1$–$C_3$ alkyl, $C_3$–$C_6$ carbocycle, $C_6$–$C_{10}$ aryl, ($C_3$–$C_6$ carbocycle)methyl, ($C_6$–$C_{10}$ aryl)methyl, ($C_6$–$C_{10}$ aryl)ethyl, or 5 to 10 membered heterocycle;

$R^5$ is H, OH, $OR^{14}$;
  $C_1$–$C_6$ alkyl substituted with 0–3 $R^{5b}$;
  $C_1$–$C_6$ alkoxy substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{10}$ cycloalkyl substituted with 0–3 $R^{5c}$;
  $C_3$–$C_{10}$ carbocycle substituted with 0–3 $R^{5c}$;
  $C_6$–$C_{10}$ aryl substituted with 0–3 $R^{5c}$; or
  5 to 10 membered heterocycle substituted with 0–3$R^{5c}$;

$R^{5a}$ is H, OH, $C_1$–$C_4$ alkyl, $C_1$–$C_4$ alkoxy, $C_2$–$C_4$ alkenyl, or $C_2$–$C_4$ alkenyloxy;

alternatively, $R^5$ and $R^{5a}$ may be combined to form =$R^5$;

alternatively, $R^5$ and $R^{5a}$ may be combined to form a 3–7 membered cycloalkyl ring substituted with 0–3 $R^{5c}$;
  optionally the cycloalkyl ring formed by combining $R^5$ and $R^{5a}$ may be benzo fused, wherein the benzo fused ring may be substituted with 0–3 $R^{5c}$;

$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$;
  $C_3$–$C_{10}$ cycloalkyl substituted with 0–3 $R^{5c}$;
  $C_3$–$C_{10}$ carbocycle substituted with 0–3 $R^{5c}$;
  $C_6$–$C_{10}$ aryl substituted with 0–3 $R^{5c}$; and
  5 to 10 membered heterocycle substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2$$CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkoxy;

$R^6$ is H;
  $C_1$–$C_6$ alkyl substituted with 0–3 $R^{6a}$;
  $C_3$–$C_{10}$ carbocycle substituted with 0–3 $R^{6b}$; or
  $C_6$–$C_{10}$ aryl substituted with 0–3 $R^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;

$R^{6b}$, at each occurrence, is independently selected from H, OH, Cl, F, Br, I, CN, NO$_2$, NR$^{15}$R$^{16}$, CF$_3$, C$_1$–C$_6$ alkyl, C$_1$–C$_4$ alkoxy, C$_1$–C$_4$ haloalkyl, and C$_1$–C$_4$ haloalkoxy;

Ring B is a 5 to 10 membered lactam,
  wherein the lactam is saturated, partially saturated or unsaturated;
  wherein each additional lactam carbon is substituted with 0–2 R$^{11}$; and,
  optionally, the lactam contains a heteroatom selected from —N—, —NH—, —N(R$^{10}$)—, —O—, —S—, —S(=O)—, and —S(=O)$_2$—;
additionally, two R$^{11}$ substituents on adjacent atoms may be combined to form C$_3$–C$_6$ carbocycle fused radical, a benzo fused radical, or a 5 to 6 membered heteroaryl fused radical,
  wherein said 5 to 6 membered heteroaryl fused radical comprises 1–2 heteroatoms selected from N, O, and S;
  wherein said benzo fused radical or 5 to 6 membered heteroaryl fused radical is substituted with 0–3 R$^{13}$;

$R^{10}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
  C$_1$–C$_6$ alkyl substituted with 0–2 R$^{10a}$;
  C$_6$–C$_{10}$ aryl substituted with 0–4 R$^{10b}$;
  C$_3$–C$_{10}$ carbocycle substituted with 0–3 R$^{10b}$; or
  5 to 10 membered heterocycle optionally substituted with 0–3 R$^{10b}$;

$R^{10a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or aryl substituted with 0–4 R$^{10b}$;

$R^{10b}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

$R^{11}$, at each occurrence, is independently selected from C$_1$–C$_4$ alkoxy, Cl, F, Br, I, =O, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
  C$_1$–C$_6$ alkyl substituted with 0–1 R$^{11a}$;
  C$_6$–C$_{10}$ aryl substituted with 0–3 R$^{11b}$;
  C$_3$–C$_{10}$ carbocycle substituted with 0–3 R$^{11b}$; or
  5 to 10 membered heterocycle substituted with 0–3 R$^{11b}$;

$R^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or phenyl substituted with 0–3 R$^{11b}$;

$R^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

W is —(CR$^8$R$^{8a}$)$_p$—;
p is 0, 1, 2, 3, or 4;
$R^8$ and $R^{8a}$, at each occurrence, are independently selected from H, F, C$_1$–C$_4$ alkyl, C$_2$–C$_4$ alkenyl, C$_2$–C$_4$ alkynyl and C$_3$–C$_8$ cycloalkyl;

X is a bond;
  C$_6$–C$_{10}$ aryl substituted with 0–3 R$^{Xb}$;
  C$_3$–C$_{10}$ cycloalkyl substituted with 0–3 R$_{Xb}$;
  C$_3$–C$_{10}$ carbocycle substituted with 0–3 R$^{Xb}$; or
  5 to 10 membered heterocycle substituted with 0–2 R$^{Xb}$;

$R^{Xb}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

Y is a bond or —(CR$^9$R$^{9a}$)$_t$—V—(CR$^9$R$^{9a}$)$_u$—;
t is 0, 1, 2, or 3;
u is 0, 1, 2, or 3;
$R^9$ and $R^{9a}$, at each occurrence, are independently selected from H, F, C$_1$–C$_6$ alkyl or C$_3$–C$_8$ cycloalkyl;

V is a bond, —C(=O)—, —O—, —S—, —S(=O)—, —S(=O)$_2$—, —N(R$^{19}$)—, —C(=O)NR$^{19b}$—, —NR$^{19b}$C(=O)—, —NR$^{19b}$S(=O)$_2$—, —S(=O)$_2$NR$^{19b}$—, —NR$^{19b}$S(=O)—, —S(=O)NR$^{19b}$—, —C(=O)O—, or —OC(=O)—;

Z is H;
  C$_1$–C$_8$ alkyl substituted with 0–2 R$^{12}$;
  C$_2$–C$_4$ alkenyl substituted with 0–2 R$^{12}$;
  C$_2$–C$_4$ alkynyl substituted with 0–2 R$^{12}$;
  C$_6$–C$_{10}$ aryl substituted with 0–4 R$^{12b}$;
  C$_3$–C$_{10}$ carbocycle substituted with 0–4 R$^{12b}$; or
  5 to 10 membered heterocycle substituted with 0–3 R$^{12b}$;

$R^{12}$ is C$_6$–C$_{10}$ aryl substituted with 0–4 R$^{12b}$; C$_3$–C$_{10}$ carbocycle substituted with 0–4 R$^{12b}$; or 5 to 10 membered heterocycle substituted with 0–3 R$_{12b}$;

$R^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ halothioalkoxy;

$R^{13}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, or CF$_3$;

$R^{14}$, at each occurrence, is independently selected from H, phenyl, benzyl, C$_1$–C$_6$ alkyl, or C$_2$–C$_6$ alkoxyalkyl;

$R^{15}$, at each occurrence, is independently selected from H, C$_1$–C$_6$ alkyl, benzyl, phenethyl, —C(=O)—(C$_1$–C$_6$ alkyl) and —S(=O)$_2$—(C$_1$–C$_6$ alkyl);

$R^{16}$, at each occurrence, is independently selected from H, OH, C$_1$–C$_6$ alkyl, benzyl, phenethyl, —C(=O)—(C$_1$–C$_6$ alkyl) and —S(=O)$_2$—(C$_1$–C$_6$ alkyl);

$R^{17}$ is H, aryl, aryl-CH$_2$—, C$_1$–C$_6$ alkyl, or C$_2$–C$_6$ alkoxyalkyl;

$R^{18}$, at each occurrence, is independently selected from H, C$_1$–C$_6$ alkyl, benzyl, phenethyl, —C(=O)—(C$_1$–C$_6$ alkyl) and —S(=O)$_2$—(C$_{1-6}$ alkyl);

$R^{19}$, at each occurrence, is independently selected from H, OH, C$_1$–C$_6$ alkyl, phenyl, benzyl, phenethyl, —C(=O)—(C$_1$–C$_6$ alkyl) and —S(=O)$_2$—(C$_1$–C$_6$ alkyl);

$R^{19b}$, at each occurrence, is independently selected from H, C$_1$–C$_4$ alkyl, phenyl, benzyl, and phenethyl; and $R^{20}$ and $R^{21}$, at each occurrence, are independently selected from H, C$_1$–C$_4$ alkyl, aryl, and aryl(C$_1$–C$_2$ alkyl)—.

[1] In another embodiment, the present invention provides a novel compound of Formula (I):

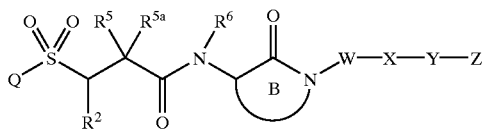
(I)

or a pharmaceutically acceptable salt or prodrug thereof, wherein:

Q is $C_1$–$C_6$ alkyl substituted with 0–3 $R^{1a}$;
$C_3$–$C_{10}$ cycloalkyl substituted with 0–3 $R^{1b}$;
$C_3$–$C_{10}$ carbocycle substituted with 0–3 $R^{1b}$;
$C_6$–$C_{10}$ aryl substituted with 0–3 $R^{1b}$; or
5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1a}$, at each occurrence, is independently selected from H, $R^{1b}$, Cl, F, Br, I, $OR^{14}$, CN, $NO_2$, =O, $NR^{19}R^{20}$, $CF_3$, $C_1$–$C_4$ alkyl; $C_2$–$C_4$ alkenyl; $C_2$–$C_4$ alkynyl; $C_1$–$C_4$ haloalkyl; $C_1$–$C_4$ haloalkoxy;
$C_3$–$C_{10}$ carbocycle substituted with 0–3 $R^{1b}$;
$C_6$–$C_{10}$ aryl substituted with 0–3 $R^{1b}$; and
5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1b}$, at each occurrence, is independently selected from H, $OR^{14}$, Cl, F, Br, I, CN, $NO_2$, =O, $NR^{19}R^{20}$, $CF_3$, $OCF_3$, $C_1$–$C_4$ alkoxy, $C_1$–$C_4$ haloalkoxy;
—C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2NR^{19b}$—$R^{1d}$, —$NR^{19b}$S(=O)—$R^{1d}$, —S(=O)$NR^{19b}$—$R^{1d}$, —C(=O)O—$R^{1d}$, —OC(=O)—$R^{1d}$;
$C_1$–$C_6$ alkyl substituted with 0–3 $R^{1c}$;
$C_2$–$C_6$ alkenyl substituted with 0–2 $R^{1c}$;
$C_2$–$C_6$ alkynyl substituted with 0–2 $R^{1c}$;
$C_3$–$C_{10}$ cycloalkyl substituted with 0–3 $R^{1f}$;
$C_3$–$C_{10}$ carbocycle substituted with 0–3 $R^{1f}$;
$C_6$–$C_{10}$ aryl substituted with 0–3 $R^{1f}$; and
5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, $OR^{14}$, Cl, F, Br, I, CN, $NO_2$, $NR^{19}R^{20}$, $CF_3$, $C_1$–$C_4$ alkoxy, $C_1$–$C_4$ haloalkoxy;
—C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2NR^{19b}$—$R^{1d}$, —$NR^{19b}$S(=O)—$R^{1d}$, —S(=O)$NR^{19b}$—$R^{1d}$, —C(=O)O—$R^{1d}$, —OC(=O)—$R^{1d}$;
$C_3$–$C_{10}$ cycloalkyl substituted with 0–3 $R^{1f}$;
$C_3$–$C_{10}$ carbocycle substituted with 0–3 $R^{1f}$;
$C_6$–$C_{10}$ aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1d}$, at each occurrence, is independently selected from H, $C_1$–$C_6$ alkyl substituted with 0–3 $R^{1e}$;
$C_2$–$C_6$ alkenyl substituted with 0–2 $R^{1e}$;
$C_2$–$C_6$ alkynyl substituted with 0–2 $R^{1e}$;
$C_3$–$C_{10}$ cycloalkyl substituted with 0–3 $R^{1f}$;
$C_3$–$C_{10}$ carbocycle substituted with 0–3 $R^{1f}$;
$C_6$–$C_{10}$ aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1e}$, at each occurrence, is independently selected from H, $OR^{14}$, Cl, F, Br, I, CN, $NO_2$, =O, $NR^{19}R^{20}$, $CF_3$, $C_1$–$C_4$ alkyl, $C_1$–$C_4$ haloalkyl, $C_1$–$C_4$ alkoxy, $C_1$–$C_4$ haloalkoxy;
$C_3$–$C_{10}$ cycloalkyl substituted with 0–3 $R^{1f}$;
$C_3$–$C_{10}$ carbocycle substituted with 0–3 $R^{1f}$;
$C_6$–$C_{10}$ aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1f}$, at each occurrence, is independently selected from H, $OR^{14}$, $SR^{14}$, Cl, F, Br, I, CN, $NO_2$, =O, $NR^{19}R^{20}$, $CF_3$, $C_1$–$C_4$ alkyl, $C_1$–$C_4$ haloalkyl, $C_1$–$C_4$ alkoxy, $C_1$–$C_4$ haloalkoxy, and $C_1$–$C_4$ haloalkyl-S—;

$R^2$ is H, $C_1$–$C_6$ alkyl, ($C_1$–$C_6$ alkoxy) $C_1$–$C_3$ alkyl, $C_3$–$C_6$ carbocycle, $C_6$–$C_{10}$ aryl, ($C_3$–$C_6$ carbocycle)methyl, ($C_6$–$C_{10}$ aryl)methyl, ($C_6$–$C_{10}$ aryl)ethyl, or 5 to 10 membered heterocycle;

$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ cycloalkyl substituted with 0–3 $R^{5c}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H or $C_1$–$C_4$ alkyl;

$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$; acetyl, —S($C_1$–$C_4$ alkyl), —S(=O)($C_1$–$C_4$ alkyl), —S(=O)$_2$($C_1$–$C_4$ alkyl);
$C_3$–$C_{10}$ cycloalkyl substituted with 0–3 $R^{5c}$;
$C_3$–$C_{10}$ carbocycle substituted with 0–3 $R^{5c}$;
$C_6$–$C_{10}$ aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3 $R^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;

$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;

Ring B is a 6, 7, or 8 membered lactam,
  wherein the lactam is saturated, partially saturated or unsaturated;
  wherein each additional lactam carbon is substituted with 0–2 $R^{11}$; and,
  optionally, the lactam contains a heteroatom selected from —N=, —NH—, —N($R^{10}$)—, —O—, —S—, —S(=O)—, and
additionally, two $R^{11}$ substituents on adjacent atoms may be combined to form $C_3$–$C_6$ carbocycle fused radical, a benzo fused radical, or a 5 to 6 membered heteroaryl fused radical,
  wherein said 5 to 6 membered heteroaryl fused radical comprises 1–2 heteroatoms selected from N, O, and S;
  wherein said benzo fused radical or 5 to 6 membered heteroaryl fused radical is substituted with 0–3 $R^{13}$;
$R^{10}$ is H, C(=O)$R^{17}$, C(=O)—$R^{17}$, C(=O)N$R^{18}R^{19}$, S(=O)$_2$N$R^{18}R^{19}$, S(=O)$_2R^{17}$;
  $C_1$–$C_6$ alkyl substituted with 0–2 $R^{10a}$;
  $C_6$–$C_{11}$ aryl substituted with 0–4 $R^{10b}$;
  $C_3$–$C_{10}$ carbocycle substituted with 0–3 $R^{10b}$; or
  5 to 10 membered heterocycle containing 1 to 4 heteroatoms selected from nitrogen, oxygen, and sulphur, wherein said 5 to 10 membered heterocycle is substituted with 0–3 $R^{10b}$;
$R^{10a}$, at each occurrence, is independently selected from H, $C_1$–$C_6$ alkyl, O$R^{14}$, Cl, F, Br, I, =O, CN, NO$_2$, N$R^{15}R^{16}$, CF$_3$, or aryl substituted with 0–4 $R^{10b}$;
$R^{10b}$, at each occurrence, is independently selected from H, OH, $C_1$–$C_6$ alkyl, $C_1$–$C_4$ alkoxy, Cl, F, Br, I, CN, NO$_2$, N$R^{15}R^{16}$, CF$_3$, acetyl, SCH$_3$, S(=O)CH$_3$, S(=O)$_2$CH3, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{11}$, at each occurrence, is independently selected from H, $C_1$–$C_4$ alkoxy, Cl, F, Br, I, =O, CN, NO$_2$, N$R^{18}R^{19}$, C(=O)$R^{17}$, C(=O)O$R^{17}$, C(=O)N$R^{18}R^{19}$, S(=O)$_2$N$R^{18}R^{19}$, CF$_3$;
  $C_1$–$C_6$ alkyl substituted with 0–1 $R^{11a}$;
  $C_6$–$C_{10}$ aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, O$R^{14}$, Cl, F, Br, I, =O, CN, NO$_2$, N$R^{15}R^{16}$, CF$_3$, or phenyl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
W is —(C$R^8R^{8a}$)$_p$—;
p is 0, 1, 2, 3, or 4;
$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;
X is a bond;
  $C_6$–$C_{10}$ aryl substituted with 0–3 $R^{Xb}$;
  $C_3$–$C_{10}$ cycloalkyl substituted with 0–3 $R^{Xb}$;
  $C_3$–$C_{10}$ carbocycle substituted with 0–3 $R^{Xb}$; or
  5 to 10 membered heterocycle containing 1 to 4 heteroatoms selected from nitrogen, oxygen, and sulphur, wherein said 5 to 10 membered heterocycle is substituted with 0–3 $R^{Xb}$;
$R^{Xb}$ at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
Y is a bond or —(C$R^9R^{9a}$)$_t$—V—(C$R^9R^{9a}$)$_u$—;
t is 0, 1, 2, or 3;
u is 0, 1, 2, or 3;
$R^9$ and $R^{9a}$, at each occurrence, are independently selected from H, F, $C_1$–$C_6$ alkyl or $C_3$–$C_8$ cycloalkyl;
V is a bond, —C(=O)—, —O—, —S—, —S(=O)—, —S(=O)$_2$—, —N($R^{19}$)—, —C(=O)N$R^{19b}$—, —N$R^{19b}$C(=O)—, —N$R^{19b}$S(=O)$_2$—, —S(=O)$_2$N$R^{19b}$—, —N$R^{19b}$S(=O)—, —S(=O)N$R^{19b}$—, —C(=O)O—, or —OC(=O)—;
Z is H;
  $C_1$–$C_8$ alkyl substituted with 0–2 $R^{12}$;
  $C_2$–$C_6$ alkenyl substituted with 0–2 $R^{12}$;
  $C_2$–$C_6$ alkynyl substituted with 0–2 $R^{12}$;
  $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12}$ is $C_6$–$C_{10}$ aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12b}$, at each occurrence, is independently selected from H, OH, Cl, F, Br, I, CN, NO$_2$, N$R^{15}R^{16}$, CF$_3$, acetyl, SCH$_3$, S(=O)CH3, S(=O)$_2$CH$_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{13}$, at each occurrence, is independently selected from H, OH, $C_1$–$C_6$ alkyl, $C_1$–$C_4$ alkoxy, Cl, F, Br, I, CN, NO$_2$, N$R^{15}R^{16}$, or CF$_3$;
$R^{14}$, at each occurrence, is independently selected from H, phenyl, benzyl, $C_1$–$C_6$ alkyl, or $C_2$–$C_6$ alkoxyalkyl;
$R^{15}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_1$–$C_6$ alkyl);
$R^{16}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl);
alternatively, —N$R^{15}R^{16}$ may be a heterocyclic ring selected from the group piperidinyl, morpholinyl, thiomorpholinyl, pyrrolidinyl, homopiperidinyl, piperazinyl, and N-methylpiperizinyl;
$R^{17}$ is H, aryl, aryl-CH$_2$—, $C_1$–$C_6$ alkyl, or $C_2$–$C_6$ alkoxyalkyl;
$R^{18}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19b}$, at each occurrence, is independently selected from H, $C_1$–$C_4$ alkyl, phenyl, benzyl, and phenethyl; and $R^{20}$ and $R^{21}$, at each occurrence, are independently selected from H, $C_1$–$C_4$ alkyl, aryl, and aryl($C_1$–$C_2$ alkyl)—;

provided that when Q is phenyl, 3-F-phenyl, benzyl, propyl, or octyl; $R^2$ is H; $R^5$ is methyl, and —WXYZ is methyl, then Ring B is not

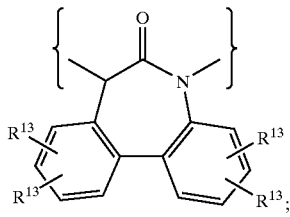

wherein $R^{13}$ is H.

[2] In an alternative embodiment of the present invention of of Formula (I),

Q is $C_1$–$C_6$ alkyl substituted with 0–3 $R^{1a}$;
  $C_3$–$C_{10}$ cycloalkyl substituted with 0–3 $R^{1b}$;
  $C_3$–$C_{10}$ carbocycle substituted with 0–3 $R^{1b}$;
  $C_6$–$C_{10}$ aryl substituted with 0–3 $R^{1b}$; or
  5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1a}$, at each occurrence, is independently selected from H, $R^{1b}$, Cl, F, Br, $NR^{19}R^{20}$, $CF_3$, $C_1$–$C_4$ alkyl, $C_1$–$C_4$ haloalkyl;
  $C_3$–$C_{10}$ carbocycle substituted with 0–3 $R^{1b}$;
  $C_6$–$C_{10}$ aryl substituted with 0–3 $R^{1b}$; and
  5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1b}$, at each occurrence, is independently selected from H, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy;
  —C(=O)—$R^{1d}$, $OR^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2NR^{19b}$—$R^{1d}$, —$NR^{19b}$S(=O)—$R^{1d}$, —S(=O)$NR^{19b}$—$R^{1d}$, —C(=O)O—$R^{1d}$, —OC(=O)—$R^{1d}$;
  $C_1$–$C_6$ alkyl substituted with 0–3 $R^{1c}$;
  $C_3$–$C_{10}$ cycloalkyl substituted with 0–3 $R^{1f}$;
  $C_6$–$C_{10}$ aryl substituted with 0–3 $R^{1f}$; and
  5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, $OR^{14}$, Cl, F, Br, $NO_2$, $NR^{19}R^{20}$, $CF_3$, $C_1$–$C_4$ alkoxy, $C_1$–$C_4$ haloalkoxy; —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2NR^{19b}$—$R^{1d}$, —$NR^{19b}$S(=O)—$R^{1d}$, —S(=O)$NR^{19b}$—$R^{1d}$, —C(=O)O$R^{1d}$, —OC(=O)—$R^{1d}$;

$C_3$–$C_{10}$ cycloalkyl substituted with 0–3 $R^{1f}$;
  $C_3$–$C_{10}$ carbocycle substituted with 0–3 $R^{1f}$;
  $C_6$–$C_{10}$ aryl substituted with 0–3 $R^{1f}$; and
  5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1d}$, at each occurrence, is independently selected from H, $C_1$–$C_6$ alkyl, and $C_6$–$C_{10}$ aryl substituted with 0–3 $R^{1f}$;

$R^{1f}$, at each occurrence, is independently selected from H, $OR^{14}$, $SR^{14}$, Cl, F, Br, I, CN, $NO_2$, =O, $NR^{19}R^{20}$, $CF_3$, $C_1$–$C_4$ alkyl, $C_1$–$C_4$ haloalkyl, $C_1$–$C_4$ alkoxy, $C_1$–$C_4$ haloalkoxy, and $C_1$–$C_4$ haloalkyl-S—;

$R^2$ is H or $C_1$–$C_6$ alkyl;

$R^5$ is H, $OR^{14}$;
  $C_1$–$C_6$ alkyl substituted with 0–3 $R^{5b}$;
  $C_1$–$C_6$ alkoxy substituted with 0–3 $R^{5b}$;
  $C_2$–$C_6$ alkenyl substituted with 0–3 $R^{5b}$; or
  $C_2$–$C_6$ alkynyl substituted with 0–3 $R^{5b}$;

$R^{5a}$ is H or $C_1$–$C_4$ alkyl;

$R^{5b}$, at each occurrence, is independently selected from: H, $C_1$–$C_6$ alkyl, $CF_3$, $OR^{14}$, Cl, F, Br, I, =O, CN, $NO_2$, $NR^{15}R^{16}$; acetyl, $S(C_1$–$C_4$ alkyl), S(=O)($C_1$–$C_4$ alkyl), S(=O)$_2$($C_1$–$C_4$ alkyl),
  $C_3$–$C_{10}$ cycloalkyl substituted with 0–3 $R^{5c}$;
  $C_3$–$C_{10}$ carbocycle substituted with 0–3 $R^{5c}$;
  $C_6$–$C_{10}$ aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H, methyl, or ethyl;

Ring B is a seven membered lactam,
  wherein the lactam is saturated, partially saturated or unsaturated;
  wherein each additional lactam carbon is substituted with 0–2 $R^{11}$; and,
  optionally, the lactam contains a heteroatom selected from —N=, —NH—, —N($R^{10}$)—, —O—, —S—, —S(=O)—, and —S(=O)$_2$—;

additionally, two $R^{11}$ substituents on adjacent atoms may be combined to form $C_3$–$C_6$ carbocycle fused radical, a benzo fused radical, or a 5 to 6 membered heteroaryl fused radical,
  wherein said 5 to 6 membered heteroaryl fused radical comprises 1–2 heteroatoms selected from N, O, and S;
  wherein said benzo fused radical or 5 to 6 membered heteroaryl fused radical is substituted with 0–3 $R^{13}$;

$R^{10}$ is H, C(=O)$R^{17}$, C(=O)$OR^{17}$, C(=O)$NR^{18}R^{19}$, S(=O)$_2NR^{18}R^{19}$, S(=O)$_2R^{17}$;
  $C_1$–$C_6$ alkyl substituted with 0–2 $R^{10a}$;
  $C_6$–$C_{10}$ aryl substituted with 0–4 $R^{10b}$;
  $C_3$–$C_{10}$ carbocycle substituted with 0–3 $R^{10b}$; or
  5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or aryl substituted with 0–4 $R^{10b}$;

$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, $CF_3$, acetyl, $SCH_3$, $S(=O)CH3$, $S(=O)_2CH3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl substituted with 0–1 $R^{11a}$;
$C_6$–$C_{10}$ aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is —$(CR^8R^{8a})_p$—;
p is 0, 1, or 2;
$R^8$ and $R^{8a}$, at each occurrence, are independently selected from H, F, methyl, and ethyl;
X is a bond;
phenyl substituted with 0–3 $R^{Xb}$;
$C_3$–$C_6$ cycloalkyl substituted with 0–3 $R^{Xb}$; or
5 to 6 membered heterocycle containing 1 to 4 heteroatoms selected from nitrogen, oxygen, and sulphur, wherein said 5 to 6 membered heterocycle is substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond or —$(CR^9R^{9a})_t$—V—$(CR^9R^{9a})_u$—;
t is 0, 1, or 2;
u is 0, 1, or 2;
$R^9$ and $R^{9a}$, at each occurrence, are independently selected from H, F, methyl, and ethyl;
V is a bond, —C(=O)—, —O—, —S—, —S(=O)—, —S(=O)_2—, —N($R^{19}$)—, —NHC(=O)—, or —C(=O)NH—;
Z is H;
$C_1$–$C_6$ alkyl substituted with 0–2 $R^{12}$;
$C_2$–$C_6$ alkenyl substituted with 0–2 $R^{12}$;
$C_2$–$C_6$ alkynyl substituted with 0–2 $R^{12}$;
phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_4$ alkyl, $C_1$–$C_4$ alkoxy, Cl, F, Br, I, CN, $NO_2$, $NR^{15}R^{16}$, and $CF_3$;

$R^{14}$, at each occurrence, is independently selected from H, phenyl, benzyl, $C_1$–$C_6$ alkyl, and $C_2$–$C_6$ alkoxyalkyl;

$R^{15}$, at each occurrence, is independently selected from H, $C_1$–$C_6$ alkyl, phenyl, benzyl, phenethyl, —C(=O)—($C_1$–$C_6$ alkyl) and —S(=O)_2—($C_1$–$C_6$ alkyl);

$R^{16}$, at each occurrence, is independently selected from H, OH, $C_1$–$C_6$ alkyl, phenyl, benzyl, phenethyl, —C(=O)—($C_1$–$C_6$ alkyl) and —S(=O)_2—($C_1$–$C_6$ alkyl);

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperizinyl;

$R^{17}$ is H, aryl, aryl-$CH_2$—, $C_1$–$C_6$ alkyl, or $C_2$–$C_6$ alkoxyalkyl;

$R^{18}$, at each occurrence, is independently selected from H, $C_1$–$C_6$ alkyl, phenyl, benzyl, phenethyl, —C(=O)—($C_1$–$C_6$ alkyl) and —S(=O)_2—($C_1$–$C_6$ alkyl);

$R^{19}$, at each occurrence, is independently selected from H, OH, $C_1$–$C_6$ alkyl, phenyl, benzyl, phenethyl, —C(=O)—($C_1$–$C_6$ alkyl) and —S(=O)_2—($C_1$–$C_6$ alkyl); and $R^{20}$ is H or $C_1$–$C_4$;

provided that when Q is phenyl, 3-F-phenyl, benzyl, propyl, or octyl; $R^2$ is H; $R^5$ is methyl, and —WXYZ is methyl, then Ring B is not

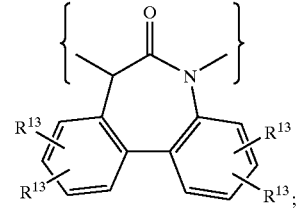

wherein $R^{13}$ is H.

[3] In another alterantive embodiment of the present invention of of Formula (I), Ring B is selected from:

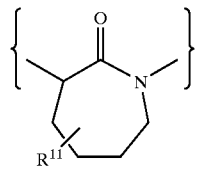 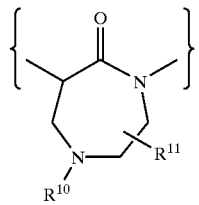

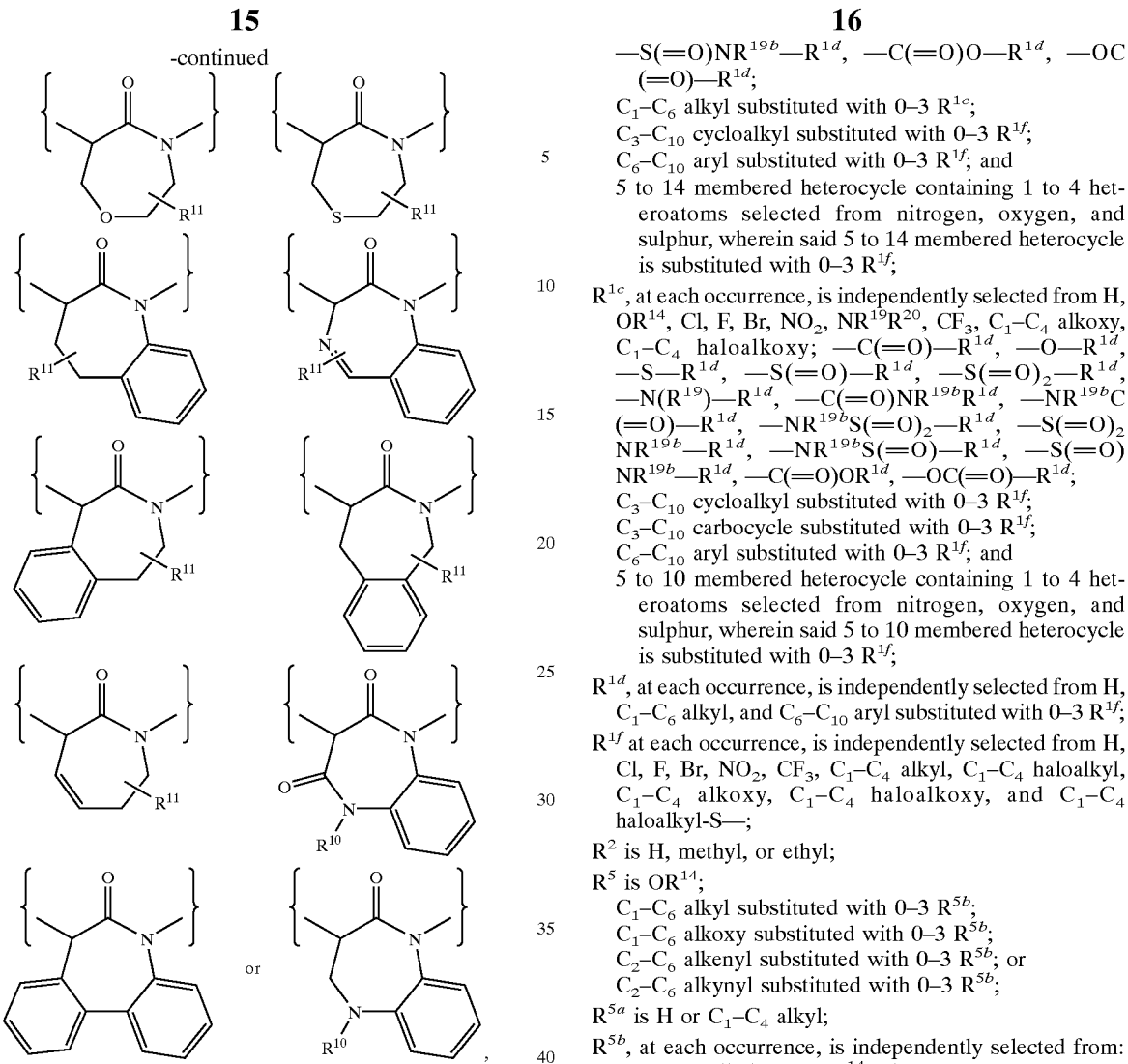

wherein each benzo fused radical is substituted with 0–3 $R^{13}$.

[4] In another alternative embodiment of the present invention of of Formula (I), Q is $C_1$–$C_6$ alkyl substituted with 0–3 $R^{1a}$;
  $C_3$–$C_{10}$ cycloalkyl substituted with 0–3 $R^{1b}$;
  $C_6$–$C_{10}$ aryl substituted with 0–3 $R^{1b}$; or
  5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1a}$, at each occurrence, is independently selected from H, Cl, F, Br, $NR^{19}R^{20}$, $CF_3$, $C_1$–$C_4$ alkyl; $C_1$–$C_4$ haloalkyl;
  $C_6$–$C_{10}$ aryl substituted with 0–3 $R^{1b}$; and
  5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1b}$, at each occurrence, is independently selected from H, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy;
  —C(=O) $R^{1d}$, —O—$R^{1d}$, —S—$R^{1d}$, —S(=O)—$R^{1d}$, —S(=O)$_2$—$R^{1d}$,
  —N($R^{19}$)—$R^{1d}$, —C(=O)$NR^{19b}R^{1d}$, —$NR^{19b}$C(=O)—$R^{1d}$,
  $NR^{19b}$S(=O)$_2$—$R^{1d}$, —S(=O)$_2NR^{19b}$—$R^{1d}$, —$NR^{19b}$S(=O)—$R^{1d}$,
  —S(=O)$NR^{19b}$—$R^{1d}$, —C(=O)O—$R^{1d}$, —OC(=O)—$R^{1d}$;

$C_1$–$C_6$ alkyl substituted with 0–3 $R^{1c}$;
$C_3$–$C_{10}$ cycloalkyl substituted with 0–3 $R^{1f}$;
$C_6$–$C_{10}$ aryl substituted with 0–3 $R^{1f}$; and
5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, $OR^{14}$, Cl, F, Br, $NO_2$, $NR^{19}R^{20}$, $CF_3$, $C_1$–$C_4$ alkoxy, $C_1$–$C_4$ haloalkoxy; —C(=O)—$R^{1d}$, —O—$R^{1d}$,
  —S—$R^{1d}$, —S(=O)—$R^{1d}$, —S(=O)$_2$—$R^{1d}$,
  —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2$$NR^{19b}$—$R^{1d}$, —$NR^{19b}$S(=O)—$R^{1d}$, —S(=O)$NR^{19b}$—$R^{1d}$, —C(=O)$OR^{1d}$, —OC(=O)—$R^{1d}$;
$C_3$–$C_{10}$ cycloalkyl substituted with 0–3 $R^{1f}$;
$C_3$–$C_{10}$ carbocycle substituted with 0–3 $R^{1f}$;
$C_6$–$C_{10}$ aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1d}$, at each occurrence, is independently selected from H, $C_1$–$C_6$ alkyl, and $C_6$–$C_{10}$ aryl substituted with 0–3 $R^{1f}$;

$R^{1f}$ at each occurrence, is independently selected from H, Cl, F, Br, $NO_2$, $CF_3$, $C_1$–$C_4$ alkyl, $C_1$–$C_4$ haloalkyl, $C_1$–$C_4$ alkoxy, $C_1$–$C_4$ haloalkoxy, and $C_1$–$C_4$ haloalkyl-S—;

$R^2$ is H, methyl, or ethyl;

$R^5$ is $OR^{14}$;
  $C_1$–$C_6$ alkyl substituted with 0–3 $R^{5b}$;
  $C_1$–$C_6$ alkoxy substituted with 0–3 $R^{5b}$;
  $C_2$–$C_6$ alkenyl substituted with 0–3 $R^{5b}$; or
  $C_2$–$C_6$ alkynyl substituted with 0–3 $R^{5b}$;

$R^{5a}$ is H or $C_1$–$C_4$ alkyl;

$R^{5b}$, at each occurrence, is independently selected from:
  H, $C_1$–$C_6$ alkyl, $CF_3$, $OR^{14}$, Cl, F, Br, I, =O, CN, $NO_2$, $NR^{15}R^{16}$, acetyl, —S($C_1$–$C_4$ alkyl), S(=O)($C_1$–$C_4$ alkyl), S(=O)$_2$($C_1$–$C_4$ alkyl);
  $C_3$–$C_{10}$ cycloalkyl substituted with 0–3 $R^{5c}$;
  $C_6$–$C_{10}$ aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H;

Ring B is selected from:

-continued

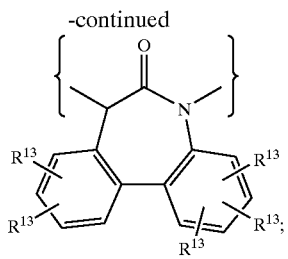

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
  $C_1$–$C_6$ alkyl substituted with 0–1 $R^{11a}$;
  $C_6$–$C_{10}$ aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, phenyl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is —$(CR^8R^{8a})_p$—;
p is 0, 1, or 2;
$R^8$ and $R^{8a}$, at each occurrence, are independently selected from H, F, methyl, and ethyl;
X is a bond;
  phenyl substituted with 0–3 $R^{Xb}$;
  $C_3$–$C_6$ cycloalkyl substituted with 0–3 $R^{Xb}$; or
  5 to 6 membered heterocycle containing 1 to 4 heteroatoms selected from nitrogen, oxygen, and sulphur, wherein said 5 to 6 membered heterocycle is substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond or —$(CR^9R^{9a})_t$—V—$(CR^9R^{9a})_u$—;
t is 0, 1, or 2;
u is 0, 1, or 2;
$R^9$ and $R^{9a}$, at each occurrence, are independently selected from H, F, methyl, and ethyl;
V is a bond, —C(=O)—, —O—, —S—, —S(=O)—, —$S(=O)_2$—, —$N(R^{19})$—, —C(=O)NH—, or —NHC(=O)—;
Z is H;
  $C_1$–$C_6$ alkyl substituted with 0–2 $R^{12}$;
  $C_2$–$C_6$ alkenyl substituted with 0–2 $R^{12}$;
  $C_2$–$C_6$ alkynyl substituted with 0–2 $R^{12}$;
  phenyl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_4$ alkyl, $C_1$–$C_4$ alkoxy, Cl, F, Br, CN, $NO_2$, and $CF_3$;

$R^{14}$, at each occurrence, is independently selected from H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, phenyl, benzyl, phenethyl, —C(=O)—($C_1$–$C_6$ alkyl) and —$S(=O)_2$—($C_1$–$C_6$ alkyl);

$R^{16}$, at each occurrence, is independently selected from H, OH, $C_1$–$C_6$ alkyl, phenyl, benzyl, phenethyl, —C(=O)—($C_1$–$C_6$ alkyl) and —$S(=O)_2$—($C_1$–$C_6$ alkyl);

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperizinyl;

$R^{17}$ is H, aryl, aryl-$CH_2$—, $C_1$–$C_6$ alkyl, or $C_2$–$C_6$ alkoxyalkyl;

$R^{18}$, at each occurrence, is independently selected from H, $C_1$–$C_6$ alkyl, phenyl, benzyl, phenethyl, —C(=O)—($C_1$–$C_6$ alkyl) and —$S(=O)_2$—($C_1$–$C_6$ alkyl);

$R^{19}$, at each occurrence, is independently selected from H, OH, $C_1$–$C_6$ alkyl, phenyl, benzyl, phenethyl, —C(=O)—($C_1$–$C_6$ alkyl) and —$S(=O)_2$—($C_1$–$C_6$ alkyl); and $R^{20}$ is H or $C_1$–$C_4$;

provided that when Q is phenyl, 3-F-phenyl, benzyl, propyl, or octyl; $R^2$ is H; $R^5$ is methyl, and —WXYZ is methyl, then Ring B is not

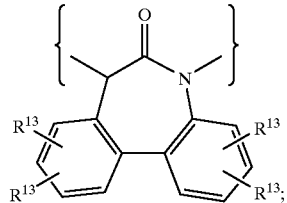

wherein $R^{13}$ is H.

[5] In another alternative embodiment of the present invention of of Formula (I), Ring B is

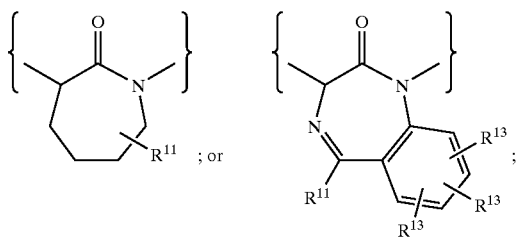
; or

Q is $C_1$–$C_6$ alkyl substituted with 0–2 $R^{1a}$;
$C_6$–$C_{10}$ aryl substituted with 0–3 $R^{1b}$; or
5 to 10 membered heterocycle containing 1 to 3 heteroatoms selected from nitrogen, oxygen, and sulphur, wherein said 5 to 10 membered heterocycle is substituted with 0–3 $R^{1b}$;

$R^{1a}$, at each occurrence, is independently selected from H, Cl, F, Br, $NR^{19}R^{20}$, $CF_3$, $C_1$–$C_4$ alkyl, $C_1$–$C_4$ haloalkyl, and phenyl substituted with 0–3 $R^{1b}$;

$R^{1b}$, at each occurrence, is independently selected from H, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy; —C(=O)—$R^{1d}$, —O—$R^{1d}$, —S(=O)$_2$—$R^{1d}$, —N($R^{19}$)—$R^{1d}$, —C(=O)N$R^{19b}R^{1d}$, —N$R^{19b}$C(=O)—$R^{1d}$, —N$R^{19b}$S(=O)$_2$—$R^{1d}$, —S(=O)$_2$N$R^{19b}$—$R^{1d}$, —C(=O)O—$R^{1d}$, —OC(=O)—$R^{1d}$;
$C_1$–$C_6$ alkyl substituted with 0–3 $R^{1c}$;
$C_6$–$C_{10}$ aryl substituted with 0–3 $R^{1f}$; and
5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)N$R^{19b}R^{1d}$, —N$R^{19b}$C(=O)—$R^{1d}$, —N$R^{19b}$S(=O)$_2$—$R^{1d}$, —S(=O)$_2$N$R^{19b}$—$R^{1d}$, —N$R^{19b}$S(=O)—$R^{1d}$, —S(=O)N$R^{19b}$—$R^{1d}$, —C(=O)O—$R^{1d}$, and —OC(=O)—$R^{1d}$;

$R^{1d}$, at each occurrence, is independently selected from H, $C_1$–$C_6$ alkyl, and $C_6$–$C_{10}$ aryl substituted with 0–3 $R^{1f}$;

$R^{1f}$, at each occurrence, is independently selected from H, Cl, F, Br, $NO_2$, $CF_3$, $C_1$–$C_4$ alkyl, $C_1$–$C_4$ haloalkyl, $C_1$–$C_4$ alkoxy, $C_1$–$C_4$ haloalkoxy, and $C_1$–$C_4$ haloalkyl-S—;

$R^5$ is $OR^{14}$;
$C_1$–$C_6$ alkyl substituted with 0–1 $R^{5b}$;
$C_2$–$C_6$ alkenyl substituted with 0–1 $R^{5b}$; or
$C_2$–$C_6$ alkynyl substituted with 0–1 $R^{5b}$;

$R^{5a}$ is H or $C_1$–$C_4$ alkyl;

$R^{5b}$, at each occurrence, is independently selected from: H, methyl, ethyl, propyl, butyl, $CF_3$, $OR^{14}$, Cl, F, Br, I, =O, CN, $NO_2$, $NR^{15}R^{16}$; acetyl, —S($C_1$–$C_4$ alkyl), —S(=O)($C_1$–$C_4$ alkyl), —S(=O)$_2$($C_1$–$C_4$ alkyl), $C_3$–$C_7$ cycloalkyl substituted with 0–3 $R^{5c}$;
phenyl substituted with 0–3 $R^{5c}$; and
5 to 7 membered heterocycle containing 1 to 4 heteroatoms selected from nitrogen, oxygen, and sulphur, wherein said 5 to 7 membered heterocycle is substituted with 0–3 $R^{5c}$;

$R^{5c}$, at each occurrence, is independently selected from H, OH, Cl, F, —$NR^{15}R^{16}$, $CF_3$, acetyl, $SCH_3$, $S(=O)_2CH_3$, methyl, ethyl, propyl, butyl, metrhoxy, ethoxy, propoxy, $C_1$–$C_2$ haloalkyl, and $C_1$–$C_2$ haloalkoxy;

$R^{11}$, at each occurrence, is independently selected from H, —$NR^{18}R^{19}$, —C(=O)$R^{17}$, —C(=O)O$R^{17}$, —C(=O)N$R^{18}R^{19}$, —S(=O)$_2$N$R^{18}R^{19}$, —$CF_3$;
$C_1$–$C_6$ alkyl substituted with 0–1 $R^{11a}$;
phenyl substituted with 0–3 $R^{11b}$;
$C_3$–$C_6$ carbocycle substituted with 0–3 $R^{11b}$; or
5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11a}$, at each occurrence, is independently selected from H, $C_1$–$C_4$ alkyl, $OR^{14}$, Cl, F, Br, CN, $NO_2$, $NR^{15}R^{16}$, $CF_3$, phenyl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is —$(CR^8R^{8a})_p$—;
p is 0, 1, or 2;
$R^8$ and $R^{8a}$, at each occurrence, are independently selected from H, F, methyl, and ethyl;

X is a bond;
phenyl substituted with 0–3 $R^{Xb}$;
$C_3$–$C_6$ cycloalkyl substituted with 0–3 $R^{Xb}$; or
5 to 6 membered heterocycle containing 1 to 4 heteroatoms selected from nitrogen, oxygen, and sulphur, wherein said 5 to 6 membered heterocycle is substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond or —$(CR^9R^{9a})_t$—V—$(CR^9R^{9a})_u$—;
t is 0, 1, or 2;
u is 0, 1, or 2;
$R^9$ and $R^{9a}$, at each occurrence, are independently selected from H, F, methyl, and ethyl;

V is a bond, —C(=O)—, —O—, —S—, —S(=O)—, —S(=O)$_2$—, —N($R^{19}$)—, —C(=O)NH—, or —NHC(=O)—;

Z is H;
$C_1$–$C_6$ alkyl substituted with 0–2 $R^{12}$;
$C_2$–$C_6$ alkenyl substituted with 0–2 $R^{12}$;
$C_2$–$C_6$ alkynyl substituted with 0–2 $R^{12}$;
phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

R$^{13}$, at each occurrence, is independently selected from H, OH, C$_1$–C$_3$ alkyl, C$_1$–C$_3$ alkoxy, Cl, F, Br, CN, NO$_2$, and CF$_3$;

R$^{14}$, at each occurrence, is independently selected from H, phenyl, benzyl, C$_1$–C$_6$ alkyl, and C$_2$–C$_6$ alkoxyalkyl;

R$^{15}$, at each occurrence, is independently selected from H, C$_1$–C$_6$ alkyl, phenyl, benzyl, phenethyl, —C(=O)—(C$_1$–C$_6$ alkyl) and —S(=O)$_2$—(C$_1$–C$_6$ alkyl);

R$^{16}$, at each occurrence, is independently selected from H, OH, C$_1$–C$_6$ alkyl, phenyl, benzyl, phenethyl, —C(=O)—(C$_1$–$_6$ alkyl) and —S(=O)$_2$—(C$_1$–C$_6$ alkyl);

alternatively, —NR$^{15}$R$^{16}$ may be a heterocyclic ring selected from the group piperidinyl, morpholinyl, thiomorpholinyl, pyrrolidinyl, homopiperidinyl, piperazinyl, and N-methylpiperizinyl;

R$^{17}$ is H, phenyl, benzyl, C$_1$–C$_4$ alkyl, or C$_2$–C$_4$ alkoxyalkyl;

R$^{18}$, at each occurrence, is independently selected from H, C$_1$–C$_6$ alkyl, phenyl, benzyl, phenethyl, —C(=O)—(C$_1$–C$_6$ alkyl) and —S(=O)$_2$—(C$_1$–C$_6$ alkyl);

R$^{19}$, at each occurrence, is independently selected from H, OH, methyl, ethyl, propyl, butyl, phenyl, benzyl, and phenethyl; and R$^{20}$ is H, methyl, ethyl, propyl, or butyl.

[6] In another alternative embodiment of the present invention of of Formula (I), Ring B is

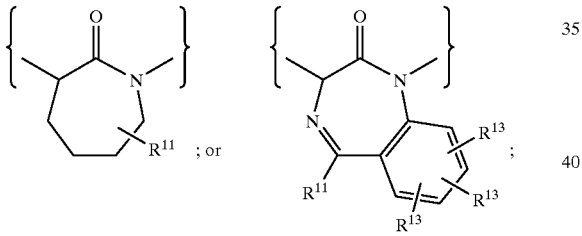

Q is C$_1$–C$_6$ alkyl substituted with 0–1 R$^{1a}$;
phenyl substituted with 0–3 R$^{1b}$;
naphthyl substituted with 0–3 R$^{1b}$; or
5 to 10 membered heterocycle containing 1 to 2 heteroatoms selected from nitrogen, oxygen, and sulphur, wherein said 5 to 10 membered heterocycle is substituted with 0–3 R$^{1b}$;

R$^{1a}$, at each occurrence, is independently selected from H, Cl, F, Br, —NR$^{19}$R$^{20}$, —CF$_3$; and phenyl substituted with 0–3 R$^{1b}$;

R$^{1b}$ at each occurrence, is independently selected from H, methyl, ethyl, OR$^{14}$, Cl, F, Br, NO$_2$, NR$^{19}$R$^{20}$, CF$_3$, OCF$_3$, C$_1$–C$_4$ alkoxy, C$_1$–C$_4$ haloalkoxy;
—C(=O)—R$^{1d}$, —O—R$^{1d}$, —S(=O)$_2$—R$^{1d}$, —N(R$^{19}$)—R$^{1d}$, —C(=O)NR$^{19b}$R$^{1d}$, —NR$^{19b}$C(=O)—R$^{1d}$, —NR$^{19b}$S(=O)$_2$—R$^{1d}$, —S(=O)$_2$NR$^{19b}$—R$^{1d}$, —C(=O)O—R$^{1d}$, —OC(=O)—R$^{1d}$;
C$_1$–C$_6$ alkyl substituted with 0–3 R$^{1c}$;
phenyl substituted with 0–3 R$^{1f}$; and
5 to 10 membered heterocycle containing 1 to 4 heteroatoms selected from nitrogen, oxygen, and sulphur, wherein said 5 to 10 membered heterocycle is substituted with 0–3 R$^{1f}$;

R$^{1c}$, at each occurrence, is independently selected from H, —C(=O)—R$^{1d}$, —O—R$^{1d}$, —S—R$^{1d}$, —S(=O)—R$^{1d}$, —S(=O)$_2$—R$^{1d}$, —N(R$^{19}$)—R$^{1d}$, —C(=O)NR$^{19b}$R$^{1d}$, —NR$^{19b}$C(=O)—R$^{1d}$, —NR$^{19b}$S(=O)$_2$—R$^{1d}$, and —S(=O)$_2$NR$^{19b}$—R$^{1d}$;

R$^{1d}$, at each occurrence, is independently selected from H, C$_1$–C$_6$ alkyl; and phenyl substituted with 0–3 R$^{1f}$;

R$^{1f}$, at each occurrence, is independently selected from H, Cl, F, Br, NO$_2$, CF$_3$, methyl, ethyl, propyl, methoxy, ethoxy, propoxy, C$_1$–C$_2$ haloalkyl, and C$_1$–C$_2$ haloalkoxy;

R$^5$ is OR$^{14}$ or C$_1$–C$_4$ alkyl substituted with 0–1 R$^{5b}$;

R$^{5a}$ is H;

R$^{5b}$, at each occurrence, is independently selected from: H, methyl, ethyl, propyl, butyl, —NR$^{15}$R$^{16}$;
C$_3$–C$_7$ cycloalkyl substituted with 0–3 R$^{5c}$;
phenyl substituted with 0–3 R$^{5c}$; or
5 to 7 membered heterocycle containing 1 to 4 heteroatoms selected from nitrogen, oxygen, and sulphur, wherein said 5 to 7 membered heterocycle is substituted with 0–3 R$^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R$^{5c}$, at each occurrence, is independently selected from H, OH, Cl, F, —NR$^{15}$R$^{16}$, CF$_3$, acetyl, SCH$_3$, S(=O)$_2$CH$_3$, methyl, and methoxy;

R$^{11}$, at each occurrence, is independently selected from H, NR$^{18}$R$^{19}$, CF$_3$;
C$_1$–C$_6$ alkyl substituted with 0–1 R$^{11a}$;
phenyl substituted with 0–3 R$^{11b}$;
C$_3$–C$_6$ carbocycle substituted with 0–3 R$^{11b}$; or
5 to 7 membered heterocycle containing 1 to 4 heteroatoms selected from nitrogen, oxygen, and sulphur, wherein said 5 to 7 membered heterocycle is substituted with 0–3 R$^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R$^{11a}$, at each occurrence, is independently selected from H, methyl, ethyl, propyl, butyl, methoxy, ethoxy, propoxy, Cl, F, Br, CN, NO$_2$, NR$^{15}$R$^{16}$, CF$_3$, phenyl substituted with 0–3 R$^{11b}$;
C$_3$–C$_6$ carbocycle substituted with 0–3 R$^{11b}$; or
5 to 7 membered heterocycle containing 1 to 4 heteroatoms selected from nitrogen, oxygen, and sulphur, wherein said 5 to 7 membered heterocycle is substituted with 0–3 R$^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R$^{11b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

W is —(CHR$^8$)$_p$—;

p is 0 or 1;

R$^8$ is H, methyl, or ethyl;

X is a bond;
phenyl substituted with 0–2 $R^{Xb}$;
$C_3$–$C_6$ cycloalkyl substituted with 0–3 $R^{Xb}$; or
5 to 6 membered heterocycle containing 1 to 4 heteroatoms selected from nitrogen, oxygen, and sulphur, wherein said 5 to 6 membered heterocycle is substituted with 0–1 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond, —V—, —$CH_2$—V—, —V—$CH_2$—, or —$CH_2$—V—$CH_2$—;

V is a bond, —C(=O)—, —O—, —S—, —S(=O)—, —S(=O)$_2$—, —N($R^{19}$)—, —C(=O)NH—, or —NHC(=O)—;

Z is H;
$C_1$–$C_6$ alkyl substituted with 0–2 $R^{12}$;
$C_2$–$C_6$ alkenyl substituted with 0–2 $R^{12}$;
$C_2$–$C_6$ alkynyl substituted with 0–2 $R^{12}$;
phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, methyl, ethyl, methoxy, ethoxy, Cl, F, Br, $NO_2$, or $CF_3$;

$R^{14}$, at each occurrence, is independently selected from H, phenyl, benzyl, $C_1$–$C_4$ alkyl, or $C_2$–$C_4$ alkoxyalkyl;

$R^{15}$, at each occurrence, is independently selected from H, methyl, ethyl, propyl, butyl, phenyl, benzyl, and phenethyl;

$R^{16}$, at each occurrence, is independently selected from H, OH, methyl, ethyl, propyl, butyl, phenyl, benzyl, phenethyl, $CH_3CH_2C(=O)$—, $CH_3C(=O)$—, $CH_3CH_2OC(=O)$—, $CH_3OC(=O)$—, $CH_3CH_2S(=O)_2$— and $CH_3S(=O)_2$—;

$R^{18}$, at each occurrence, is independently selected from H, methyl, ethyl, propyl, butyl, phenyl, benzyl, and phenethyl;

$R^{19}$, at each occurrence, is independently selected from H, OH, methyl, ethyl, propyl, and butyl; and $R^{20}$ is H, methyl, ethyl, propyl, or butyl.

[7] In another alternative embodiment of the present invention of of Formula (I), Ring B is

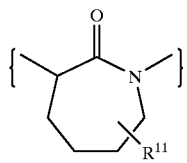 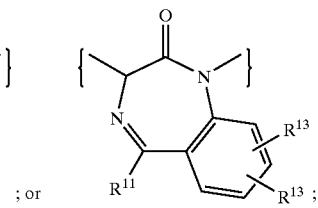

; or

Q is $C_1$–$C_4$ alkyl substituted with 0–1 $R^{1a}$;
phenyl substituted with 0–3 $R^{1b}$;
naphthyl substituted with 0–3 $R^{1b}$; or
5 to 10 membered heterocycle containing 1 to 2 heteroatoms selected from nitrogen, oxygen, and sulphur, wherein said 5 to 10 membered heterocycle is substituted with 0–3 $R^{1b}$; wherein said 5 to 10 membered heterocycle is selected from pyridinyl, quinolinyl, pyrimidinyl, triazinyl, furanyl, thienyl, thiazolyl, imidazolyl, oxazolyl, and isoxazolyl;

$R^{1a}$, at each occurrence, is independently selected from H, Cl, F, Br, $CF_3$, and phenyl substituted with 0–3 $R^{1b}$;

$R^{1b}$, at each occurrence, is independently selected from H, methyl, ethyl, $OR^{14}$, Cl, F, $NO_2$, $NR^{19}R^{20}$, $CF_3$, $OCF_3$, $C_1$–$C_4$ alkoxy, $C_1$–$C_4$ haloalkoxy; —C(=O)—$R^{1d}$, —O—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2NR^{19b}$—$R^{1d}$, —C(=O)O—$R^{1d}$, —OC(=O)—$R^{1d}$;
$C_1$–$C_6$ alkyl substituted with 0–3 $R^{1c}$;
phenyl substituted with 0–3 $R^{1f}$; and
5 to 6 membered heterocycle containing 1 to 4 heteroatoms selected from nitrogen, oxygen, and sulphur, wherein said 5 to 6 membered heterocycle is substituted with 0–3 $R^{1f}$;

$R^{1c}$, at each occurrence, is independently selected from H, —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR_{19b}$S(=O)$_2$—$R^{1d}$, and —S(=O)$_2NR^{19b}$—$R^{1d}$;

$R^{1d}$, at each occurrence, is independently selected from H, $C_1$–$C_6$ alkyl; and phenyl substituted with 0–3 $R^{1f}$;

$R^{1f}$, at each occurrence, is independently selected from H, Cl, F, Br, $NO_2$, $CF_3$, —$OCF_3$, methyl, ethyl, methoxy, and ethoxy;

$R^5$ is methyl substituted with 0–1 $R^{5b}$;
ethyl substituted with 0–1 $R^{5b}$;
propyl substituted with 0–1 $R^{5b}$; or
butyl substituted with 0–1 $R^{5b}$;

$R^{5a}$ is H;

$R^{5b}$, at each occurrence, is independently selected from: H, methyl, ethyl, and $NR^{15}R^{16}$;

$R^{11}$, at each occurrence, is independently selected from H, $NR^{18}R^{19}$, $CF_3$;
$C_1$–$C_4$ alkyl substituted with 0–1 $R^{11a}$;
phenyl substituted with 0–3 $R^{11b}$;
$C_3$–$C_6$ carbocycle substituted with 0–3 $R^{11b}$; or
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, $NR^{15}R^{16}$, $CF_3$;
  phenyl substituted with 0–3 $R^{11b}$;
  $C_3$–$C_6$ carbocycle substituted with 0–3 $R^{11b}$; or
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, methyl, ethyl, propyl, methoxy, and ethoxy;

W is a bond, —$CH_2$—, or —$CH(CH_3)$—;

X is a bond;
  phenyl substituted with 0–1 $R^{Xb}$;
  $C_3$–$C_6$ cycloalkyl substituted with 0–3 $R^{Xb}$; or
  5 to 6 membered heterocycle containing 1 to 3 heteroatoms selected from nitrogen, oxygen, and sulphur; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, and isoxazolyl;

Y is a bond, —V—, —$CH_2$—V—, or —V—$CH_2$—;

V is a bond, —C(=O)—, —O—, —S—, —S(=O)—, —S(=O)$_2$—, —N($R^{19}$)—, —C(=O)NH—, or —NHC(=O)—;

Z is H;
  $C_1$–$C_6$ alkyl substituted with 0–2 $R^{12}$;
  $C_2$–$C_6$ alkenyl substituted with 0–2 $R^{12}$;
  $C_2$–$C_6$ alkynyl substituted with 0–2 $R^{12}$;
  phenyl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, $NR^{15}R^{16}$, $CF_3$, $OCF_3$, acetyl, $SCH_3$, S(=O)$CH_3$, S(=O)$_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, methyl, methoxy, Cl, F, Br, and $CF_3$;

$R^{14}$ at each occurrence, is independently selected from H, phenyl, benzyl, methyl, ethyl, propyl, and butyl;

$R^{15}$, at each occurrence, is independently selected from H, methyl, ethyl, propyl, or butyl;

$R^{16}$, at each occurrence, is independently selected from H, OH, methyl, ethyl, propyl, butyl, phenyl, benzyl, and phenethyl;

$R^{18}$, at each occurrence, is independently selected from H, methyl, ethyl, propyl, butyl, phenyl, benzyl, and phenethyl;

$R^{19}$, at each occurrence, is independently selected from H, OH, methyl, ethyl, propyl, and butyl; and $R^{20}$ is H, methyl, ethyl, propyl, or butyl.

[8] In another alternative embodiment of the present invention of of Formula (I), Q is —$CH_3$, —$CH_2CH_3$, —$CH_2CH_2CH_3$, —$CH_2CH_2CH_2CH_3$, —$CH(CH_3)_2$, —$CH(CH_3)CH_2CH_3$, —$CH_2CH(CH_3)_2$, —$CH_2CF_3$, —$CH_2CH_2CF_3$, —$CH_2CH_2CH_2CF_3$, phenyl-, 4-tBu-phenyl-, 4-iPr-phenyl-, 4-Et-phenyl-, 2-F-phenyl-, 3-F-phenyl-, 4-F-phenyl-, 2-Cl-phenyl-, 3-Cl-phenyl-, 4-Cl-phenyl-, 2-Br-phenyl-, 3-Br-phenyl-, 4-Br-phenyl-, 2-$NO_2$-phenyl-, 3-$NO_2$-phenyl-, 4-$NO_2$-phenyl-, 2-$CH_3$-phenyl-, 3-$CH_3$-phenyl-, 4-$CH_3$-phenyl-, 2-$CH_3O$-phenyl-, 3-$CH_3O$-phenyl-, 4-$CH_3O$-phenyl-, 2-$CF_3$-phenyl-, 3-$CF_3$-phenyl-, 4-$CF_3$-phenyl-, 2-$CF_3O$-phenyl-, 3-$CF_3O$-phenyl-, 4-$CF_3O$-phenyl-, 2-$CH_3$CONH-phenyl, 3-$CH_3$CONH-phenyl, 4-$CH_3$CONH-phenyl, 2-methyoxycarbonyl-phenyl-, 4-phenyl-phenyl-, 2,3-diF-phenyl-, 2,4-diF-phenyl-, 2,5-diF-phenyl-, 2,6-diF-phenyl-, 3,4-diF-phenyl-, 3,5-diF-phenyl-, 2,3-diCl-phenyl-, 2,4-diCl-phenyl-, 2,5-diCl-phenyl-, 2,6-diCl-phenyl-, 3,4-diCl-phenyl-, 3,5-diCl-phenyl-, 3-F-4-Cl-phenyl-, 3-F-5-Cl-phenyl-, 3-Cl-4-F-phenyl-, 2,3-diMe-phenyl-, 2,4-diMe-phenyl-, 2,5-diMe-phenyl-, 2,6-diMe-phenyl-, 3,4-diMe-phenyl-, 3,5-diMe-phenyl-, 2,3-diMeO-phenyl-, 2,4-diMeO-phenyl-, 2,5-diMeO-phenyl-, 2,6-diMeO-phenyl-, 3,4-diMeO-phenyl-, 3,5-diMeO-phenyl-, 2,3-di$CF_3$-phenyl-, 2,4-di$CF_3$-phenyl-, 2,5-di$CF_3$-phenyl-, 2,6-di$CF_3$-phenyl-, 3,4-di$CF_3$-phenyl-, 3,5-di$CF_3$-phenyl-, 2-$NO_2$-4-$CF_3$-phenyl-, 2-Me-5-Cl-phenyl-, 2,4,6-triMe-phenyl, benzyl-, naphth-1-yl-, naphth-2-yl-, beta-styrene-, furanyl-, thienyl-, pyridyl-, thiazolyl-, imidazol-1-yl-, oxazolyl-, isoxazolyl-, quinolin-8-yl-, 3-methyl-isoxazol-4-yl-, 3,5-dimethyl-isoxazol-4-yl-, 3-bromo-5-chloro-thiophen-2-yl-, 2,3-dichlorothiophen-5-yl-, 4-bromo-5-chlorothiophen-2-yl-, 5-[(benzoylamino)methyl]-thiophen-2-yl-, 4-phenylsulfonylthiophen-2-yl-, 5-(phenylsulfonyl)thiophen-2-yl-, 2-(1-methyl-(5-trifluoromethyl)pyrazole)thiophen-5-yl-, 5-(2-pyridyl)thiophen-2-yl-, 1-methyl-5-(trifluoromethyl)imidazol-3-yl-, 2-(2-methylthio-pyrimdin-3-yl)-thiophen-5-yl-, or dibenzofuran-2-yl-;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, (3-$CH_3$-cyclobutyl)$CH_2CH_2$—, phenyl-$CH_2$—, (2-F-phenyl)$CH_2$—, (3-F-phenyl)$CH_2$—, (4-F-phenyl)$CH_2$—, furanyl-$CH_2$—, thienyl-$CH_2$—, pyridyl-$CH_2$—, 1-imidazolyl-$CH_2$—, oxazolyl-$CH_2$—, isoxazolyl-$CH_2$—, phenyl-$CH_2CH_2$—, (2-F-phenyl)$CH_2CH_2$—, (3-F-phenyl)$CH_2CH_2$-, (4-F-phenyl)$CH_2CH_2$—, furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, or isoxazolyl-$CH_2CH_2$—, W is a bond, —$CH_2$—, or —$CH(CH_3)$—;

X is a bond;

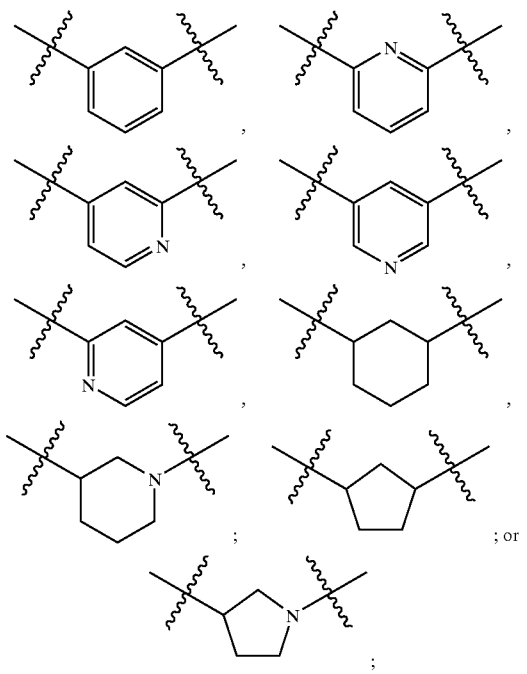

Y is a bond, —CH₂—V—, —V—, or —V—CH₂—;
V is a bond, —C(=O)—, —O—, —S—, —S(=O)—, —S(=O)₂—, —NH—, —N(CH₃)—, —C(=O)NH—, or —NHC(=O)—,
Z is H, —CH₃, —CH₂CH₃, —CH₂CH₂CH₃, —CH(CH₃)₂, —CH₂CH₂CH₂CH₃, —CH(CH₃)CH₂CH₃, —CH₂CH(CH₃)₂, —C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, —CH₂C(CH₃)₃, —C(CH₃)₂CH₂CH₃, —CH(CH₃)CH(CH₃)₂, —CH₂CH₂CH₂CH₂CH₂CH₃, —CH(CH₃)CH₂CH₂CH₂CH₃, —CH₂CH(CH₃)CH₂CH₂CH₃, —CH₂CH₂CH(CH₃)CH₂CH₃, —CH₂CH₂CH₂CH(CH₃)₂, —CH₂CH(CH₂CH₃)₂, —CH₂CH₂C(CH₃)₃, —CH(CH₂CH₃)CH₂CH₂CH₃, —CF₃, —CH₂CF₃, —CH₂CH₂CF₃, —CH₂CH₂CH₂CF₃, —CH₂CH₂CH₂CH₂CF₃, cyclopropyl-, (cyclopropyl)CH₂—, (cyclopropyl)CH₂CH₂—, cyclobutyl-, (cyclobutyl)CH₂—, (cyclobutyl)CH₂CH₂—, cyclopentyl-, (cyclopentyl)CH₂—, (cyclopentyl)CH₂CH₂—, cyclohexyl-, (cyclohexyl)CH₂—, (cyclohexyl)CH₂CH₂—, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl)CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-Me-phenyl)CH₂—, (3-Me-phenyl)CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl)CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl)CH₂—, (1-benzimidazolyl)CH₂—, morpholino)CH₂—, (N-piperidinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl)CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl)CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl)CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl)CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl)CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-piperidinyl)CH₂CH₂—;

$R^{11}$, at each occurrence, is independently selected from H, methyl, ethyl, propyl, butyl, phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, 4-F-phenyl, 4-Cl-phenyl, 4-CH₃-phenyl, 4-CF₃-phenyl, 4-CH₃O-phenyl, 4-CF₃O-phenyl, 3-F-phenyl, 3-Cl-phenyl, 3-CH₃-phenyl, 3-CF₃-phenyl, 3-CH₃O-phenyl, 3-CF₃O-phenyl, 2-F-phenyl, 2-Cl-phenyl, 2-CH₃-phenyl, 2-CF₃-phenyl, 2-CH₃O-phenyl, 2-CF₃O-phenyl, (4-F-phenyl)methyl-, (4-Cl-phenyl)methyl-, (4-CH₃-phenyl)methyl-, (4-CF₃-phenyl)methyl-, (4-CH₃O-phenyl)methyl-, (4-CF₃O-phenyl)methyl-, (3-F-phenyl)methyl-, (3-Cl-phenyl)methyl-, (3-CH₃-phenyl)methyl-, (3-CF₃-phenyl)methyl-, (3-CH₃O-phenyl)methyl-, (3-CF₃O-phenyl)methyl-, (2-F-phenyl)methyl-, (2-Cl-phenyl)methyl-, (2-CH₃-phenyl)methyl-, (2-CF₃-phenyl)methyl-, (2-CH₃O-phenyl)methyl-, (2-CF₃O-phenyl)

methyl-, 2-pyridyl-, 3-pyridyl-, 4-pyridyl-, 1-piperidinyl, 1-homopiperidinyl, and 1-morpholino; and $R^{13}$, at each occurrence, is independently selected from H, F, Cl, and methoxy.

[9] In another alternative embodiment of the present invention of of Formula (I), Q is —CH₃, —CH₂CH₃, —CH₂CH₂CH₃, —CH(CH₃)₂, phenyl-, 2-F-phenyl-, 2-Cl-phenyl-, 2-Br-phenyl-, 2-NO₂-phenyl-, 2-CH₃-phenyl-, 2-CH₃CH₂-phenyl-, 2-CH₃O-phenyl-, 2-CF₃-phenyl-, 2-CF₃O-phenyl-, 2-CH₃CONH-phenyl, or 3,5-dimethyl-isoxazol-4-yl-;

$R^5$ is —CH₃, —CH₂CH₃, —CH₂CH₂CH₃, —CH(CH₃)₂, —CH₂CH₂CH₂CH₃, —CH(CH₃)CH₂CH₃, —CH₂CH (CH₃)₂, —CH₂C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂,

W is a bond, —CH₂—, or —CH(CH₃)—;
X is a bond;

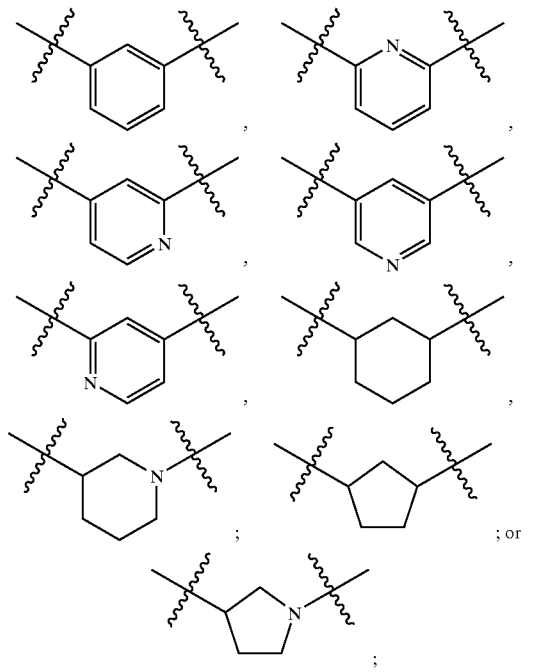

;

Y is a bond, —CH₂—V—, —V—, or —V—CH₂—;
V is a bond, —C(=O)—, —O—, —S—, —S(=O)—, —S(=O)₂—, —NH—, —N(CH₃)—, —C(=O) NH—, or —NHC(=O)—;
Z is H, —CH₃, —CH₂CH₃, —CH₂CH₂CH₃, —CH(CH₃)₂, —CH₂CH₂CH₂CH₃, —CH(CH₃) CH₂CH₃, —CH₂CH(CH₃)₂, —C(CH₃)₃, —CH₂CH₂CH₂CH₂CH₃, —CH(CH₃)CH₂CH₂CH₃, —CH₂CH(CH₃)CH₂CH₃, —CH₂CH₂CH(CH₃)₂, —CH(CH₂CH₃)₂, —CH₂C(CH₃)₃, —C(CH₃)₂CH₂CH₃, —CH(CH₃)CH(CH₃)₂, —CH₂CH₂CH₂CH₂CH₂CH₃, —CH(CH₃) CH₂CH₂CH₂CH₃, —CH₂CH(CH₃)CH₂CH₂CH₃, —CH₂CH₂CH(CH₃)CH₂CH₃, —CH₂CH₂CH₂CH (CH₃)₂, —CH₂CH(CH₂CH₃)₂, —CH₂CH₂C(CH₃)₃, —CH(CH₂CH₃)CH₂CH₂CH₃, —CF₃, —CH₂CF₃, —CH₂CH₂CF₃, —CH₂CH₂CH₂CF₃, —CH₂CH₂CH₂CH₂CF₃, cyclopropyl-, (cyclopropyl) CH₂—, (cyclopropyl)CH₂CH₂—, cyclobutyl-, (cyclobutyl)CH₂—, (cyclobutyl)CH₂CH₂—, cyclopentyl-, (cyclopentyl)CH₂—, (cyclopentyl) CH₂CH₂—, cyclohexyl-, (cyclohexyl)CH₂—, (cyclohexyl)CH₂CH₂—, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF₃O-phenyl, 3-CF₃O-phenyl, 4-CF₃O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidinyl, phenyl-CH₂—, (2-F-phenyl)CH₂—, (3-F-phenyl)CH₂—, (4-F-phenyl)CH₂—, (2-Cl-phenyl)CH₂—, (3-Cl-phenyl) CH₂—, (4-Cl-phenyl)CH₂—, (2,3-diF-phenyl)CH₂—, (2,4-diF-phenyl)CH₂—, (2,5-diF-phenyl)CH₂—, (2,6-diF-phenyl)CH₂—, (3,4-diF-phenyl)CH₂—, (3,5-diF-phenyl)CH₂—, (2,3-diCl-phenyl)CH₂—, (2,4-diCl-phenyl)CH₂—, (2,5-diCl-phenyl)CH₂—, (2,6-diCl-phenyl)CH₂—, (3,4-diCl-phenyl)CH₂—, (3,5-diCl-phenyl)CH₂—, (3-F-4-Cl-phenyl)CH₂—, (3-F-5-Cl-phenyl)CH₂—, (3-Cl-4-F-phenyl)CH₂—, (2-MeO-phenyl)CH₂—, (3-MeO-phenyl)CH₂—, (4-MeO-phenyl)CH₂—, (2-Me-phenyl)CH₂—, (3-Me-phenyl) CH₂—, (4-Me-phenyl)CH₂—, (2-MeS-phenyl)CH₂—, (3-MeS-phenyl)CH₂—, 4-MeS-phenyl)CH₂—, (2-CF₃O-phenyl)CH₂—, (3-CF₃O-phenyl)CH₂—, (4-CF₃O-phenyl)CH₂—, (furanyl)CH₂—, (thienyl) CH₂—, (pyridyl)CH₂—, (2-Me-pyridyl)CH₂—, (3-Me-pyridyl)CH₂—, (4-Me-pyridyl)CH₂—, (1-imidazolyl)CH₂—, (oxazolyl)CH₂—, (isoxazolyl) CH₂—, (1-benzimidazolyl)CH₂—, morpholino) CH₂—, (N-piperidinyl)CH₂—, phenyl-CH₂CH₂—, (phenyl)₂CHCH₂—, (2-F-phenyl)CH₂CH₂—, (3-F-phenyl)CH₂CH₂—, (4-F-phenyl)CH₂CH₂—, (2-Cl-phenyl)CH₂CH₂—, (3-Cl-phenyl)CH₂CH₂—, (4-Cl-phenyl)CH₂CH₂—, (2,3-diF-phenyl)CH₂CH₂—, (2,4-diF-phenyl)CH₂CH₂—, (2,5-diF-phenyl)CH₂CH₂—, (2,6-diF-phenyl)CH₂CH₂—, (3,4-diF-phenyl) CH₂CH₂—, (3,5-diF-phenyl)CH₂CH₂—, (2,3-diCl-phenyl)CH₂CH₂—, (2,4-diCl-phenyl)CH₂CH₂—, (2,5-diCl-phenyl)CH₂CH₂—, (2,6-diCl-phenyl) CH₂CH₂—, (3,4-diCl-phenyl)CH₂CH₂—, (3,5-diCl-phenyl)CH₂CH₂—, (3-F-4-Cl-phenyl)CH₂CH₂—, (3-F-5-Cl-phenyl)CH₂CH₂—, (3-Cl-4-F-phenyl) CH₂CH₂—, (2-MeO-phenyl)CH₂CH₂—, (3-MeO-phenyl)CH₂CH₂—, (4-MeO-phenyl)CH₂CH₂—, (2-Me-phenyl)CH₂CH₂—, (3-Me-phenyl)CH₂CH₂—, (4-Me-phenyl)CH₂CH₂—, (2-MeS-phenyl) CH₂CH₂—, (3-MeS-phenyl)CH₂CH₂—, (4-MeS-phenyl)CH₂CH₂—, (2-CF₃O-phenyl)CH₂CH₂—, (3-CF₃O-phenyl)CH₂CH₂—, (4-CF₃O-phenyl) CH₂CH₂—, (furanyl)CH₂CH₂—, (thienyl)CH₂CH₂—, (pyridyl)CH₂CH₂—, (2-Me-pyridyl)CH₂CH₂—, (3-Me-pyridyl)CH₂CH₂—, (4-Me-pyridyl)CH₂CH₂—, (imidazolyl)CH₂CH₂—, (oxazolyl)CH₂CH₂—, (isoxazolyl)CH₂CH₂—, (benzimidazolyl)CH₂CH₂—, (cyclopropyl)CH₂CH₂—, (cyclobutyl)CH₂CH₂—, (cyclopentyl)CH₂CH₂—, (cyclohexyl)CH₂CH₂—, (morpholino)CH₂CH₂—, or (N-piperidinyl) CH₂CH₂—;

$R^{11}$, at each occurrence, is independently selected from H, methyl, ethyl, propyl, butyl, phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, 4-F-phenyl, 4-Cl-phenyl, 4-$CH_3$-phenyl, 4-$CF_3$-phenyl, 4-$CH_3O$-phenyl, 4-$CF_3O$-phenyl, 3-F-phenyl, 3-Cl-phenyl, 3-$CH_3$-phenyl, 3-$CF_3$-phenyl, 3-$CH_3O$-phenyl, 3-$CF_3O$-phenyl, 2-F-phenyl, 2-Cl-phenyl, 2-$CH_3$-phenyl, 2-$CF_3$-phenyl, 2-$CH_3O$-phenyl, 2-$CF_3O$-phenyl, (4-F-phenyl)methyl-, (4-Cl-phenyl)methyl-, (4-$CH_3$-phenyl)methyl-, (4-$CF_3$-phenyl)methyl-, (4-$CH_3O$-phenyl)methyl-, (4-$CF_3O$-phenyl)methyl-, (3-F-phenyl)methyl-, (3-Cl-phenyl)methyl-, (3-$CH_3$-phenyl)methyl-, (3-$CF_3$-phenyl)methyl-, (3-$CH_3O$-phenyl)methyl-, (3-$CF_3O$-phenyl)methyl-, (2-F-phenyl)methyl-, (2-Cl-phenyl)methyl-, (2-$CH_3$-phenyl)methyl-, (2-$CF_3$-phenyl)methyl-, (2-$CH_3O$-phenyl)methyl-, (2-$CF_3O$-phenyl)methyl-, 2-pyridyl-, 3-pyridyl-, 4-pyridyl-, 1-piperidinyl, 1-homopiperidinyl, and 1-morpholino; and $R^{13}$, at each occurrence, is independently selected from H, F, Cl, and methoxy.

[10] In another alternative embodiment, the present invention provides a novel compound of Formula (Ic):

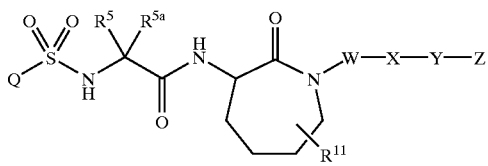

(Ic)

or a pharmaceutically acceptable salt form or prodrug thereof.

[11] In another alternative embodiment, the present invention provides a novel compound of Formula (Id):

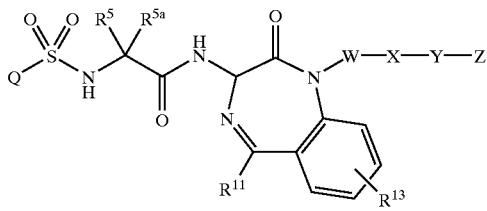

(I-d)

or a pharmaceutically acceptable salt form or prodrug thereof.

[12] In another alternative embodiment, the present invention provides a novel compound of Formula (Ia);

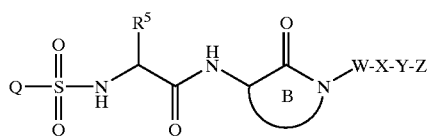

or a pharmaceutically acceptable salt or prodrug thereof.

[13] In another alternative embodiment of the present invention of Formula (I), $R^5$ is $OR^{14}$.

[14] In another alternative embodiment of the present invention of Formula (I), $R^5$ is $C_1$–$C_4$ alkoxy substituted with 0–3 $R^{5b}$.

[15] In a preferred embodiment the present invention provides compound of Formula (I), (Ia), (Ic), or (Id) wherein Q is 3,5-dimethyl-isoxazol-4-yl-.

In a preferred embodiment Q is —$CH_3$, —$CH_2CH_3$, —$CH_2CH_2CH_3$, —$CH(CH_3)_2$, phenyl-, 2-F-phenyl-, 2-Cl-phenyl-, 2-Br-phenyl-, 2-$NO_2$-phenyl-, 2-$CH_3$-phenyl-, 2-$CH_3CH_2$-phenyl-, 2-$CH_3O$-phenyl-, 2-$CF_3$-phenyl-, 2-$CF_3O$-phenyl-, 2-$CH_3CONH$-phenyl, or 3,5-dimethyl-isoxazol-4-yl-.

In a preferred embodiment Q is a substituted phenyl as disclosed herein (preferably ortho substituted) or a 5 to 6 membered heterocyclic ring as disclosed herein (preferably substituted); for example, 2-F-phenyl-, 2-Cl-phenyl-, 2-Br-phenyl-, 2-$NO_2$-phenyl-, 2-$CH_3$-phenyl-, 2-$CH_3CH_2$-phenyl-, 2-$CH_3O$-phenyl-, 2-$CF_3$-phenyl-, 2-$CF_3O$-phenyl-, 2-$CH_3CONH$-phenyl, or 3,5-dimethyl-isoxazol-4-yl-.

In a preferred embodiment Q is not a trihalomethyl group, preferrably not trifluoromethyl.

In a preferred embodiment when $R^5$ and/or $R^{5a}$ form an alkyl or alkeneyl moiety, optionally substituted, of five carbons or less, then Q is not a haloalkyl, preferably not trifluoromethyl.

It is understood that any and all embodiments of the present invention may be taken in conjunction with any other embodiment to descibe additional even more preferred embodiments of the present invention.

[16] In another alternative embodiment, the present invention provides a compound selected from:

2-(3,5-dimethyl-isoxazole-4-sulfonylamino)-4-methyl-pentanoic acid (1-methyl-2-oxo-5-phenyl-2,3-dihydro-1H-benzo[e][1,4]diazepin-3-yl)-amide;

2-(3,5-dimethyl-isoxazole-4-sulfonylamino)-N-(1-methyl-2-oxo-5-phenyl-2,3-dihydro-1H-benzo[e][1,4]diazepin-3-yl)-propionamide;

2-(3-bromo-5-chloro-thiophene-2-sulfonylamino)-4-methyl-pentanoic acid (1-methyl-2-oxo-5-phenyl-2,3-dihydro-1H-benzo[e][1,4]diazepin-3-yl)-amide;

2-(naphthalene-1-sulfonylamino)-4-methyl-pentanoic acid (1-methyl-2-oxo-5-phenyl-2,3-dihydro-1H-benzo[e][1,4]diazepin-3-yl)-amide;

2-(5-dimethylamino naphthalene-1-sulfonylamino)-4-methyl-pentanoic acid (1-methyl-2-oxo-5-phenyl-2,3-dihydro-1H-benzo[e][1,4]diazepin-3-yl)-amide;

2-(naphthalene-2-sulfonylamino)-4-methyl-pentanoic acid (1-methyl-2-oxo-5-phenyl-2,3-dihydro-1H-benzo[e][1,4]diazepin-3-yl)-amide;

2-(2-acetamido-4-methylthiazole-5-sulfonylamino)-4-methyl-pentanoic acid (1-methyl-2-oxo-5-phenyl-2,3-dihydro-1H-benzo[e][1,4]diazepin-3-yl)-amide;

2-(thiophene-2-sulfonylamino)-4-methyl-pentanoic acid (1-methyl-2-oxo-5-phenyl-2,3-dihydro-1H-benzo[e][1,4]diazepin-3-yl)-amide;

2-(quinoline-8-sulfonylamino)-4-methyl-pentanoic acid (1-methyl-2-oxo-5-phenyl-2,3-dihydro-1H-benzo[e][1,4]diazepin-3-yl)-amide;

2-(phenyl-sulfonylamino)-4-methyl-pentanoic acid (1-methyl-2-oxo-5-phenyl-2,3-dihydro-1H-benzo[e][1,4]diazepin-3-yl)-amide;

2-(2,5-dichlorophenyl sulfonylamino)-4-methyl-pentanoic acid (1-methyl-2-oxo-5-phenyl-2,3-dihydro-1H-benzo[e][1,4]diazepin-3-yl)-amide;

2-(mesitylene-2-sulfonylamino)-4-methyl-pentanoic acid (1-methyl-2-oxo-5-phenyl-2,3-dihydro-1H-benzo[e][1,4]diazepin-3-yl)-amide;

2-(3-nitrophenyl-sulfonylamino)-4-methyl-pentanoic acid (1-methyl-2-oxo-5-phenyl-2,3-dihydro-1H-benzo[e][1,4]diazepin-3-yl)-amide;

2-(4-bromophenyl-sulfonylamino)-4-methyl-pentanoic acid (1-methyl-2-oxo-5-phenyl-2,3-dihydro-1H-benzo[e][1,4]diazepin-3-yl)-amide;

2-(4-fluorophenyl-sulfonylamino)-4-methyl-pentanoic acid (1-methyl-2-oxo-5-phenyl-2,3-dihydro-1H-benzo[e][1,4]diazepin-3-yl)-amide;

2-(4-chlorophenyl-sulfonylamino)-4-methyl-pentanoic acid (1-methyl-2-oxo-5-phenyl-2,3-dihydro-1H-benzo[e][1,4]diazepin-3-yl)-amide;

2-(4-acetamidophenyl-sulfonylamino)-4-methyl-pentanoic acid (1-methyl-2-oxo-5-phenyl-2,3-dihydro-1H-benzo[e][1,4]diazepin-3-yl)-amide;

2-(4-nitrophenyl-sulfonylamino)-4-methyl-pentanoic acid (1-methyl-2-oxo-5-phenyl-2,3-dihydro-1H-benzo[e][1,4]diazepin-3-yl)-amide;

2-(4-methoxyphenyl-sulfonylamino)-4-methyl-pentanoic acid (1-methyl-2-oxo-5-phenyl-2,3-dihydro-1H-benzo[e][1,4]diazepin-3-yl)-amide;

2-(4-tert-butylphenyl-sulfonylamino)-4-methyl-pentanoic acid (1-methyl-2-oxo-5-phenyl-2,3-dihydro-1H-benzo[e][1,4]diazepin-3-yl)-amide;

2-(p-toluene-sulfonylamino)-4-methyl-pentanoic acid (1-methyl-2-oxo-5-phenyl-2,3-dihydro-1H-benzo[e][1,4]diazepin-3-yl)-amide;

2-(benzyl-sulfonylamino)-4-methyl-pentanoic acid (1-methyl-2-oxo-5-phenyl-2,3-dihydro-1H-benzo[e][1,4]diazepin-3-yl)-amide;

2-(beta-styrene-sulfonylamino)-4-methyl-pentanoic acid (1-methyl-2-oxo-5-phenyl-2,3-dihydro-1H-benzo[e][1,4]diazepin-3-yl)-amide;

2-((2-methoxycarbonyl)phenyl-sulfonylamino)-4-methyl-pentanoic acid (1-methyl-2-oxo-5-phenyl-2,3-dihydro-1H-benzo[e][1,4]diazepin-3-yl)-amide;

2-(2-nitro-4-(trifluoromethyl)phenyl-sulfonylamino)-4-methyl-pentanoic acid (1-methyl-2-oxo-5-phenyl-2,3-dihydro-1H-benzo[e][1,4]diazepin-3-yl)-amide;

2-(3-(trifluoromethyl)phenyl-sulfonylamino)-4-methyl-pentanoic acid (1-methyl-2-oxo-5-phenyl-2,3-dihydro-1H-benzo[e][1,4]diazepin-3-yl)-amide;

2-(2,5-dimethoxyphenyl-sulfonylamino)-4-methyl-pentanoic acid (1-methyl-2-oxo-5-phenyl-2,3-dihydro-1H-benzo[e][1,4]diazepin-3-yl)-amide;

2-(2-methylphenyl-sulfonylamino)-4-methyl-pentanoic acid (1-methyl-2-oxo-5-phenyl-2,3-dihydro-1H-benzo[e][1,4]diazepin-3-yl)-amide;

2-(3,4-dichlorophenyl-sulfonylamino)-4-methyl-pentanoic acid (1-methyl-2-oxo-5-phenyl-2,3-dihydro-1H-benzo[e][1,4]diazepin-3-yl)-amide;

2-(4-(trifluoromethoxy)phenyl-sulfonylamino)-4-methyl-pentanoic acid (1-methyl-2-oxo-5-phenyl-2,3-dihydro-1H-benzo[e][1,4]diazepin-3-yl)-amide;

2-(3,4-dimethoxyphenyl-sulfonylamino)-4-methyl-pentanoic acid (1-methyl-2-oxo-5-phenyl-2,3-dihydro-1H-benzo[e][1,4]diazepin-3-yl)-amide;

2-(2-bromophenyl-sulfonylamino)-4-methyl-pentanoic acid (1-methyl-2-oxo-5-phenyl-2,3-dihydro-1H-benzo[e][1,4]diazepin-3-yl)-amide;

2-(3,5-bis(trifluoromethyl)phenyl-2-sulfonylamino)-4-methyl-pentanoic acid (1-methyl-2-oxo-5-phenyl-2,3-dihydro-1H-benzo[e][1,4]diazepin-3-yl)-amide;

2-(4-ethylphenyl-sulfonylamino)-4-methyl-pentanoic acid (1-methyl-2-oxo-5-phenyl-2,3-dihydro-1H-benzo[e][1,4]diazepin-3-yl)-amide;

2-(4-isopropylphenyl-sulfonylamino)-4-methyl-pentanoic acid (1-methyl-2-oxo-5-phenyl-2,3-dihydro-1H-benzo[e][1,4]diazepin-3-yl)-amide;

2-(2,5-dichlorothiophene-3-sulfonylamino)-4-methyl-pentanoic acid (1-methyl-2-oxo-5-phenyl-2,3-dihydro-1H-benzo[e][1,4]diazepin-3-yl)-amide;

2-(5-chlorothiophene-2-sulfonylamino)-4-methyl-pentanoic acid (1-methyl-2-oxo-5-phenyl-2,3-dihydro-1H-benzo[e][1,4]diazepin-3-yl)-amide;

2-(2-(trifluoromethyl)phenyl-sulfonylamino)-4-methyl-pentanoic acid (1-methyl-2-oxo-5-phenyl-2,3-dihydro-1H-benzo[e][1,4]diazepin-3-yl)-amide;

2-(3-methylphenyl-sulfonylamino)-4-methyl-pentanoic acid (1-methyl-2-oxo-5-phenyl-2,3-dihydro-1H-benzo[e][1,4]diazepin-3-yl)-amide;

2-(2,3-dichlorothiophene-5-sulfonylamino)-4-methyl-pentanoic acid (1-methyl-2-oxo-5-phenyl-2,3-dihydro-1H-benzo[e][1,4]diazepin-3-yl)-amide;

2-(4-bromo-5-chlorothiophene-2-sulfonylamino)-4-methyl-pentanoic acid (1-methyl-2-oxo-5-phenyl-2,3-dihydro-1H-benzo[e][1,4]diazepin-3-yl)-amide;

2-(5-[(benzoylamino)methyl]-thiophene-2-sulfonylamino)-4-methyl-pentanoic acid (1-methyl-2-oxo-5-phenyl-2,3-dihydro-1H-benzo[e][1,4]diazepin-3-yl)-amide;

2-(4-phenylsulfonylthiophene-2-sulfonylamino)-4-methyl-pentanoic acid (1-methyl-2-oxo-5-phenyl-2,3-dihydro-1H-benzo[e][1,4]diazepin-3-yl)-amide;

2-(5-(phenylsulfonyl)thiophene-2-sulfonylamino)-4-methyl-pentanoic acid (1-methyl-2-oxo-5-phenyl-2,3-dihydro-1H-benzo[e][1,4]diazepin-3-yl)-amide;

2-[2-(1-methyl-(5-trifluoromethyl)pyrazole)thiophene-5-sulfonylamino]-4-methyl-pentanoic acid (1-methyl-2-oxo-5-phenyl-2,3-dihydro-1H-benzo[e][1,4]diazepin-3-yl)-amide;

2-(5-(2-pyridyl)thiophene-2-sulfonylamino)-4-methyl-pentanoic acid (1-methyl-2-oxo-5-phenyl-2,3-dihydro-1H-benzo[e][1,4]diazepin-3-yl)-amide;

2-2-(3,5-dimethyl-isoxazole-4-sulfonylamino)-4-methyl-pentanoic acid [5-(4-fluoro-phenyl)-1-methyl-2-oxo-2,3-dihydro-1H-benzo[e][1,4]diazepin-3-yl]-amide;

N-[1-(3'-Chloro-4'-fluoro-biphenyl-3-ylmethyl)-2-oxo-azepan-3-yl]-2-(3,5-dimethyl-isoxazole-4-sulfonylamino)-propionamide;

2-(3,5-dimethyl-isoxazole-4-sulfonylamino)-N-[5-(4-fluoro-phenyl)-1-methyl-2-oxo-2,3-dihydro-1H-benzo[e][1,4]diazepin-3-yl]-propionamide;

2-(2-fluoro-benzenesulfonylamino)-N-[5-(4-fluoro-phenyl)-1-methyl-2-oxo-2,3-dihydro-1H-benzo[e][1,4]diazepin-3-yl]-propionamide;

N-(1-methyl-2-oxo-5-phenyl-2,3-dihydro-1H-benzo[e][1,4]diazepin-3-yl)-2-(2-trifluoromethyl-benzenesulfonylamino)-propionamide;

2-(2-fluoro-benzenesulfonylamino)-4-methyl-pentanoic acid (1-methyl-2-oxo-5-phenyl-2,3-dihydro-1H-benzo[e][1,4]diazepin-3-yl)-amide;

4-methyl-2-(2-trifluoromethyl-benzenesulfonylamino)-pentanoic acid (1-methyl-2-oxo-5-phenyl-2,3-dihydro-1H-benzo[e][1,4]diazepin-3-yl)-amide;

4-methyl-2-(propane-1-sulfonylamino)-pentanoic acid (1-methyl-2-oxo-5-phenyl-2,3-dihydro-1H-benzo[e][1,4]diazepin-3-yl)-amide;

4-methyl-2-(propane-1-sulfonylamino)-pentanoic acid (1-methyl-2-oxo-5-phenyl-2,3-dihydro-1H-benzo[e][1,4]diazepin-3-yl)-amide;

2-(3,5-dimethyl-isoxazole-4-sulfonylamino)-N-[1-methyl-2-oxo-5-(4-trifluoromethyl-phenyl)-2,3-dihydro-1H-benzo[e][1,4]diazepin-3-yl]-propionamide;

2-(3,5-dimethyl-isoxazole-4-sulfonylamino)-4-methyl-pentanoic acid (7-chloro-1-methyl-2-oxo-5-phenyl-2,3-dihydro-1H-benzo[e][1,4]diazepin-3-yl)-amide;

4-methyl-2-(propane-1-sulfonylamino)-pentanoic acid [5-(4-chloro-phenyl)-1-methyl-2-oxo-2,3-dihydro-1H-benzo[e][1,4]diazepin-3-yl]-amide;

2-(3,5-dimethyl-isoxazole-4-sulfonylamino)-4-methyl-pentanoic acid (1-methyl-2-oxo-5-pyridin-2-yl-2,3-dihydro-1H-benzo[e][1,4]diazepin-3-yl)-amide;

2-[(3,5-dimethyl-isoxazole-4-sulfonyl)-methyl-amino]-N-(1-methyl-2-oxo-5-phenyl-2,3-dihydro-1H-benzo[e][1,4]diazepin-3-yl)-propionamide;

3-dimethylamino-2-(3,5-dimethyl-isoxazole-4-sulfonylamino)-N-(1-methyl-2-oxo-5-phenyl-2,3-dihydro-1H-benzo[e][1,4]diazepin-3-yl)-propionamide;

N-[1-methyl-2-oxo-5-(4-trifluoromethyl-phenyl)-2,3-dihydro-1H-benzo[e][1,4]diazepin-3-yl]-2-(propane-1-sulfonylamino)-propionamide;

N-(7-chloro-1-methyl-2-oxo-5-phenyl-2,3-dihydro-1H-benzo[e][1,4]diazepin-3-yl)-2-(3,5-dimethyl-isoxazole-4-sulfonylamino)-propionamide;

2-(3,5-dimethyl-isoxazole-4-sulfonylamino)-4-methyl-pentanoic acid [5-(4-chloro-phenyl)-1-methyl-2-oxo-2,3-dihydro-1H-benzo[e][1,4]diazepin-3-yl]-amide; and 2-methanesulfonylamino-N-[1-methyl-2-oxo-5-(4-trifluoromethyl-phenyl)-2,3-dihydro-1H-benzo[e][1,4]diazepin-3-yl]-propionamide.

In another embodiment, the present invention provides a pharmaceutical composition comprising a compound of Formula (I) and a pharmaceutically acceptable carrier.

In another embodiment, the present invention provides a method for the treatment of neurological disorders comprising administering to a host in need of such treatment a therapeutically effective amount of a compound of Formula (I).

In another embodiment, the present invention provides a method for the treatment of neurological disorders associated with Aβ amyloid production comprising administering to a host in need of such treatment a therapeutically effective amount of a compound of Formula (I).

In another embodiment, the present invention provides a method for the treatment of Alzheimer's Disease comprising administering to a host in need of such treatment a therapeutically effective amount of a compound of Formula (I).

In another embodiment, the present invention provides a method for the treatment of Alzheimer's Disease associated with Aβ amyloid production comprising administering to a host in need of such treatment a therapeutically effective amount of a compound of Formula (I).

In another embodiment, the present invention provides a method for for inhibiting γ-secretase activity comprising administering to a host in need of such inhibition a therapeutically effective amount of a compound of Formula (I) that inhibits γ-secretase activity.

In another embodiment the present invention provides a compound of Formula (I) for use in therapy of Alzheimer's Disease.

In another embodiment the present invention provides for the use of a compound of Formula (I) for the manufacture of a medicament for the treatment of Alzheimer's Disease.

DEFINITIONS

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No 4,666,829. The 43 amino acid sequence is:

```
 1
Asp Ala Glu Phe Arg His Asp Ser Gly Tyr

11
Glu Val His His Gln Lys Leu Val Phe Phe

21
Ala Glu Asp Val Gly Ser Asn Lys Gly Ala

31
Ile Ile Gly Leu Met Val Gly Gly Val Val

41
Ile Ala Thr
```

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated γ secretase, generating the N-terminus of Aβ, γ secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{1a}$, $R^2$, $R^{13}$ etc.) occurs more than one time in any constituent or formula for a compound, its definition at each occurrence is independent of its definition at every other occurrence. Thus, for example, if a group is shown to be substituted with 0–3 $R^{1a}$, then said group may optionally be substituted with up to three $R^{1a}$ groups and $R^{1a}$ at each occurrence is selected independently from the definition of $R^{1a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group is "$C_1$–$C_4$ alkyl" wherein methyl, ethyl, n-propyl, i-propyl, n-butyl, and i-butyl, are specifically preferred. As used herein, "$C_1$–$C_3$ alkyl", whether a terminal substituent or a alkylene group linking two substituents, is understood to specifically include both branched and straight-chain methyl, ethyl, and propyl.

As used herein, "alkenyl" or "alkenylene" is intended to include hydrocarbon chains of either a straight or branched configuration and one or more unsaturated carbon-carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon-carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred example of "$C_3$–$C_{10}$ carbocycle" or "$C_3$–$C_6$ carbocycle" is $C_3$–$C_6$ cycloalkyl, specifically cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms, preferably 1, 2, or 3 heteroatoms, independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, isoxazolinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Unless otherwise specified, "aryl" may be unsubstituted or substituted with 0 to 3 groups selected from H, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "amino acid" as used herein, refers to natural, modified or unnatural amino acids of either D- or L-configuration and means an organic compound containing both a basic amino group and an acidic carboxyl group. Natural amino acids residues are Ala, Arg, Asn, Asp, Aze, Cys, Gln, Glu, Gly, His, Hyp, Ile, Irg Leu, Lys, Met, Orn, Phe, Phe(4-fluoro), Pro, Sar, Ser, Thr, Trp, Tyr, and Val. Roberts and Vellaccio, The Peptides, Vol 5; 341–449 (1983), Academic Press, New York, discloses numerous suitable unnatural amino acids and is incorporated herein by reference for that purpose.

The phrase "additional lactam carbons", as used herein, is intended to denote the number of optional carbon atoms in the lactam ring B of Formula (I). Formula (Ia):

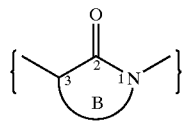

(Ia)

represents the lactam ring B of Formula (I). Additional lactam carbons are carbons in lactam ring B other than the carbons numbered 2 and 3 in the backbone of the formula. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. Examples of lactam ring B include:

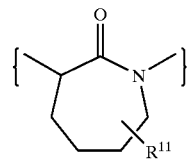

B1

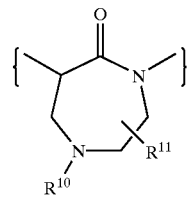

B2

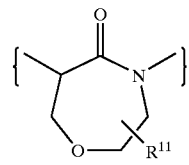

B3

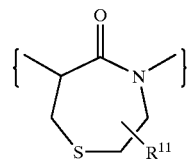

B4

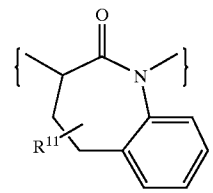

B5

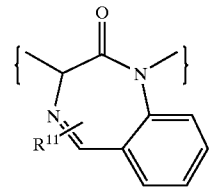

B6

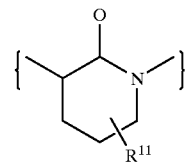

B7

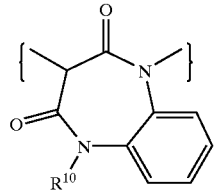

B8

-continued

B9 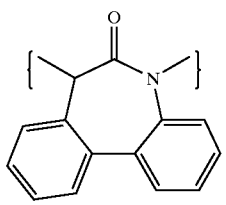

B10 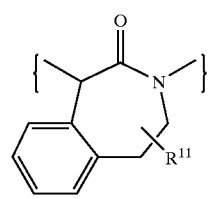

B11 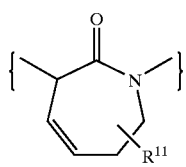

B12 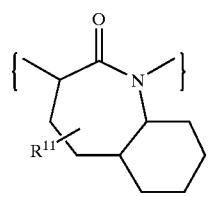

B13 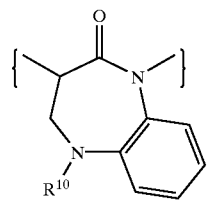

B14 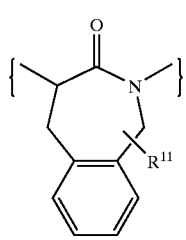

B15 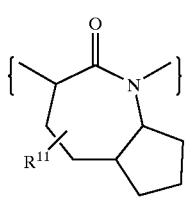

-continued

B16 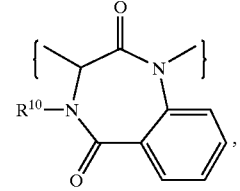

but are not intended to limit the invention. Preferred examples of lactam ring B are B1, B2, B5, B6, B8, B9, B13, and B16; more preferred examples of lactam ring B are B1, B6, B8, B9, and B13; even more preferred examples of lactam ring B are B1 and B6. Preferred examples of substituent $R^{10}$ or $R^{11}$ on lactam ring B are methyl, ethyl, phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, 4-F-phenyl, 4-Cl-phenyl, 4-CH$_3$-phenyl, 4-CF$_3$-phenyl, 4-CH$_3$O-phenyl, 4-CF$_3$O-phenyl, 3-F-phenyl, 3-Cl-phenyl, 3-CH$_3$-phenyl, 3-CF$_3$-phenyl, 3-CH$_3$O-phenyl, 3-CF$_3$O-phenyl, (4-F-phenyl)methyl-, (4-Cl-phenyl)methyl-, (4-CH$_3$-phenyl)methyl-, (4-CF$_3$-phenyl)methyl-, (4-CH$_3$O-phenyl)methyl-, (4-CF$_3$O-phenyl)methyl-, (3-F-phenyl)methyl-, (3-Cl-phenyl)methyl-, (3-CH$_3$-phenyl)methyl-, (3-CF$_3$-phenyl)methyl-, (3-CH$_3$O-phenyl)methyl-, (3-CF$_3$O-phenyl)methyl-, 2-pyridyl-, 3-pyridyl-, and 4-pyridyl-. More preferred examples of substituent $R^{10}$ or $R^{11}$ on lactam ring B are methyl, ethyl, phenyl, 4-fluorophenyl, 4-chlorophenyl, 4-trifluorophenyl, (4-fluorophenyl)methyl, (4-chlorophenyl)methyl, (4-trifluorophenyl)methyl, 2-pyridyl-, 3-pyridyl-, and 4-pyridyl-. The fused rings on lactam ring B may optionally be substituted with $R^{13}$, wherein the preferred examples of substituent $R^{13}$ on fused rings of lactam B are methyl, fluoro, chloro, and methoxy.

The compounds herein described may have asymmetric centers. One enantiomer of a compound of Formula (I) may display superior biological activity over the opposite enantiomer. For example carbon 3 of lactam ring B Formula (I″) may exist in either an S or R configuration. Thus, an R or S configuration at carbon 3 in Formula (I″) is considered part of the invention. Examples of such configuration include,

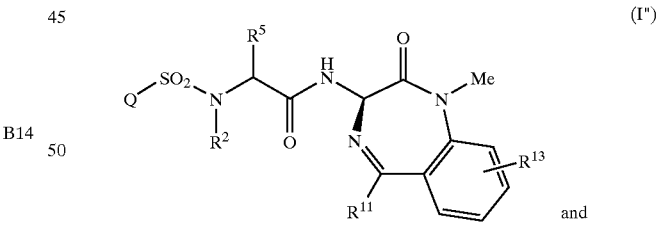

and

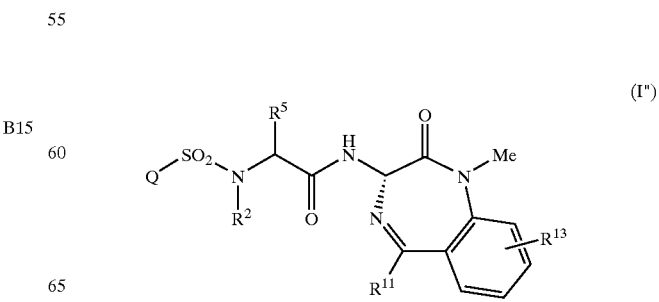

but are not intended to be limited to these examples of ring B. When required, separation of the racemic material can be achieved by methods known in the art. Additionally, the carbon atom to which $R^5$ is attached may display superior biological activity over the opposite enantiomer. For example, where $R^5$ is not H, then the configuration of the carbon may be described as R or S. All configurations are considered part of the invention.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol or acetamide, formamide, benzamide, and N-oxide derivatives of amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of Formula (I) of the present invention can be synthesized by the method of Scheme 1 comprising: step 1, an amino acid coupling; followed by step 2, a deprotection; followed by step 3, a sulfonyl coupling (see Scheme 1). In the method of Scheme 1, a W-X-Y-Z-substituted aminolactam, X, is coupled with a protected natural or unnatural amino acid, XI, to form a compound, XII. The amino protecting group of XII is then removed using a standard deprotection procedure to give a compound XIII. The compound XIII is coupled with an activated sulfonylating agent, XIV, preferably a sulfonyl chloride Q—SO$_2$Cl, XIVa, to form a compound of Formula I.

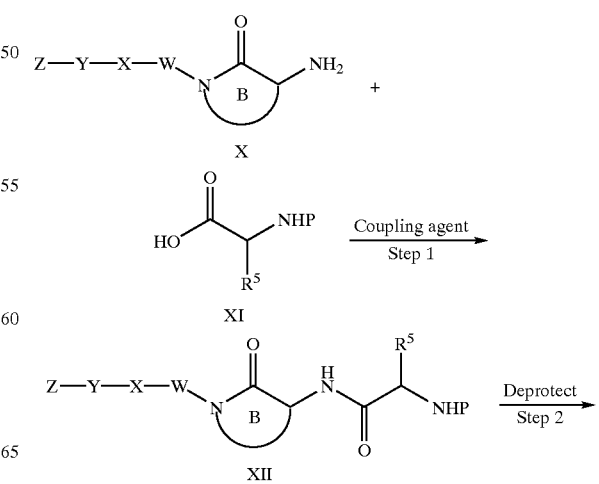

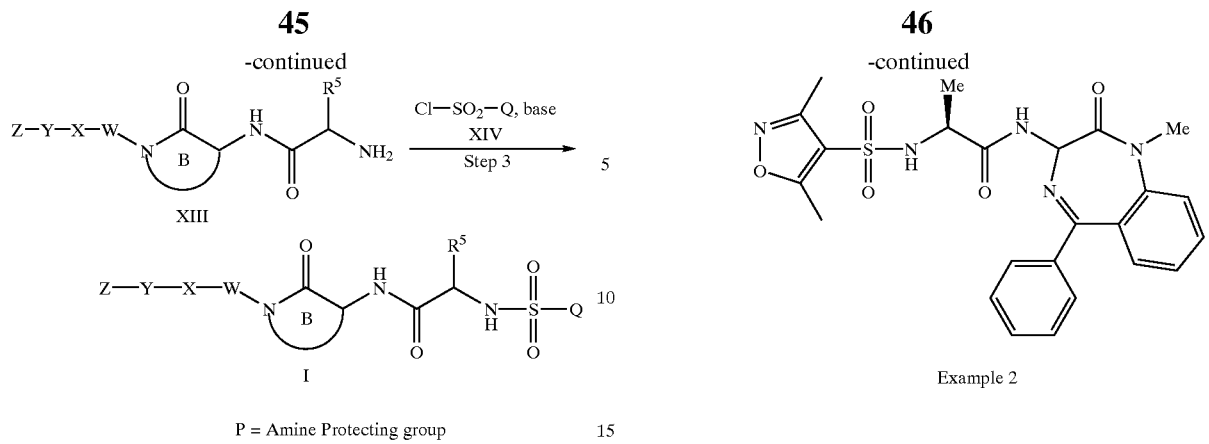

P = Amine Protecting group

In an example of the method of Scheme 1, the coupling of Bob-Alaine to the racemic 3-amino-1-methyl-5-phenyl-1,3-dihydro-benzo[e][1,4]diazepin-2-one followed by TFA-mediated removal of the Boc group provides the Alanine-substituted lactam 2b (Scheme 1a). Sulfonamide formation using 3,5-Dimethyl-isoxazole-4-sulfonyl chloride and tri-ethylamine as base provides the compound of Example 2.

Scheme 1a

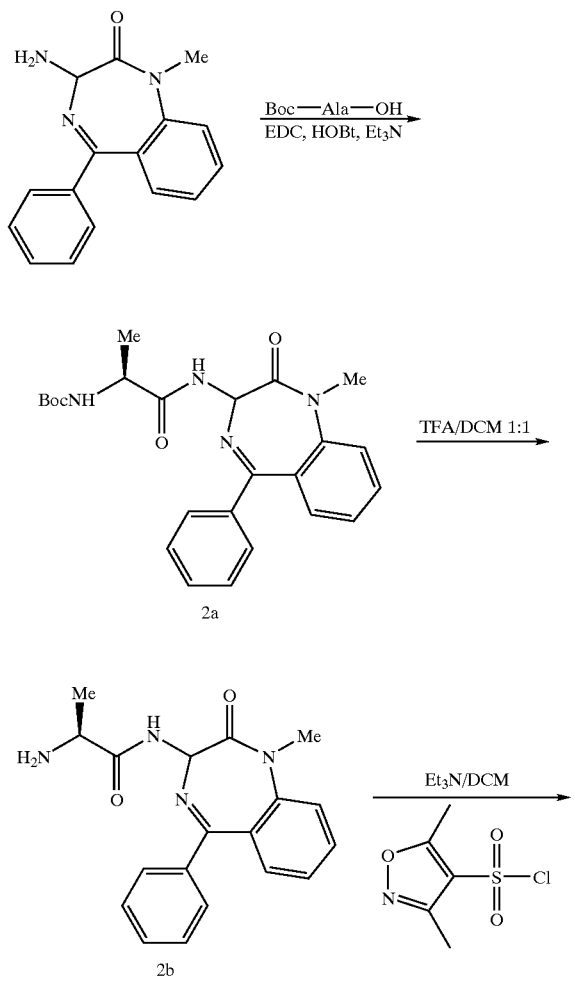

Example 2

Alternatively, compounds of Formula I can be prepared by the method of Scheme 2 which comprises a sequence of sulfonyl coupling, followed by deprotection, followed by amino acid coupling. In the method of Scheme 2, an amino acid derivative which has a protected carboxyl group, XV, is first coupled with a sulfonylating agent $(Q)SO_2Cl$, XIV, or an equivalent activated sulfonylating agent, to form a sulfonamide XVI. The carboxyl protecting group of XVI is removed using a standard deprotection method to give a sulfonamide carboxylic acid XVII. The W-X-Y-Z-substituted aminolactam, X, is then coupled with the sulfonamide carboxylic acid, XVII, to form a compound of Formula I.

Scheme 2

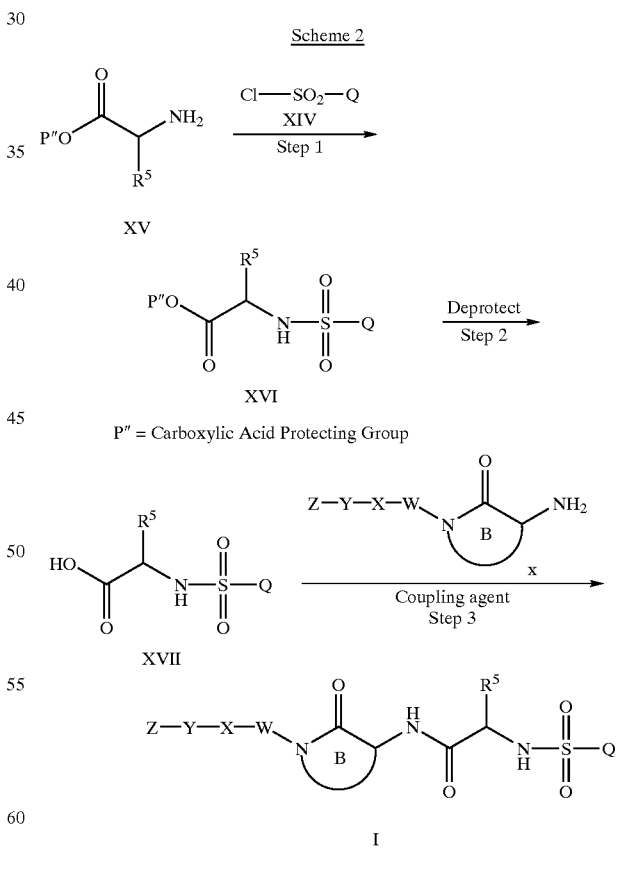

P″ = Carboxylic Acid Protecting Group

Methods for the synthesis of lactam intermediates as contemplated by the present invention useful in the synthesis of compounds of Formula (I), including amino benzodiazepinones, dibenzo azepinones and other related heterocycles, are known in the art and are disclosed in a number of references including PCT publication number WO 98/28268, WO 99/66934, WO 00/07995, and WO 00/38618, which are hereby incorporated by reference. Additional references include Bock, et al, J. Org. Chem., 1987, 52, 3232–3239; Sherrill et al, J. Org. Chem., 1995, 60, 730–734; and Walsh, D. A., Synthesis, September 1980, p.677; and Brown, et al., Tetrahedron Letters, 1971, 8, 667–670.

Synthetic approaches to substituted benzodiazepines are widely described in the literature. The typical methods are illustrated by, but are not limited to, the following references: M. G. Bock et al J. Org. Chem. 1987, 52, 3232. (b) R. G. Sherrill et al J. Org. Chem. 1995, 60, 734. (c) M. G. Bock et al J. Med. Chem. 1989, 32, 13–16. (d) J. L. Castro et al J. Med. Chem. 1997, 40, 2491–2501. (e) M. S. Chambers et al Bioorg. & Med. Chem. Lett. 1993, 3 (10), 1919–1924. (f) J. H. Gogerty et al J. Med. Chem. 1977, 20 (7), 952. (g) G. Semple et al Bioorg. & Med. Chem. Lett. 1996, 6(1), 51–54. (h) G. Semple et al J. Med. Chem. 1997, 40, 331–341. (i) G. Semple et al Bioorg. & Med. Chem. Lett. 1996, 6 (1), 55–58. (j) G. Semple et al Synth. Commun. 1996, 26 (4), 721–727. (k) G. A. Showell et al J. Med. Chem. 1994, 37, 719–721. General synthetic descriptions of 2-aminobenzophenone with various substitutions used in the preparation of benzodiaepines may be found in D. A. Walsh Synthesis 1980, 677.

Incorporation of alpha-alkoxy amino acids provides access to additional compounds. alpha-Alkoxy amino acid derivatives are available from a number of procedures available in the art. For instance, they may be synthesized by electrochemical oxidation of malonic acid half esters in alcoholic solvents as shown in Horikawa, Hiroshi; Iwasaki, Tameo; Matsumoto, Kazuo; Miyoshi, Muneji. A new synthesis of 2-alkoxy- and 2-acetoxy-2-amino acids by anodic oxidation. Tetrahedron Lett. 1976, (3), 191–4. Alternative procecures include alkoxide displacement of dichloroacetic acid to form an alpha-halo-alpha-alkoxyacetate, followed by aminolysis as reported in Gross, Hans; Gloede, Joerg; Freiberg, Juergen. alpha-Halo ethers. XXIX. Glyoxylic acid derivatives from chloromethoxyacetic acid or dichloroacetic acid. Ann. Chem., Justus Liebigs (1967), 702 68–74. and similar references.

An example of an L-α-amino-β-thio-ε-caprolactam, as shown in Scheme 3, where ring B is the amino lactam of XVIII and J is a sulfur atom has been reported in the literature. See S. A. Ahmed et al, FEBS Letters, (1984), vol. 174, pages 76–9. One skilled in the art can extend this methodology to the synthesis of β-amino and oxygen containing rings by analogy. The sulfur-containing molecules can also be oxidized to the sulfoxide and sulfone by methods known to one skilled in the art.

Scheme 3

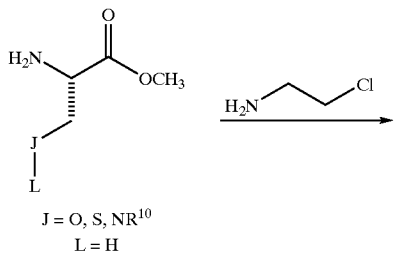

J = O, S, NR$^{10}$
L = H

-continued

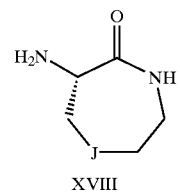

XVIII

Methods for the alkylation of lactams as contemplated by the present invention in lactam ring B in Formula (I), including amino benzodiazepines and other related heterocycles, are well known in the art. For example, Scheme 4 demonstrates that the lactam nitrogen of compound XIX or other lactam intermediates of the present invention can be alkylated by generating the anion with bases such as LDA, LiHMDS, lithium bis(trimethylsilyl) amide potassium carbonate or sodium hydride in solvents like THF, with or without cosolvents such as DMPU, HMPA or DMF, and reacting this with a variety of groups containing leaving groups (X") like bromide, iodide, mesylate or tosylate. Alkylating agents such as α-bromo amides, ketones and acids can be prepared by a number of literature methods including halogenation of amino acids by diazotization or are commercially available. Other suitable alkylating agents such as alkyl, allylic and benzylic halides can be formed form a variety of precursors such as free-radical addition of halides or activation of alcohols, and other chemistries known to those skilled in the art. For discussion of these types of reactions, see Carey, F. A. and Sundberg, R. J., Advanced Organic Chemistry, Part A, New York: Plenum Press, 1990, pages 304–305, 342–347, 695–698.

Scheme 4

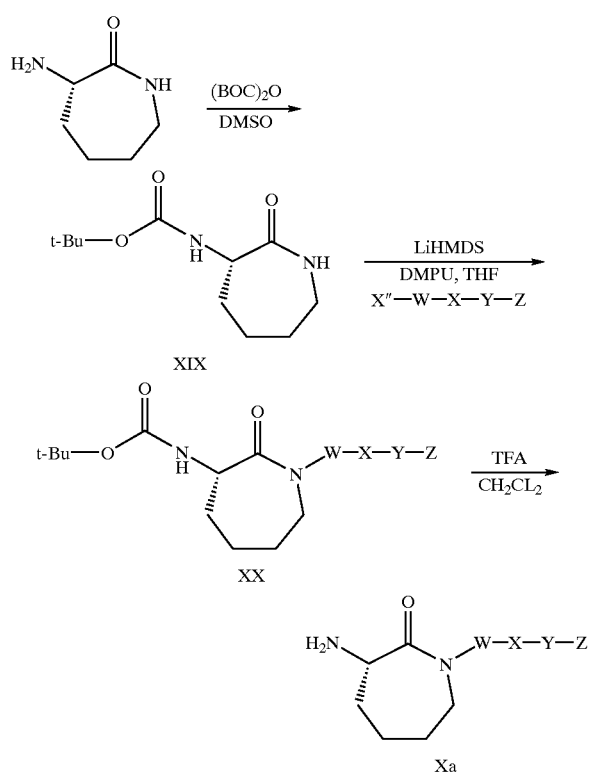

A variety of suitably protected natural and unnatural amino acid derivatives are commercially available or can be prepared by known procedures and can be coupled to the aminolactam of Ring B using standard coupling procedures. Representative procedures for preparation of amino acids include the Strecker amino acid synthesis; the Ugi 4-component coupling reaction; alkylation of glycine benzophenone imine, Seebach's method (reviewed in O'Donnell, Martin J.; Fang, Zhiqiang; Seebach's "Self-Regeneration of Chirality" and related methods for the synthesis of α-amino acids, Hecheng Huaxue (1996), 4(4), 303–316); Schollkopf's bislactam method, and many others. For a review, see Duthaler, Rudolf O. Recent developments in the stereoselective synthesis of α-amino acids. Tetrahedron (1994), 50(6), 1539–650.

Protection groups for amine funtional group can be prepared by methods well known in the literature for amino protecting groups as discussed in Theodora W. Greene's book "Protective Groups in Organic Synthesis", for example, N-Boc using di-t-butyldicarbonate in an appropriate solvent like DMSO. Other protecting groups for amino acids include but are not limited to Boc (tert-butyloxycarbonyl), Fmoc (Fluorenylmethyloxycarbonyl), cBz (Benzyloxycarbonyl), and Alloc (Allyoxycarbonyl). Methods for removing these protecting groups are known to those skilled in the art.

Suitable coupling agents include but are not limited to activating agents such as dicyclohexylcarbodiimide (DCC), diisopropylcarbodiimide (DICI), or 1-(3-dimethylaminopropyl)-3-ethylcarbodiimide (EDC) with or without the additive hydroxybenzotriazole (HOBt) or reagents such as HATU (O-(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate), which are used in a suitable solvent such as dichloromethane or N,N-dimethylformamide with a suitable base such as diisopropylethylamine, N-methylmorpholine, or triethylamine. Most preferably, the couplings are run using EDC and HOBt as coupling agents with triethylamine as a base in dichloromethane.

EXAMPLES

Chemical abbreviations used in the Examples are defined as follows:
"DMF" for dimethylformamide,
"THF" for tetrahydrofuran,
"DMPU" for 1,3-dimethyl-3,4,5,6-tetrahydro-2(1H)-pyrimidone,
"HMPA" for hexamethylphosphoramide,
"TBTU" for O-(1H-benzotriazol-1-yl)-N,N,N',N'-tetramethyluronium tetrafluoroborate, and
"BOP" for benzotriazol-1-yloxytris-(dimethylamino)phosphonium hexafluorophosphate.
"LDA" for lithium diisopropyl amide
"LiHMDS" for lithium hexamethyl disilazide or lithium bis(trimethylsilyl) amide.
"HPLC" is an abbreviation used herein for high pressure liquid chromatography. Compounds of the present invention are generally purified by HPLC using conditions known to one skilled in the art. However, unless otherwise indicated, the following conditions are generally applicable. Reverse-phase HPLC can be carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). Alternatively, reverse-phase HPLC can be carried out using a Vydac C-18 column with gradient elution from 10% to 90% acetonitrile in water.

Example 1

2-(3,5-Dimethyl-isoxazole-4-sulfonylamino)-4-methyl-pentanoic Acid (1-Methyl-2-oxo-5-phenyl-2,3-dihydro-1H-benzo[e][1,4]diazepin-3-yl)-amide Step (1a). A solution of 1.2 g (3.46 mmol) of 3-Amino-1-methyl-5-phenyl-1,3-dihydro-benzo[e][1,4]diazepin-2-one and 0.818 g (3.53 mmol) of N-Boc-(L)-leucine dissolved in 50 mL of dichloromethane at 0° C. was treated sequentially with 1.2 mL (8.65 mmol) of triethylamine, 1.06 g (6.92 mmol) of hydroxybenzotriazole, and 0.827 g (4.32 mmol) of EDC. The cooling bath was removed and the solution was stirred for 2 h while warming to rt. The reaction solution was then diluted with 20 mL of water and the organic layer was separated and washed with 30 mL of 1 N HCl solution, 30 mL of a saturated NaHCO$_3$ solution, then dried over Na$_2$CO$_3$ and concentrated in vacou. Chromatography eluting with a gradient of 20 to 50% ethyl acetate in hexanes provided the desired product 1a. MS (ESI) M+H=479.4.

Step (1b). The purified material 1a was dissolved in 50 mL of a 1:1 solution of dichloroemethane and trifluoroacetic acid and stirred for 2 h at rt. The solution was directly concentrated and redissolved in 10 mL of toluene. After removal of the solvent 600 mg (35% for 2 steps) of the desired amine was isolated as its TFA salt, MS (ESI) M+H=379.4. This material was then freebased by dissolving in 20 mL of dichloromethane followed by extracting 3× with 10 mL of a saturated NaHCO$_3$ solution, followed by drying the dichloromethane solution with Na$_2$SO$_4$ and concentrating to the free amine 1b.

Step (1c). The free amine 1b 200 mg, 0.528 mmol) was dissolved in 20 mL of dichloromethane and 147 microliters (1.05 mmol) of triethylamine was added followed by 124 mg (0.63 mmol) of 3,5-dimethyl-isoxazole-4-sulfonyl chloride. After stirring 18 h at rt, 10 mL of water was added and the organic layer was separated. The organic layer was washed with 10 mL of 1 N HCl, 10 mL of a saturated NaHCO$_3$ solution, and 10 mL of brine. The organic layer was then dried over Na$_2$SO$_4$ and concentrated to an oil. Chromatography eluting with a gradient of 20 to 100% ethyl acetate in hexanes allowed the purification of 80 mg (28% yield) of the two diastereomers of the compound of Example 1. MS (ESI) M+H=538.3).

Example 2

2-(3,5-Dimethyl-isoxazole-4-sulfonylamino)-N-(1-methyl-2-oxo-5-phenyl-2,3-dihydro-1H-benzo[e][1,4]diazepin-3-yl)-propionamide Step (2a). The compound of Example 2a was synthesized in a manner similar to that of the compound of Example (1a), but using N-Boc-L-Alanine as the amino acid in 50% yield. MS (ESI) M+H=437.3.

Step (2b). The purified material 2a (1.0 g) was dissolved in 50 mL of a 1:1 solution of dichloromethane and trifluoroacetic acid and stirred for 2 h at rt. The solution was directly concentrated and redissolved in 10 mL of toluene. After removal of the solvent the material was then freebased by dissolving in 20 mL of dichloromethane followed by extracting 3× with 10 mL of a saturated NaHCO$_3$ solution. The dichloromethane solution was dried with Na$_2$SO$_4$ and concentrated to 0.75 g (96%) of the free amine 2b. MS (ESI) M+H=337.2).

Step (2c). The free amine 2b 100 mg, 0.29 mmol) was dissolved in 10 mL of dichloromethane and 83 microliters (0.6 mmol) of triethylamine was added followed by 70 mg (0.36 mmol) of 3,5-dimethyl-isoxazole-4-sulfonyl chloride. After stirring 18 h at rt, 10 mL of water was added and the organic layer was separated. The organic layer was washed with 10 mL of 1 N HCl, 10 mL of a saturated NaHCO$_3$ solution, and 10 mL of brine. The organic layer was then dried over Na$_2$SO$_4$ and concentrated to an oil. Chromatography eluting with a gradient of 20 to 50% ethyl acetate in hexanes allowed the purification of 30 mg (20% yield) of the compound of Example 2. MS (ESI) M+H=496.2.

Example 3

2-(3-Bromo-5-chloro-thiophene-2-sulfonylamino)-4-methyl-pentanoic Acid (1-Methyl-2-oxo-5-phenyl-2,3-dihydro-1H-benzo[e][1,4]diazepin-3-yl)-amide The compound of Example 3 was synthesized in a manner similar to that of the compound of Example 1, but using N-Boc-L-Alanine as the amino acid in Step (1a) and using 3-bromo-5-chloro-thiophene-2-sulfonyl chloride in Step (1c). MS (ESI) M+H=597.0.

Examples 4–47.

Additional Examples 4–47, listed below in Table 1, were synthesized by the following procedure: A solution of the free amine 1b from step (1b) (4.5 mg, 12 micromoles) was dissolved in 0.5 mL of dichloromethane and 3.3 microliters of triethylamine (25 micromoles) was added, followed by 14 micromoles of a corresponding sulfonyl chloride. After stirring for 24 h at room temperature, 100 mg of a mixture of sulfonic acid derived silica gel and aminopropyl derived silica gel was added with an additional 0.5 mL of dichloromethane. After stirring for 24 h at room temperature, the solution was collected and concentrated. HPLC eluting with a gradient of from 10 to 100% acetonitrile/water provided purified compounds, in a range of from 0.1 to 5 mg each.

Example 4

2-(Naphthalene-1-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=569.3

Example 5

2-(5-Dimethylamino naphthalene-1-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=612.4

Example 6

2-(Naphthalene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=569.3

Example 7

2-(2-Acetamido-4-methylthiazole-5-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=597.3

Example 8

2-(Thiophene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=525.3

Example 9

2-(Quinoline-8-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=570.3

Example 10

2-(Phenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=519.3

Example 11

2-(2,5-Dichlorophenyl sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=588.1

Example 12

2-(Mesitylene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=561.3

Example 13

2-(3-Nitrophenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=564.2

Example 14

2-(4-Bromophenyl-sulfonylamino)-4-methyl-pentanoic Acid (1-methyl-2-oxo-5-phenyl-2,3-dihydro-1H-benzo[e][1,4]diazepin-3-yl)-amide. MS (ESI) M+H=598.1

Example 15

2-(4-Fluorophenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=537.2

Example 16

2-(4-Chlorophenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=553.7

Example 17

2-(4-Acetamidophenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=576.3

Example 18

2-(4-Nitrophenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=564.2

Example 19

2-(4-Methoxyphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=549.2

Example 20

2-(4-tert-Butylphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=575.3

Example 21

2-(p-Toluene-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=533.2

Example 22

2-(Benzyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=533.2

Example 23

2-(Beta-styrene-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=545.3

Example 24

2-((2-Methoxycarbonyl)phenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=577.3

Example 25

2-(2-Nitro-4-(trifluoromethyl)phenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=633.2

Example 26

2-(3-(Trifluoromethyl)phenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=587.2

Example 27

2-(2,5-Dimethoxyphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=579.3

Example 28

2-(2-Methylphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=533.2

Example 29

2-(3,4-Dichlorophenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=588.1

Example 30

2-(4-(Trifluoromethoxy)phenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=603.2

Example 31

2-(3,4-Dimethoxyphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=579.3

Example 32

2-(2-Bromophenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=598.1

Example 33

2-(3,5-bis(Trifluoromethyl)phenyl-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=655.3

Example 34

2-(4-Ethylphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=547.3

Example 35

2-(4-Isopropylphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=561.3

Example 36

2-(2,5-Dichlorothiophene-3-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=594.1

Example 37

2-(5-Chlorothiophene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=559.7

Example 38

2-(2-(Trifluoromethyl)phenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=587.2

Example 39

2-(3-Methylphenyl-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=533.2

Example 40

2-(2,3-Dichlorothiophene-5-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=594.1

Example 41

2-(4-Bromo-5-chlorothiophene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=639.3

Example 42

2-(5-[(Benzoylamino)methyl]-thiophene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=658.3

Example 43

2-(4-Phenylsulfonylthiophene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=665.4

Example 45

2-(5-(Phenylsulfonyl)thiophene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=665.4

Example 46

2-[2-(1-Methyl-(5-trifluoromethyl)pyrazole)thiophene-5-sulfonylamino]-4-methyl-pentanoic Acid (1-Methyl-2-oxo-5-phenyl-2,3-dihydro-1H-benzo[e][1,4]diazepin-3-yl)-amide MS (ESI) M+H= 673.4

Example 47

2-(5-(2-Pyridyl)thiophene-2-sulfonylamino)-4-methyl-pentanoic Acid (1-Methyl-2-oxo-5-phenyl-2,3-dihydro-1H-benzo[e][1,4]diazepin-3-yl)-amide. MS (ESI) M+H=602.4

Tables 1 below provides representative Examples of the compounds of Formula (I) of the present invention.

TABLE 1

| Ex.# | R—SO$_2$— | MassSpec (ESI, M + H) Found |
|---|---|---|
| 3 | 3-bromo-5-chloro-2-thiophene-SO$_2$— | 597.0 |
| 4 | 1-naphthalene-SO$_2$— | 569.3 |
| 5 | 5-dimethylamino-naphthalene-1-SO$_2$— | 612.4 |
| 6 | 2-naphthalene-SO$_2$— | 569.3 |
| 7 | 2-acetamido-4-methyl-5-thiazole-SO$_2$— | 597.3 |
| 8 | 2-thiophene-SO$_2$— | 525.3 |
| 9 | 8-quinoline-SO$_2$— | 570.3 |
| 10 | phenyl-SO$_2$— | 519.2 |
| 11 | 2,5-dichlorophenyl-SO$_2$— | 588.1 |
| 12 | 1,3,5-trimethylphenyl-SO$_2$— | 561.3 |
| 13 | 3-nitrophenyl-SO$_2$— | 564.2 |
| 14 | 4-bromophenyl-SO$_2$— | 598.1 |
| 15 | 4-fluorophenyl-SO$_2$— | 537.2 |
| 16 | 4-chlorophenyl-SO$_2$— | 553.7 |
| 17 | 4-acetamidophenyl-SO$_2$— | 576.3 |
| 18 | 4-nitrophenyl-SO$_2$— | 564.2 |
| 19 | 4-methoxyphenyl-SO$_2$— | 549.2 |
| 20 | 4-tert-butylphenyl-SO$_2$— | 575.3 |
| 21 | 4-methylphenyl-SO$_2$— | 533.2 |
| 22 | benzyl-SO$_2$— | 533.2 |
| 23 | beta-styrene-SO$_2$— | 545.3 |
| 24 | 2-methoxycarbonylphenyl-SO$_2$— | 577.3 |
| 25 | 2-nitro-4-(trifluoromethyl)phenyl-SO$_2$— | 632.2 |
| 26 | 3-(trifluoromethyl)phenyl-SO$_2$— | 587.2 |
| 27 | 2,5-dimethoxyphenyl-SO$_2$— | 579.3 |
| 29 | 2-methylphenyl-SO$_2$— | 533.2 |
| 29 | 3,4-dichlorophenyl-SO$_2$— | 588.1 |
| 30 | 4-(trifluoromethoxy)phenyl-SO$_2$— | 603.2 |

TABLE 1-continued

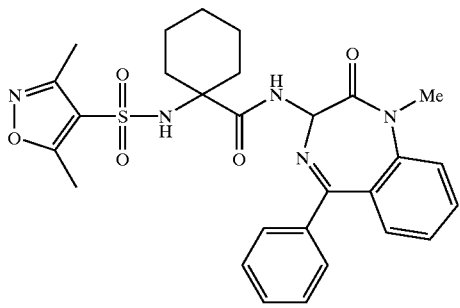

| Ex.# | R—SO₂— | MassSpec (ESI, M + H) Found |
|---|---|---|
| 31 | 3,4-dimethoxyphenyl-SO₂— | 579.3 |
| 32 | 2-bromophenyl-SO₂— | 598.1 |
| 33 | 3,5-bis(trifluoromethyl)phenyl-SO₂— | 655.3 |
| 34 | 4-ethylphenyl-SO₂— | 547.3 |
| 35 | 4-isopropylphenyl-SO₂— | 561.3 |
| 36 | 2,5-dichlorothiophene-3-SO₂— | 594.1 |
| 37 | 5-chlorothiophene-2-SO₂— | 559.7 |
| 38 | 2-(trifluoromethyl)phenyl-SO₂— | 587.2 |
| 39 | 3-methylphenyl-SO₂— | 533.2 |
| 40 | 2,3-dichlorothiophene-5-SO₂— | 594.1 |
| 41 | 4-bromo-5-chlorothiophene-2-SO₂— | 639.3 |
| 42 | 5-[(benzoylamino)methyl]-2-SO₂— | 658.3 |
| 43 | 4-phenylsulfonylthiophene-2-SO₂— | 665.4 |
| 45 | 5-(phenylsulfonyl)thiophene-2-SO₂— | 665.4 |
| 46 | 2(1-methyl-(5-trifluoromethyl)pyrazole)thiophene-5-SO₂— | 673.4 |
| 47 | 5-(2-pyridyl)thiophene-2-SO₂— | 602.4 |

Example 48

1-(3,5-Dimethyl-isoxazole-4-sulfonylamino)-cyclohexanecarboxylic Acid (1-Methyl-2-oxo-5-phenyl-2,3-dihydro-1H-benzo[e][1,4]diazepin-3-yl)-amide

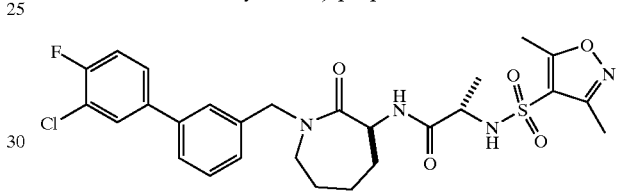

(48a) 1-Aminocyclohexanecarboxylic acid (1.5 grams, 10.5 mmol) was dissolved in 12.5 mL of a 1N solution of sodium hydroxide, 6 mL of water, and 6 mL of tetrahydrofuran. To this solution 3,5-dimethyl-isoxazole-4-sulfonyl chloride (2.45 g, 12.6 mmol) was added and the solution was stirred at rt for 16 hours. A sufficient portion of 1N NaOH was then added to return the solution to a pH of 9 or higher, and the reaction solution was extracted 2× with a 25 mL portion of dichloromethane and the combined organic layers were discarded. The aqueous layer was then acidified with 1N HCl until the pH was 3 or lower, and the aqueous layer was extracted 3× with dichloromethane. The organic layers were dried with magnesium sulfate and concentrated to a white solid 48a which was used without further purification (234 mg, 7.4%). Step (48b) The crude acid 48a (199 mg, 0.66 mg) was dissolved in 8 mL of CH₂Cl₂ and treated with 0.25 mL(1.5 mmol) of diisopropylethylamine. The reaction solution was cooled to 0° C. and stirred for 5 min. To the reaction mixture was added 1-hydroxybenzotriazole (162 mg, 1.2 mmol) and HATU (285 mg, 0.75 mmol), and this mixture was stirred for 5 min. A 300 mg (0.60 mmol) portion of of 3-Amino-1-methyl-5-phenyl-1,3-dihydro-benzo[e][1,4]diazepin-2-one was then added and the reaction solution was allowed to warm to rt and stirred for 16 h. The reaction was quenched with 10 mL of water, and the layers were separated. The organic layer was rinsed with 10% citric acid, 1N Na OH, brine and then concentrated. The resulting oil was dissolved in ethyl acetate, washed with water (6×50 mL) and dried over sodium sulfate. After filtration and concentration the compound of Example 48 was obtained as a pale yellow solid 48 (125 mg, 38%), MS (API, MS (M+H)⁺=551.

Example 49

N-[1-(3'-Chloro-4'-fluoro-biphenyl-3-ylmethyl)-2-oxo-azepan-3-yl]-2-(3,5-dimethyl-isoxazole-4-sulfonylamino)-propionamide Step (49a) Di-tert-butyldicarbonate (10.2 g, 46.7 mmoles) was added portion wise to a solution of L-(–)-α-amino-ε-caprolactam (5.0 g, 39.0 mmoles) in dimethyl sulfoxide (30 mL). After 5 h at rt, the reaction was partitioned between water (100 mL) and ethyl acetate. The combined organic extracts were washed successively with 1 M HCl (50 mL), brine, and dried (MgSO₄) and concentrated in vacuo. The residue was recrystallized in 1:1 v/v ether-hexanes, 2 crops yielded the desired product (6.26 g, 70%) as white solid 49a. MS (M+H-BOC)+=129.

Step (49b) Boc-caprolactam 49a (5.0 g , 21.9 mmol) was dissolved in 60 mL of THF and chilled to −78° C. To the chilled solution was added 24 mL of a 1.0 M solution of lithium bis(trimethylsilyl)amide in THF, and the solution was brought to 0° C. and stirred for 15 min. To the anion solution was added 6.5 g (22 mmol) of 3-iodobenzyl bromide (Aldrich) and the the solution was allowed to warm to rt and stirred for 18 h. The reaction solution was diluted with 50 mL of water and extracted 3× with ethyl acetate. The combined organic layers were dried over MgSO₄ and concentrated in vacuo. The crude product was purified by chromatography eluting with a gradient of 5–20% ethyl acetate/hexanes to afford 7.0 g (72%) of the alkylated Boc-protected caprolactam as a white solid 49b. MS (M+Na)⁺=467.

Step (49c) The caprolactam 49b (1.1 g, 2.47 mmol) was dissolved in 20 mL of a 50% solution of trifluoroacetic acid in dichloromethane. After 2 h at rt, the solution was concentrated to an oil. The oil was then dissolved in 50 mL of dichloromethane and chilled to 0° C. Boc-L-Alanine (0.47 g, 2.5 mmol) was then added, followed by 1-hydroxybenzotriazole (0.75 g, 4.94 mmol), EDC (0.6 g, 3.0 mmol) and triethylamine (0.86 mL, 6.2 mmol). After 16 h at rt the reaction solution was diluted with 50 mL of 1 N HCl and the aqueous layer was extracted with 2 30 mL portions of dichloromethane. The organic layers were combined, dried and concentrated and the residual oil was purified by chromatography eluting with a gradient of 20–40% ethyl acetate/hexanes to afford 1.2 g (93%) of the desired caprolactam 49c. MS (ESI,M+Na$^+$)=538.2.

Step (49d) The caprolactam 49c (600 mg, 1.16 mmol) was dissolved in 20 mL of toluene and 2 mL of methanol. 4-Fluoro-3-chlorophenylboronic acid (304 mg, 1.5 mmol) was then added followed by tris(dibenzylideneaccetone) dipalladium (180 mg, 0.17 mmol), triphenylphosphine (184 mg, 0.7 mmol) and 1 mL of a 1M solution of potassium carbonate. The reaction solution was heated to reflux for 16 h and allowed to cool. The reaction solution was then partitioned between 25 mL of ethyl acetate and 25 mL of brine and the organic layer was removed. The aqueous layer was extracted with 2 additional 10 mL portions of ethyl acetate and the combined organic layers were dried and concentrated to an oil. Chromatography eluting with a gradient of 1:5 to 2:5 ethyl acetate/hexanes provided the desired biaryl caprolactam (500mg, 83%) as a white solid 49d. MS (ESI,M+Na$^+$)=540.3.

Step (49e) The biaryl caprolactam 49d (0.2 g, 0.39 mmol) was dissolved in 20 mL of a 50% solution of trifluoroacetic acid in dichloromethane. After 2 h at rt, the solution was concentrated to an oil. The oil was then dissolved in 10 mL of dichloromethane and 108 μL of triethylamine (0.772 mmol) and 91 mg of 3,5-dimethylisoxazole-4-sulfonyl chloride were added. The reaction solution was stirred at rt for 18 h, and then diluted with 10 mL of water and extracted with 2 10 mL portions of dichloromethane. The organic layers were dried and concentrated, and the residual oil was purified by chromatography eluting with 5% methanol in dichloromethane to afford 130 mg (63%) of the compound of Example 49 as a white solid 49. MS (ESI,M+Na$^+$) =623.4.

Example 50

2-(3,5-Dimethyl-isoxazole-4-sulfonylamino)-N-[5-(4-fluoro-phenyl)-1-methyl-2-oxo-2,3-dihydro-1H-benzo[e][1,4]diazepin-3-yl]-propionamide Step (50a): {1-[5-(4-Fluoro-phenyl)-1-methyl-2-oxo-2,3-dihydro-1H-benzo[e][1,4]diazepin-3-ylcarbamoyl]-ethyl}-carbamic Acid tert-Butyl Ester.

The compound of 50a was synthesized in a procedure analogous to the synthesis of the compound of 1a using 0.5 g of 3-Amino-5-(4-fluoro-phenyl)-1-methyl-1,3-dihydro-benzo[e][1,4]diazepin-2-one, and N-Boc-(L)-alanine. In 88% yield.

Step (50b): 2-Amino-N-[5-(4-fluoro-phenyl)-1-methyl-2-oxo-2,3-dihydro-1H-benzo[e][1,4]diazepin-3-yl]-propionamide.

The compound of 50b was deprotected using a procedure analogous to the synthesis of the compound of 2b but using the compound from 50a and was carried forward without purification.

Step (50c): The compound of Example 50 was synthesized from the compound of 50b in a procedure analogous to the synthesis of the compound of 2b using 3,5-dimethyl isoxazole-4-sulfonyl chloride in 31% yield. MS (ESI) M+H=514.2.

Example 51

2-2-(3,5-Dimethyl-isoxazole-4-sulfonylamino)-4-methyl-pentanoic Acid [5-(4-Fluoro-phenyl)-1-methyl-2-oxo-2,3-dihydro-1H-benzo[e][1,4]diazepin-3-yl]-amide Step (51a): {1-[5-(4-Fluoro-phenyl)-1-methyl-2-oxo-2,3-dihydro-1H-benzo[e][1,4]diazepin-3-ylcarbamoyl]-3-methyl-butyl}-carbamic Acid tert-Butyl Ester.

The compound of 51a was synthesized in a procedure analogous to the synthesis of the compound of 1a using 0.5 g of 3-Amino-5-(4-fluoro-phenyl)-1-methyl-1,3-dihydro-benzo[e][1,4]diazepin-2-one, and (L)-leucine. In 92% yield.

Step (51b): 2-Amino-4-methyl-pentanoic Acid [5-(4-fluoro-phenyl)-1-methyl-2-oxo-2,3-dihydro-1H-benzo[e][1,4]diazepin-3-yl]-amide.

The compound of 51b was deprotected using a procedure analogous to the synthesis of the compound of 2b but using the compound from 51a and was carried forward without purification.

Step (51c): The compound of Example 51 was synthesized from the compound of 50b in a procedure analogous to the synthesis of the compound of 2b using 3,5-dimethyl isoxazole-4-sulfonyl chloride in 36% yield. MS (ESI) M+H=556.2.

Example 52

2-(2-Fluoro-benzenesulfonylamino)-N-[5-(4-fluoro-phenyl)-1-methyl-2-oxo-2,3-dihydro-1H-benzo[e][1,4]diazepin-3-yl]-propionamide Step (52a): [1-(1-Methyl-2-oxo-5-phenyl-2,3-dihydro-1H-benzo[e][1,4]diazepin-3-ylcarbamoyl)-ethyl]-carbamic acid tert-butyl ester.

The compound of 52a was synthesized in a procedure similar to that of the compound of 1a but using N-Boc-(L)-alanine as the amino acid in 94% yield.

Step (52b): 2-Amino-N-(1-methyl-2-oxo-5-phenyl-2,3-dihydro-1H-benzo[e][1,4]diazepin-3-yl)-propionamide.

The compound of 52b was deprotected using a procedure analogous to the synthesis of the compound of 2b but using the compound from 52a and was carried forward without purification.

Step (52c): The compound of Example 52 was synthesized from the compound of 52b in a procedure analogous to the synthesis of the compound of 2b using 2-fluorobenzene sulfonyl chloride in 68% yield. MS (ESI) M+H=495.2.

Example 53

N-(1-Methyl-2-oxo-5-phenyl-2,3-dihydro-1H-benzo[e][1,4]diazepin-3-yl)-2-(2-trifluoromethyl-benzenesulfonylamino)-propionamide The compound of Example 53 was synthesized in a procedure analogous to the synthesis of the compound of Example 52 using 2-trifluoromethyl benzene sulfonyl chloride in 68% yield. MS (ESI) M+H=545.2

Example 54

2-(2-Fluoro-benzenesulfonylamino)-4-methyl-pentanoic Acid (1-Methyl-2-oxo-5-phenyl-2,3-dihydro-1H-benzo[e][1,4]diazepin-3-yl)-amide The compound of Example 54 was synthesized in a procedure analogous to the synthesis of the compound of Example 1 using the intermediate from 1b and 2-fluorobenzene sulfonyl chloride in 70% yield. MS (ESI) M+H=537.2

Example 55

4-Methyl-2-(2-trifluoromethyl-benzenesulfonylamino)-pentanoic Acid (1-Methyl-2-oxo-5-phenyl-2,3-dihydro-1H-benzo[e][1,4]diazepin-3-yl)-amide The compound of Example 55 was synthesized in a procedure analogous to the synthesis of the compound of Example 1 using the intermediate from 1b and 2-trifluoromethylbenzene sulfonyl chloride in 65% yield. MS (ESI) M+H=587.2

Example 56

4-Methyl-2-(propane-1-sulfonylamino)-pentanoic Acid (1-methyl-2-oxo-5-phenyl-2,3-dihydro-1H-benzo[e][1,4]diazepin-3-yl)-amide The compound of Example 56 was synthesized in a procedure analogous to the synthesis of the compound of Example 1 using the intermediate from 1b and 1-propanesulfonyl chloride in 16% yield. MS (ESI) M+H= 485.2

Example 57

4-Methyl-2-(propane-1-sulfonylamino)-pentanoic Acid (1-Methyl-2-oxo-5-phenyl-2,3-dihydro-1H-benzo[e][1,4]diazepin-3-yl)-amide The compound of Example 57 was synthesized in a procedure analogous to the synthesis of the compound of Example 1 using the intermediate from 1b and 1-butanesulfonyl chloride. The compound was purified by reverse-phase HLC and isolated in 1% yield. MS (ESI) M+H =499.2

Example 58

2-(3,5-Dimethyl-isoxazole-4-sulfonylamino)-N-[-1-methyl-2-oxo-5-(4-trifluoromethyl-phenyl)-2,3-dihydro-1H-benzo[e][1,4]diazepin-3-yl]-propionamide Step (58a): {1-[1-Methyl-2-oxo-5-(4-trifluoromethyl-phenyl)-2,3-dihydro-1H-benzo[e][1,4]diazepin-3-ylcarbamoyl]-ethyl}-carbamic Acid tert-Butyl Ester.

The compound of 58a was synthesized in a procedure analogous to the synthesis of the compound of 1a using 0.5 g of 3-Amino-1-methyl-5-(4-trifluoromethyl-phenyl)-1,3-dihydro-benzo[e][1,4]diazepin-2-one, and N-Boc-(L)-alanine. In 75% yield.
Step (58b): 3-Amino-1-methyl-5-(4-trifluoromethyl-phenyl)-1,3-dihydro-benzo[e][1,4]diazepin-2-one.

The compound of 58b was deprotected using a procedure analogous to the synthesis of the compound of 2b but using the compound from 58a and was carried forward without purification.
Step (58c): The compound of Example 58 was synthesized from the compound of 58b in a procedure analogous to the synthesis of the compound of 2b using 3,5-dimethyl isoxazole-4-sulfonyl chloride in 50% yield. MS (ESI) M+H=564.2.

Example 59

2-(3,5-Dimethyl-isoxazole-4-sulfonylamino)-4-methyl-pentanoic Acid (7-Chloro-1-methyl-2-oxo-5-phenyl-2,3-dihydro-1H-benzo[e][1,4]diazepin-3-yl)-amide Step (59a): [1-(7-Chloro-1-methyl-2-oxo-5-phenyl-2,3-dihydro-1H-benzo[e][1,4]diazepin-3-ylcarbamoyl)-3-methyl-butyl]-carbamic Acid tert-Butyl Ester.

The compound of 59a was synthesized in a procedure analogous to the synthesis of the compound of 1a using 0.4 g of 3-Amino-7-chloro-1-methyl-5-phenyl-1,3-dihydro-benzo[e][1,4]diazepin-2-one, and N-Boc-(L)-valine. In 93% yield.

Step (59b): 2-Amino-4-methyl-pentanoic Acid (7-chloro-1-methyl-2-oxo-5-phenyl-2,3-dihydro-1H-benzo[e][1,4]diazepin-3-yl)-amide.

The compound of 59b was deprotected using a procedure analogous to the synthesis of the compound of 2b but using the compound from 59a and was carried forward without purification.
Step (59c): The compound of Example 59 was synthesized from the compound of 59b in a procedure analogous to the synthesis of the compound of 2b using 3,5-dimethyl isoxazole-4-sulfonyl chloride in 50% yield. MS (ESI) M+H=572.2.

Example 60

4-Methyl-2-(propane-1-sulfonylamino)-pentanoic Acid [5-(4-Chloro-phenyl)-1-methyl-2-oxo-2,3-dihydro-1H-benzo[e][1,4]diazepin-3-yl]-amide Step (60a): {1-[5-(4-Chloro-phenyl)-1-methyl-2-oxo-2,3-dihydro-1H-benzo[e][1,4]diazepin-3-ylcarbamoyl]-3-methyl-butyl}-carbamic Acid tert-Butyl Ester.

The compound of 60a was synthesized in a procedure analogous to the synthesis of the compound of 1a using 15.0 g of 3-Amino-5-(4-chloro-phenyl)-1-methyl-1,3-dihydro-benzo[e][1,4]diazepin-2-one and N-Boc-(L)-valine. in 53% yield.
Step (60b): 2-Amino-4-methyl-pentanoic Acid [5-(4-chloro-phenyl)-1-methyl-2-oxo-2,3-dihydro-1H-benzo[e][1,4] diazepin-3-yl]-amide.

The compound of 60b was deprotected using a procedure analogous to the synthesis of the compound of 2b but using the compound from 60a and was carried forward without purification.
Step (60c): The compound of Example 60 was synthesized from the compound of 60b in a procedure analogous to the synthesis of the compound of 2b using 1-propanesulfonyl chloride in 80% yield. MS (ESI) M+H=519.2.

Example 61

2-(3,5-Dimethyl-isoxazole-4-sulfonylamino)-4-methyl-pentanoic Acid (1-Methyl-2-oxo-5-pyridin-2-yl-2,3-dihydro-1H-benzo[e][1,4]diazepin-3-yl)-amide Step (61a): [3-Methyl-1-(1-methyl-2-oxo-5-pyridin-2-yl-2,3-dihydro-1H-benzo[e][1,4]diazepin-3-ylcarbamoyl)-butyl]-carbamic Acid tert-Butyl Ester.

The compound of Example 61a was synthesized in a procedure analogous to the synthesis of the compound of Example 1a using 0.31 g of 3-Amino-1-methyl-5-pyridin-2-yl-1,3-dihydro-benzo[e][1,4]diazepin-2-one and N-Boc-(L)-valine. in 50% yield.
Step (61b): 2-Amino-4-methyl-pentanoic Acid (1-Methyl-2-oxo-5-pyridin-2-yl-2,3-dihydro-1H-benzo[e][1,4]diazepin-3-yl)-amide.

The compound of Example 61b was deprotected using a procedure analogous to the synthesis of the compound of Example 2b but using the compound from 61a and was carried forward without purification.
Step (61c): The compound of Example 61 was synthesized from the compound of Example 61b in a procedure analogous to the synthesis of the compound of Example 2b using 3,5-dimethyl isoxazole-4-sulfonyl chloride in 39% yield. MS (ESI) M+H=539.2.

Example 62

2-[(3,5-Dimethyl-isoxazole-4-sulfonyl)-methyl-amino]-N-(1-methyl-2-oxo-5-phenyl-2,3-dihydro-1H-benzo[e][1,4]diazepin-3-yl)-propionamide The compound from Example 60 (0.02 g) was dissolved in methanol and treated with excess trimethylsilyldiazomethane until a yellow color persisted. The residual reagent was destroyed with acetic acid and the solution was concentrated to provide the compound of Example 63 in 100% yield. MS (ESI) M+H=510.2.

Example 63

3-Dimethylamino-2-(3,5-dimethyl-isoxazole-4-sulfonylamino)-N-(1-Methyl-2-oxo-5-phenyl-2,3-dihydro-1H-benzo[e][1,4]diazepin-3-yl)-propionamide Step (63a): [2-Chloro-1-(1-methyl-2-oxo-5-phenyl-2,3-dihydro-1H-benzo[e][1,4]diazepin-3-ylcarbamoyl)-ethyl]-carbamic Acid tert-Butyl Ester.

The compound of 63a was synthesized in a procedure analogous to the synthesis of the compound of 1a using 0.26 g of 3-Amino-1-methyl-5-phenyl-1,3-dihydro-benzo[e][1,4]diazepin-2-one and N-Boc-(L)-•-chloroalanine in 11% yield. MS (ESI) M+Na=457.3.

Step (63b): [2-Dimethylamino-1-(1-methyl-2-oxo-5-phenyl-2,3-dihydro-1H-benzo[e][1,4]diazepin-3-ylcarbamoyl)-ethyl]-carbamic Acid tert-Butyl Ester.

The compound from 63a (50 mg, 0.1 mmol) was dissolved in 5 mL of acetonitrile and treated with 0.5 mL of 40% dimethylamine in water. The reaction solution was stirred at rt for 2 h and concentrated to provide the compound of 63b in 100% yield. MS (ESI) M+H=480.3.

Step (63c): 2-Amino-3-dimethylamino-N-(1-methyl-2-oxo-5-phenyl-2,3-dihydro-1H-benzo[e][1,4]diazepin-3-yl)-propionamide.

The compound of 63c was deprotected using a procedure analogous to the synthesis of the compound of 2b but using the compound from 63b and was carried forward without purification.

Step (63d): The compound of Example 63 was synthesized from the compound of 61c in a procedure analogous to the synthesis of the compound of 2b using 3,5-dimethyl isoxazole-4-sulfonyl chloride in 50% yield. MS (ESI) M+H=539.2.

Example 64

N-[1-Methyl-2-oxo-5-(4-trifluoromethyl-phenyl)-2,3-dihydro-1H-benzo[e][1,4]diazepin-3-yl]-2-(propane-1-sulfonylamino)-propionamide The compound of Example 64 was synthesized from 0.1 g of the compound of 58b in a procedure analogous to the synthesis of the compound of 2b using 1-propanesulfonyl chloride in 50% yield. MS (ESI) M+H=511.2.

Example 65

N-(7-Chloro-1-methyl-2-oxo-5-phenyl-2,3-dihydro-1H-benzo[e][1,4]diazepin-3-yl)-2-(3,5-dimethyl-isoxazole-4-sulfonylamino)-propionamide The compound of Example 65 was synthesized using a procedure analogous to the synthesis of the compound of Example 59 but using N-Boc-(L)-alanine in the second step. MS (ESI) M+H=530.1.

Example 66

2-(3,5-Dimethyl-isoxazole-4-sulfonylamino)-4-methyl-pentanoic Acid [5-(4-Chloro-phenyl)-1-methyl-2-oxo-2,3-dihydro-1H-benzo[e][1,4]diazepin-3-yl]-amide The compound of Example 66 was synthesized from 10 g of the compound of 60b in a procedure analogous to the synthesis of the compound of 2b using 3,5-dimethyl isoxazole-4-sulfonyl chloride in 56% yield. MS (ESI) M+H=572.2.

Example 67

2-Methanesulfonylamino-N-[1-methyl-2-oxo-5-(4-trifluoromethyl-phenyl)-2,3-dihydro-1H-benzo[e][1,4]diazepin-3-yl]-propionamide The compound of Example 67 was synthesized from 0.08 g of the compound of 60b in a procedure analogous to the synthesis of the compound of 58b using methanesulfonyl chloride in 60% yield. MS (ESI) M+H=483.1.

Table 2 below provides representative Examples of the compounds of Formula (I) of the present invention.

TABLE 2

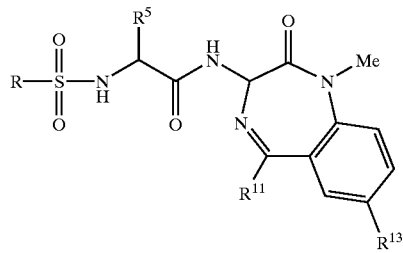

| Ex.# | R—SO$_2$— | R5 | R11 | R13 |
|---|---|---|---|---|
| 50 | 3,5-dimethyl-isoxazole-4-SO$_2$— | methyl | 4-F—phenyl | H |
| 51 | 3,5-dimethyl-isoxazole-4-SO$_2$— | i-butyl | 4-F—phenyl | H |
| 52 | 2-fluorophenyl-SO$_2$— | methyl | 4-F—phenyl | H |

TABLE 2-continued

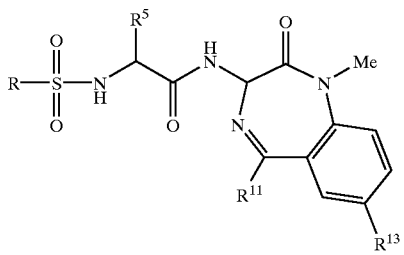

| Ex.# | R—SO₂— | R5 | R11 | R13 |
|------|--------|-----|------|------|
| 53 | 2-trifluoromethyl-phenyl-SO₂— | methyl | phenyl | H |
| 54 | 2-fluorophenyl-SO₂— | i-butyl | phenyl | H |
| 55 | 2-trifluoromethyl-phenyl-SO₂— | i-butyl | phenyl | H |
| 56 | n-propyl-SO₂— | i-butyl | phenyl | H |
| 57 | n-butyl-SO₂— | methyl | 4-CF₃—phenyl | H |
| 58 | 3,5-dimethyl-isoxazole-4-SO₂— | methyl | 4-CF₃—phenyl | H |
| 59 | 3,5-dimethyl-isoxazole-4-SO₂— | i-butyl | phenyl | Cl |
| 60 | n-propyl-SO₂— | i-butyl | 4-Cl—phenyl | H |
| 61 | 3,5-dimethyl-isoxazole-4-SO₂— | i-butyl | pyridin-2-yl | H |
| 62 | 3,5-dimethyl-isoxazole-4-SO₂— | methyl | phenyl | H |
| 63 | 3,5-dimethyl-isoxazole-4-SO₂— | (Me)₂N—CH₂— | phenyl | H |
| 64 | n-propyl-SO₂— | methyl | 4-CF₃—phenyl | H |
| 65 | 3,5-dimethyl-isoxazole-4-SO₂— | methyl | phenyl | Cl |
| 66 | 3,5-dimethyl-isoxazole-4-SO₂— | i-butyl | 4-Cl—phenyl | H |
| 67 | Methyl-SO₂— | methyl | 4-CF₃—phenyl | H |

Examples 68–99

Examples 68–99 were synthesized in a manner similar to the synthesis of the compounds of Examples 4–47, but using 1-Amino-cyclohexanecarboxylic Acid (1-Methyl-2-oxo-5-phenyl-2,3-dihydro-1H-benzo[e][1,4]diazepin-3-yl)-amide in a yield after RP-HPLC of 0.5–5 mg each.

The intermediate, 1-Amino-cyclohexanecarboxylic acid (1-methyl-2-oxo-5-phenyl-2,3-dihydro-1H-benzo[e][1,4]diazepin-3-yl)-amide, was synthesized by deprotection of [1-(1-Methyl-2-oxo-5-phenyl-2,3-dihydro-1H-benzo[e][1,4]diazepin-3-ylcarbamoyl)-cyclohexyl]-carbamic acid tert-butyl ester in a manner similar to the synthesis of the compound of 1b.

The intermediate, [1-(1-Methyl-2-oxo-5-phenyl-2,3-dihydro-1H-benzo[e][1,4]diazepin-3-ylcarbamoyl)-cyclohexyl]-carbamic acid tert-butyl ester, was synthesized in a manner similar to the synthesis of the compound of 1a except using 1.5 g (10.5 mmol) of N-Boc-1-aminocyclohexane.

Example 68

1-(Naphthalene-1-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=581.7

Example 69

1-(Naphthalene-2-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=581.7

Example 70

1-(Thiophene-2-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=537.7

Example 71

1-(Phenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=531.6

Example 72

1-(2,5-Dichlorophenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=600.5

Example 73

1-(2,4,6-Trimethylphenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=573.7

Example 74

1-(3-Nitrophenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=576.6

Example 75

1-(4-Bromophenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=610.5

Example 76

1-(4-Fluorophenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=549.6

Example 77

1-(4-Chlorophenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=566.1

Example 78

1-(Beta-styrene-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=557.7

Example 79

1-(4-Nitrophenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=576.6

Example 80

1-(4-tert-Butylphenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=587.7

Example 81

1-(p-Toluene-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=545.7

Example 82

1-(Benzyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=545.7

Example 83

1-(2-Methoxycarbonylphenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=589.7

Example 84

1-(2-Nitro-4-(trifluoromethyl)phenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=644.6

Example 85

1-(3-(Trifluoromethyl)phenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=599.6

Example 86

1-(2,5-Dimethoxyphenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=591.7

Example 87

1-(2-Methoxy-5chloro-1-phenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=596.1

Example 88

1-(3,4-Dichlorophenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=600.5

Example 89

1-(5-((Benzoylamino)methyl)-thiophene-2-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=670.8

Example 90

1-(4-(Phenylsulfonyl)thiophene-2-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=677.8

Example 91

1-(1-Methyl-5-(trifluoromethyl)-imidazole-3-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=685.7

Example 92

1-(4-Phenyl-phenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=607.7

Example 93

1-(Dibenzofuran-2-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=621.7

Example 94

1-(4-n-Butylphenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=587.7

Example 95

1-(2-(2-Methylthio-pyrimdin-3-yl)-thiophene-5-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=661.8

Example 96

1-(4-Phenoxy-phenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=623.7

Example 97

1-(3,5-Dimethyl-isoxazole-4-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=550.6

Example 98

1-(2-(Trifluoromethyl)phenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=599.6

Example 99

1-(2-Methylphenyl-sulfonylamino)-cyclohexanecarboxylic Acid (1-Methyl-2-oxo-5-phenyl-2,3-dihydro-1H-benzo[e][1,4]diazepin-3-yl)-amide. MS (ESI) M+H=545.7

Table 3 below provides representative Examples of the compounds of Formula (I) of the present invention.

TABLE 3

| Ex.# | R—SO$_2$— | MassSpec (Found) |
|---|---|---|
| 68 | 1-naphthalene-SO$_2$— | 581.7 |
| 69 | 2-naphthalene-SO$_2$— | 581.7 |
| 70 | 2-thiophene-SO$_2$— | 537.7 |
| 71 | phenyl-SO$_2$— | 531.6 |
| 72 | 2,5-dichlorophenyl-SO$_2$— | 600.5 |
| 73 | 2,4,6-trimethylphenyl-SO$_2$— | 573.7 |
| 74 | 3-nitrophenyl-SO$_2$— | 576.6 |
| 75 | 4-bromophenyl -SO$_2$— | 610.5 |
| 76 | 4-fluorophenyl-SO$_2$— | 549.6 |
| 77 | 4-chlorophenyl-SO$_2$— | 566.1 |
| 78 | beta-styrene-SO$_2$— | 557.7 |
| 79 | 4-nitrophenyl-SO$_2$— | 576.6 |
| 80 | 4-tert-butylphenyl-SO$_2$— | 587.7 |
| 81 | 4-methylphenyl-SO$_2$— | 545.7 |
| 82 | benzyl-SO$_2$— | 545.7 |
| 83 | 2-methoxycarbonylphenyl-SO$_2$— | 589.7 |
| 84 | 2-nitro-4-(trifluoromethyl)phenyl-SO$_2$— | 644.6 |
| 85 | 3-(trifluoromethyl)phenyl-SO$_2$— | 599.6 |
| 86 | 2,5-dimethoxyphenyl-SO$_2$— | 591.7 |
| 87 | 2-methoxy-5-chlorophenyl-SO$_2$— | 596.1 |
| 88 | 3,4-dichlorophenyl-SO$_2$— | 600.5 |
| 89 | 5-[(benzoylamino)methyl]thiophene-2-SO$_2$— | 670.8 |
| 90 | 4-(phenylsulfonyl)thiophene-2-SO$_2$— | 677.8 |
| 91 | 1-methyl-5-(trifluoromethyl)imidazole-3-SO$_2$— | 685.7 |
| 92 | 4-phenyl-phenyl-SO$_2$— | 607.7 |
| 93 | dibenzofuran-2-SO$_2$— | 621.7 |
| 94 | 4-n-butylphenyl-SO$_2$— | 587.7 |
| 95 | 2-(2-methylthio-pyrimdin-3-yl)thiophene-5-SO$_2$— | 661.8 |
| 96 | 4-phenoxy-phenyl-SO$_2$— | 623.7 |
| 97 | 3,5-dimethyl-isoxazole-4-SO$_2$— | 550.6 |
| 98 | 2-(trifluoromethyl)phenyl-SO$_2$— | 599.6 |
| 99 | 2-methylphenyl-SO$_2$— | 545.7 |

UTILITY

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γ-secretase activity, either directly or indirectly, control the production of Aβ. Such inhibition of β or γ-secretases reduces production of AD and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including PCT publication number WO 98/22493, EPO publication number 0652009, U.S. Pat. No. 5,703,129 and U.S. Pat. No. 5,593,846; all hereby incorporated by reference.

The compounds of the present invention have utility for the prevention and treatment of disorders involving Aβ production, such as cerebrovascular disorders.

Compounds of the present invention have been shown to inhibit Aβ production, as determined by the secretase inhibition assay described below.

Compounds of the present invention have been shown to inhibit Aβ production, utilizing the C-terminus β amyloid precursor protein accumulation assay described below.

Compounds of Formula (I) are expected to possess γ-secretase inhibitory activity. The γ-secretase inhibitory activity of the compounds of the present invention is demonstrated using assays for such activity, for example, using the assay described below. Compounds of the present invention have been shown to inhibit the activity of γ-secretase, as determined by the Aβ immunoprecipitation assay.

Compounds provided by this invention should also be useful as standards and reagents in determining the ability of a potential pharmaceutical to inhibit Aβ production. These would be provided in commercial kits comprising a compound of this invention.

As used herein "μg" denotes microgram, "mg" denotes milligram, "g" denotes gram, "μL", denotes microliter, "mL" denotes milliliter, "L" denotes liter, "nM" denotes nanomolar, "μM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetato.

A compound is considered to be active if it has an $IC_{50}$ or $K_i$ value of less than about 100 μM for the inhibition of Aβ production.

β Amyloid Precursor Protein Accumulation Assay

A novel assay to evaluate the accumulation of Aβ protein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1×Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 μl normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (clone 1101.1; directed against an internal peptide sequence in Aβ) and 50 μl protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an $IC_{50}$ less than 100 μM.

C-Terminus β Amyloid Precursor Protein Accumulation Assay

The effect of test compounds on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% NaN₃). Again, lysates are precleared with 5 ul normal rabbit serum/ 50 ul protein A Sepharose, followed by the addition of BC-1 antiserum (15 ul;) and 50 μl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an $IC_{50}$ less than 100 μM.

Aβ Immunoprecipitation Assay

This immunoprecipitation assay is specific for γ secretase (i.e., proteolytic activity required to generate the C-terminal end of Aβ either by direct cleavage or generating a C-terminal extended species which is subsequently further proteolyzed). N 9 cells are pulse labeled in the presence of a reported γ secretase inhibitor (MDL 28170) for 1 h, followed by washing to remove radiolabel and MDL 28170. The media is replaced and test compounds are added. The cells are chased for increasing periods of times and Aβ is isolated from the conditioned medium and C-terminal fragments from cell lysates (see above). The test compounds are characterized whether a stabilization of C-terminal fragments is observed and whether Aβ is generated from these accumulated precursor. A typical test compound prevents the generation of Aβ out of accumulated C-terminal fragments and is considered active with an $IC_{50}$ less than 100 μM.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient,and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of the Formula (I):

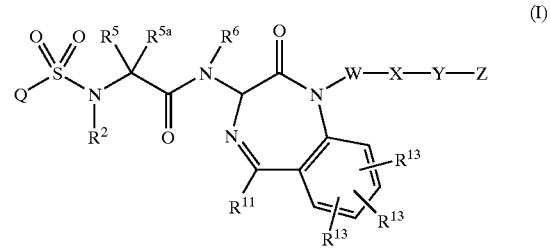

or a pharmaceutically acceptable salt thereof, wherein:

Q is $C_1$–$C_6$ alkyl substituted with 0–3 $R^{1a}$;
$C_3$–$C_{10}$ cycloalkyl substituted with 0–3 $R^{1b}$;
$C_3$–$C_{10}$ carbocycle substituted with 0–3 $R^{1b}$;
aryl substituted with 0–3 $R^{1b}$; or
5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1a}$, at each occurrence, is independently selected from H, $R^{1b}$, Cl, F, Br, I, $OR^{14}$, CN, $NO_2$, =O, $NR^{19}R^{20}$, $CF_3$, $C_1$–$C_4$ alkyl; $C_2$–$C_4$ alkenyl; $C_2$–$C_4$ alkynyl; $C_1$–$C_4$ haloalkyl; $C_1$–$C_4$ haloalkoxy;
$C_3$–$C_{10}$ carbocycle substituted with 0–3 $R^{1b}$;
aryl substituted with 0–3 $R^{1b}$; and
5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1b}$, at each occurrence, is independently selected from H, $OR^{14}$, Cl, F, Br, I, CN, $NO_2$, =O, $NR^{19}R^{20}$, $CF_3$, $OCF_3$, $C_1$–$C_4$ alkoxy, $C_1$–$C_4$ haloalkoxy;
—C(=O) $R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2NR^{19b}$—$R^{1d}$, —$NR^{19b}$S(=O)—$R^{1d}$, —S(=O)$NR^{19b}$—$R^{1d}$, —C(=O)O—$R^{1d}$, —OC(=O)—$R^{1d}$;
$C_1$–$C_6$ alkyl substituted with 0–3 $R^{1c}$;
$C_2$–$C_6$ alkenyl substituted with 0–2 $R^{1c}$;
$C_2$–$C_6$ alkynyl substituted with 0–2 $R^{1c}$;
$C_3$–$C_{10}$ cycloalkyl substituted with 0–3 $R^{1f}$;
$C_3$–$C_{10}$ carbocycle substituted with 0–3 $R^{1f}$;
aryl substituted with 0–3 $R^{1f}$; and
5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, $OR^{14}$, Cl, F, Br, I, CN, $NO_2$, $NR^{19}R^{20}$, $CF_3$, $C_1$–$C_4$ alkoxy, $C_1$–$C_4$ haloalkoxy;
—C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2NR^{19b}$—$R^{1d}$, —$NR^{19b}$S(=O)—$R^{1d}$, —S(=O)$NR^{19b}$—$R^{1d}$, —C(=O)O—$R^{1d}$, —OC(=O)—$R^{1d}$;
$C_3$–$C_{10}$ cycloalkyl substituted with 0–3 $R^{1f}$;
$C_3$–$C_{10}$ carbocycle substituted with 0–3 $R^{1f}$;
aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1d}$, at each occurrence, is independently selected from H, $C_1$–$C_6$ alkyl substituted with 0–3 $R^{1e}$;
$C_2$–$C_6$ alkenyl substituted with 0–2 $R^{1e}$;
$C_2$–$C_6$ alkynyl substituted with 0–2 $R^{1e}$;
$C_3$–$C_{10}$ cycloalkyl substituted with 0–3 $R^{1f}$;
$C_3$–$C_{10}$ carbocycle substituted with 0–3 $R^{1f}$;
aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1e}$, at each occurrence, is independently selected from H, $OR^{14}$, Cl, F, Br, I, CN, $NO_2$, =O, $NR^{19}R^{20}$, $CF_3$, $C_1$–$C_4$ alkyl, $C_1$–$C_4$ haloalkyl, $C_1$–$C_4$ alkoxy, $C_1$–$C_4$ haloalkoxy;
$C_3$–$C_{10}$ cycloalkyl substituted with 0–3 $R^{1f}$;
$C_3$–$C_{10}$ carbocycle substituted with 0–3 $R^{1f}$;
aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1f}$, at each occurrence, is independently selected from H, $OR^{14}$, $SR^{14}$, Cl, F, Br, I, CN, $NO_2$, =O, $NR^{19}R^{20}$, $CF_3$, $C_1$–$C_4$ alkyl, $C_1$–$C_4$ haloalkyl, $C_1$–$C_4$ alkoxy, $C_1$–$C_4$ haloalkoxy, and $C_1$–$C_4$ haloalkyl-S—;

$R^2$ is H, $C_1$–$C_6$ alkyl, ($C_1$–$C_6$ alkoxy) $C_1$–$C_3$ alkyl, $C_3$–$C_6$ carbocycle, aryl, ($C_3$–$C_6$ carbocycle)methyl, (aryl)methyl, (aryl)ethyl, or 5 to 10 membered heterocycle;

$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ cycloalkyl substituted with 0–3 $R^{5c}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H or $C_1$–$C_4$ alkyl;

$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$; acetyl, —S($C_1$–$C_4$ alkyl), —S(=O)($C_1$–$C_4$ alkyl), —S(=O)$_2$($C_1$–$C_4$ alkyl);
$C_3$–$C_{10}$ cycloalkyl substituted with 0–3 $R^{5c}$;
$C_3$–$C_{10}$ carbocycle substituted with 0–3 $R^{5c}$;
aryl substituted with 0–3 $R^{5c}$; and
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H;
$C_1$–$C_6$ alkyl substituted with 0–3 $R^{6a}$;
$C_3$–$C_{10}$ carbocycle substituted with 0–3 $R^{6b}$; or aryl substituted with 0–3 $R^{6b}$;

$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;

$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;

$R^{11}$ is selected from H, $C_1$–$C_4$ alkoxy, Cl, F, Br, I, CN, $NO_2$, $NR^{18}R^{19}$, C(=O)$R^{17}$, C(=O)O$R^{17}$, C(=O)$NR^{18}R^{19}$, S(=O)$_2NR^{18}R^{19}$, $CF_3$;
$C_1$–$C_6$ alkyl substituted with 0–1 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is —$(CR^8R^{8a})_p$—;

p is 0, 1, 2, 3, or 4;

$R^8$ and $R^{8a}$, at each occurrence, are independently selected from H, F, $C_1$–$C_4$ alkyl, $C_2$–$C_4$ alkenyl, $C_2$–$C_4$ alkynyl and $C_3$–$C_8$ cycloalkyl;

X is a bond;
  aryl substituted with 0–3 $R^{Xb}$;
  $C_3$–$C_{10}$ cycloalkyl substituted with 0–3 $R^{Xb}$;
  $C_3$–$C_{10}$ carbocycle substituted with 0–3 $R^{Xb}$; or
  5 to 10 membered heterocycle containing 1 to 4 heteroatoms selected from nitrogen, oxygen, and sulphur, wherein said 5 to 10 membered heterocycle is substituted with 0–3 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond or —$(CR^9R^{9a})_t$—V—$(CR^9R^{9a})_u$—;

t is 0, 1, 2, or 3;

u is 0, 1, 2, or 3;

$R^9$ and $R^{9a}$, at each occurrence, are independently selected from H, F, $C_1$–$C_6$ alkyl or $C_3$–$C_8$ cycloalkyl;

V is a bond, —C(=O)—, —O—, —S—, —S(=O)—, —S(=O)$_2$—, —N($R^{19}$)—, —C(=O)$NR^{19b}$—, $NR^{19b}$C(=O)—, —$NR^{19b}$S(=O)$_2$—, —S(=O)$_2$$NR^{19b}$—, —$NR^{19b}$S(=O)—, —S(=O)$NR^{19b}$—, —C(=O)O—, or —OC(=O)—;

Z is H;
  $C_1$–$C_8$ alkyl substituted with 0–2 $R^{12}$;
  $C_2$–$C_6$ alkenyl substituted with 0–2 $R^{12}$;
  $C_2$–$C_6$ alkynyl substituted with 0–2 $R^{12}$;
  aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

$R^{14}$, at each occurrence, is independently selected from H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{16}$, at each occurrence, is independently selected from H, OH, $C_1$–$C_6$ alkyl, phenyl, benzyl, phenethyl, —C(=O)—($C_{1-6}$ alkyl) and —S(=O)$_2$—($C_1$–$C_6$ alkyl);

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperizinyl;

$R^{17}$ is H, aryl, aryl-$CH_2$—, $C_1$–$C_6$ alkyl, or $C_2$–$C_6$ alkoxy-alkyl;

$R^{18}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19b}$, at each occurrence, is independently selected from H, $C_1$–$C_4$ alkyl, phenyl, benzyl, and phenethyl; and $R^{20}$ and $R^{21}$, at each occurrence, are independently selected from H, $C_1$–$C_4$ alkyl, aryl, and aryl($C_1$–$C_2$ alkyl)—.

2. A compound of claim 1 of Formula (I):

(I)

or a pharmaceutically acceptable salt form thereof, wherein:
  Q is $C_1$–$C_6$ alkyl substituted with 0–3 $R^{1a}$;
    $C_3$–$C_{10}$ cycloalkyl substituted with 0–3 $R^{1b}$;
    aryl substituted with 0–3 $R^{1b}$; or
    5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1a}$, at each occurrence, is independently selected from H, Cl, F, Br, $NR^{19}R^{20}$, $CF_3$, $C_1$–$C_4$ alkyl; $C_1$–$C_4$ haloalkyl; aryl substituted with 0–3 $R^{1b}$; and
  5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1b}$, at each occurrence, is independently selected from H, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy;
  —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2$$NR^{19b}$—$R^{1d}$, $NR^{19b}$S(=O)—$R^{1d}$, —S(=O)$NR^{19b}$—$R^{1d}$, —C(=O)O—$R^{1d}$, —OC(=O)—$R^{1d}$;
  $C_1$–$C_6$ alkyl substituted with 0–3 $R^{1c}$;
  $C_3$–$C_{10}$ cycloalkyl substituted with 0–3 $R^{1f}$;
  aryl substituted with 0–3 $R^{1f}$; and
  5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, $OR^{14}$, Cl, F, Br, $NO_2$, $NR^{19}R^{20}$, $CF_3$, $C_1$–$C_4$ alkoxy, $C_1$–$C_4$ haloalkoxy; —C(=O)—$R^{1d}$, —O—$R^{1d}$, —S—$R^{1d}$, S(=O)—$R^{1d}$, —S(=O)$_2$—$R^{1d}$, —N($R^{19}$)—$R^{1d}$, —C(=O)N$R^{19b}R^{1d}$, —N$R^{19b}$C(=O)—$R^{1d}$, —N$R^{19b}$S(=O)$_2$—$R^{1d}$, —S(=O)$_2$N$R^{19b}$—$R^{1d}$, —N$R^{19b}$S(=O)—$R^{1d}$, —S(=O)N$R^{19b}$—$R^{1d}$, —C(=O)O—$R^{1d}$, —OC(=O)—$R^{1d}$;
 $C_3$–$C_{10}$ cycloalkyl substituted with 0–3 $R^{1f}$;
 $C_3$–$C_{10}$ carbocycle substituted with 0–3 $R^{1f}$;
 aryl substituted with 0–3 $R^{1f}$; and
 5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1d}$, at each occurrence, is independently selected from H, $C_1$–$C_6$ alkyl, and aryl substituted with 0–3 $R^{1f}$;

$R^{1f}$, at each occurrence, is independently selected from H, Cl, F, Br, $NO_2$, $CF_3$, $C_1$–$C_4$ alkyl, $C_1$–$C_4$ haloalkyl, $C_1$–$C_4$ alkoxy, $C_1$–$C_4$ haloalkoxy, and $C_1$–$C_4$ haloalkyl-S—;

$R^2$ is H, methyl, or ethyl;

$R^5$ is $OR^{14}$;
 $C_1$–$C_6$ alkyl substituted with 0–3 $R^{5b}$;
 $C_1$–$C_6$ alkoxy substituted with 0–3 $R^{5b}$;
 $C_2$–$C_6$ alkenyl substituted with 0–3 $R^{5b}$; or
 $C_2$–$C_6$ alkynyl substituted with 0–3 $R^{5b}$;

$R^{5a}$ is H or $C_1$–$C_4$ alkyl;

$R^{5b}$, at each occurrence, is independently selected from:
 H, $C_1$–$C_6$ alkyl, $CF_3$, $OR^{14}$, Cl, F, Br, I, =O, CN, $NO_2$, $NR^{15}R^{16}$, acetyl, —S($C_1$–$C_4$ alkyl), S(=O)($C_1$–$C_4$ alkyl), S(=O)$_2$($C_1$–$C_4$ alkyl);
 $C_3$–$C_{10}$ cycloalkyl substituted with 0–3 $R^{5c}$;
 aryl substituted with 0–3 $R^{5c}$; or
 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H, methyl or ethyl;

$R^{11}$ is selected from
 H, $C_1$–$C_4$ alkoxy, Cl, F, Br, I, CN, $NO_2$, $NR^{18}R^{19}$, C(=O)$R^{17}$, C(=O)O$R^{17}$, C(=O)N$R^{18}R^{19}$, S(=O)$_2NR^{18}R^{19}$, $CF_3$;
 $C_1$–$C_6$ alkyl substituted with 0–1 $R^{11a}$;
 aryl substituted with 0–3 $R^{11b}$;
 $C_3$–$C_{10}$ carbocycle substituted with 0–3 $R^{11b}$; or
 5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H,
 $C_1$–$C_6$ alkyl, $OR^{14}$, Cl, F, Br, I, =O, CN, $NO_2$, $NR^{15}R^{16}$, $CF_3$, phenyl substituted with 0–3 $R^{11b}$;
 $C_3$–$C_{10}$ carbocycle substituted with 0–3 $R^{11b}$; or
 5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is —(C$R^8R^{8a}$)$_p$—;

p is 0, 1, or 2;

$R^8$ and $R^{8a}$, at each occurrence, are independently selected from H, F, methyl, and ethyl;

X is a bond;
 phenyl substituted with 0–3 $R^{Xb}$;
 $C_3$–$C_6$ cycloalkyl substituted with 0–3 $R^{Xb}$; or
 5 to 6 membered heterocycle containing 1 to 4 heteroatoms selected from nitrogen, oxygen, and sulphur, wherein said 5 to 6 membered heterocycle is substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond or —(C$R^9R^{9a}$)$_t$—V—(C$R^9R^{9a}$)$_u$—;

t is 0, 1, or 2;

u is 0, 1, or 2;

$R^9$ and $R^{9a}$, at each occurrence, are independently selected from H, F, methyl, and ethyl;

V is a bond, —C(=O)—, —O—, —S—, —S(=O)—, —S(=O)$_2$—, —N($R^{19}$)—, —C(=O)NH—, or —NHC(=O)—;

Z is H;
 $C_1$–$C_6$ alkyl substituted with 0–2 $R^{12}$;
 $C_2$–$C_6$ alkenyl substituted with 0–2 $R^{12}$;
 $C_2$–$C_6$ alkynyl substituted with 0–2 $R^{12}$;
 phenyl substituted with 0–4 $R^{12b}$;
 $C_3$–$C_6$ carbocycle substituted with 0–4 $R^{12b}$; or
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
 $C_3$–$C_6$ carbocycle substituted with 0–4 $R^{12b}$; or
 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_4$ alkyl, $C_1$–$C_4$ alkoxy, Cl, F, Br, CN, $NO_2$, and $CF_3$;

$R^{14}$, at each occurrence, is independently selected from H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, phenyl,benzyl, phenethyl, —C(=O)—($C_1$–$C_6$ alkyl) and —S(=O)$_2$—($C_1$–$C_6$ alkyl);

$R^{16}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl);

alternatively, —N$R^{15}R^{16}$ may be a heterocyclic ring selected from the group piperidinyl, morpholinyl, thiomorpholinyl, pyrrolidinyl, homopiperidinyl, piperazinyl, and N-methylpiperizinyl;

81

$R^{17}$ is H, aryl, aryl-$CH_2$—, $C_1$–$C_6$ alkyl, or $C_2$–$C_6$ alkoxyalkyl;

$R^{18}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19}$, at each occurrence, is independently selected from H, OH, $C_1$–$C_6$ alkyl, phenyl, benzyl, phenethyl, —C(=O)—($C_{1-6}$ alkyl) and —S(=O)$_2$—($C_1$–$C_6$ alkyl); and $R^{20}$ is H or $C_1$–$C_4$.

3. A compound of claim 2 of Formula (Ia):

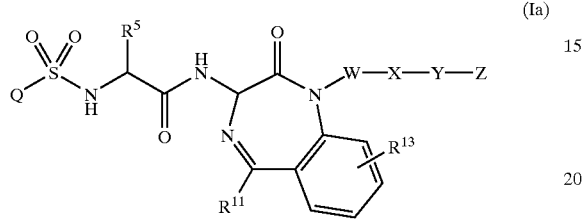

(Ia)

or a pharmaceutically acceptable salt form thereof, wherein:

Q is $C_1$–$C_6$ alkyl substituted with 0–2 $R^{1a}$;
   aryl substituted with 0–3 $R^{1b}$; or
   5 to 10 membered heterocycle containing 1 to 3 heteroatoms selected from nitrogen, oxygen, and sulphur, wherein said 5 to 10 membered heterocycle is substituted with 0–3 $R^{1b}$;

$R^{1a}$, at each occurrence, is independently selected from H, Cl, F, Br, $NR^{19}R^{20}$, $CF_3$, $C_1$–$C_4$ alkyl, $C_1$–$C_4$ haloalkyl, and phenyl substituted with 0–3 $R^{1b}$;

$R^{1b}$, at each occurrence, is independently selected from H, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy; —C(=O)—$R^{1d}$, —O—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2$$NR^{19b}$—$R^{1d}$, —C(=O)O—$R^{1d}$, —OC(=O)—$R^{1d}$;
   $C_1$–$C_6$ alkyl substituted with 0–3 $R^{1c}$;
   aryl substituted with 0–3 $R^{1f}$; and
   5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2$$NR^{19b}$—$R^{1d}$, —$NR^{19b}$S(=O)—$R^{1d}$, —S(=O)$NR^{19b}$—$R^{1d}$, —C(=O)O—$R^{1d}$, and —OC(=O)—$R^{1d}$;

$R^{1d}$, at each occurrence, is independently selected from H, $C_1$–$C_6$ alkyl, and aryl substituted with 0–3 $R^{1f}$;

$R^{1f}$, at each occurrence, is independently selected from H, Cl, F, Br, $NO_2$, $CF_3$, $C_1$–$C_4$ alkyl, $C_1$–$C_4$ haloalkyl, $C_1$–$C_4$ alkoxy, $C_1$–$C_4$ haloalkoxy, and $C_1$–$C_4$ haloalkyl-S—;

$R^5$ is $OR^{14}$;
   $C_1$–$C_6$ alkyl substituted with 0–1 $R^{5b}$;
   $C_2$–$C_6$ alkenyl substituted with 0–1 $R^{5b}$; or
   $C_2$–$C_6$ alkynyl substituted with 0–1 $R^{5b}$;

$R^{5b}$, at each occurrence, is independently selected from: H, methyl, ethyl, propyl, butyl, $CF_3$, $OR^{14}$, Cl, F, Br, I, =O, CN, $NO_2$, $NR^{15}R^{16}$; acetyl, —S($C_1$–$C_4$ alkyl),

82

—S(=O)($C_1$–$C_4$ alkyl), —S(=O)$_2$($C_1$–$C_4$ alkyl), $C_3$–$C_7$ cycloalkyl substituted with 0–3 $R^{5c}$;
   phenyl substituted with 0–3 $R^{5c}$; and
   5 to 7 membered heterocycle containing 1 to 4 heteroatoms selected from nitrogen, oxygen, and sulphur, wherein said 5 to 7 membered heterocycle is substituted with 0–3 $R^{5c}$;

$R^{5c}$, at each occurrence, is independently selected from H, OH, Cl, F, —$NR^{15}R^{16}$, $CF_3$, acetyl, $SCH_3$, $S(=O)_2CH_3$, methyl, ethyl, propyl, butyl, metrhoxy, ethoxy, propoxy, $C_1$–$C_2$ haloalkyl, and $C_1$–$C_2$ haloalkoxy;

$R^{11}$ is selected from H, —$NR^{18}R^{19}$, —C(=O)$R^{17}$, —C(=O)$OR^{17}$, —C(=O)$NR^{18}R^{19}$, —S(=O)$_2NR^{18}R^{19}$, —$CF_3$;
   $C_1$–$C_6$ alkyl substituted with 0–1 $R^{11a}$;
   phenyl substituted with 0–3 $R^{11b}$;
   $C_3$–$C_6$ carbocycle substituted with 0–3 $R^{11b}$; or
   5 to 7 membered heterocycle containing 1 to 4 heteroatoms selected from nitrogen, oxygen, and sulphur, wherein said 5 to 7 membered heterocycle is substituted with 0–3 $R^{11b}$;

$R^{11a}$, at each occurrence, is independently selected from H, $C_1$–$C_4$ alkyl, $OR^{14}$, Cl, F, Br, CN, $NO_2$, $NR^{15}R^{16}$, $CF_3$, phenyl substituted with 0–3 $R^{11b}$;
   $C_3$–$C_{10}$ carbocycle substituted with 0–3 $R^{11b}$; or
   5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is —$(CR^8R^{8a})_p$—;

p is 0, 1, or 2;

$R^8$ and $R^{8a}$, at each occurrence, are independently selected from H, F, methyl, and ethyl;

X is a bond;
   phenyl substituted with 0–3 $R^{Xb}$;
   $C_3$–$C_6$ cycloalkyl substituted with 0–3 $R^{Xb}$; or
   5 to 6 membered heterocycle containing 1 to 4 heteroatoms selected from nitrogen, oxygen, and sulphur, wherein said 5 to 6 membered heterocycle is substituted with 0–2 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond or —$(CR^9R^{9a})_t$—V—$(CR^9R^{9a})_u$—;

t is 0, 1, or 2;

u is 0, 1, or 2;

$R^9$ and $R^{9a}$, at each occurrence, are independently selected from H, F, methyl, and ethyl;

V is a bond, —C(=O)—, —O—, —S—, —S(=O)—, —S(=O)$_2$—, —N($R^{19}$)—, —C(=O)NH—, or —NHC(=O)—;

Z is H;
   $C_1$–$C_6$ alkyl substituted with 0–2 $R^{12}$;
   $C_2$–$C_6$ alkenyl substituted with 0–2 $R^{12}$;
   $C_2$–$C_6$ alkynyl substituted with 0–2 $R^{12}$;
   phenyl substituted with 0–4 $R^{12b}$;
   $C_3$–$C_6$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_3$ alkyl, $C_1$–$C_3$ alkoxy, Cl, F, Br, CN, $NO_2$, and $CF_3$;

$R^{14}$, at each occurrence, is independently selected from H, phenyl, benzyl, $C_1$–$C_6$ alkyl, and $C_2$–$C_6$ alkoxyalkyl;

$R^{15}$, at each occurrence, is independently selected from H, $C_1$–$C_6$ alkyl, phenyl, benzyl, phenethyl, —C(=O)—($C_{1-6}$ alkyl) and —S(=O)$_2$—($C_1$–$C_6$ alkyl);

$R^{16}$, at each occurrence, is independently selected from H, OH, $C_1$–$C_6$ alkyl, phenyl, benzyl, phenethyl, —C(=O)—($C_1$–$C_6$ alkyl) and —S(=O)$_2$—($C_1$–$C_6$ alkyl);

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperizinyl;

$R^{17}$ is H, phenyl, benzyl, $C_1$–$C_4$ alkyl, or $C_2$–$C_4$ alkoxyalkyl;

$R^{18}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{19}$, at each occurrence, is independently selected from H, OH, methyl, ethyl, propyl, butyl, phenyl, benzyl, and phenethyl; and $R^{20}$ is H, methyl, ethyl, propyl, or butyl.

4. A compound of claim 3 of Formula (Ia)

(Ia)

wherein:
Q is $C_1$–$C_6$ alkyl substituted with 0–1 $R^{1a}$;
phenyl substituted with 0–3 $R^{1b}$;
naphthyl substituted with 0–3 $R^{1b}$; or
5 to 10 membered heterocycle containing 1 to 2 heteroatoms selected from nitrogen, oxygen, and sulphur, wherein said 5 to 10 membered heterocycle is substituted with 0–3 $R^{1b}$;

$R^{1a}$, at each occurrence, is independently selected from H, Cl, F, Br, —$NR^{19}R^{20}$, —$CF_3$; and
phenyl substituted with 0–3 $R^{1b}$;

$R^{1b}$, at each occurrence, is independently selected from H, methyl, ethyl, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy;
—C(=O)—$R^{1d}$, —O—$R^{1d}$, —S(=O)$_2$—$R^{1d}$, —N($R^{19}$)—$R^{1d}$,
—C(=O)$NR^{19b}R^{1d}$, $NR^{19b}C(=O)$—$R^{1d}$, —$NR^{19b}S(=O)_2$—$R^{1d}$, —S(=O)$_2NR^{19b}$—$R^{1d}$, —C(=O)O—$R^{1d}$, —OC(=O)—$R^{1d}$;

$C_1$–$C_6$ alkyl substituted with 0–3 $R^{1c}$;
phenyl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1c}$, at each occurrence, is independently selected from H, —C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)$NR^{19b}R^{1d}$, —$NR^{19b}C(=O)$—$R^{1d}$, —$NR^{19b}S(=O)_2$—$R^{1d}$, and —S(=O)$_2NR^{19b}$—$R^{1d}$;

$R^{1d}$, at each occurrence, is independently selected from H, $C_1$–$C_6$ alkyl; and phenyl substituted with 0–3 $R^{1f}$;

$R^{1f}$, at each occurrence, is independently selected from H, Cl, F, Br, $NO_2$, $CF_3$, methyl, ethyl, propyl, methoxy, ethoxy, propoxy, $C_1$–$C_2$ haloalkyl, and $C_1$–$C_2$ haloalkoxy;

$R^5$ is $OR^{14}$ or $C_1$–$C_4$ alkyl substituted with 0–1 $R^{5b}$;

$R^{5b}$, at each occurrence, is independently selected from:
H, methyl, ethyl, propyl, butyl, —$NR^{15}R^{16}$;
$C_3$–$C_7$ cycloalkyl substituted with 0–3 $R^{5c}$;
phenyl substituted with 0–3 $R^{5c}$; or
5 to 7 membered heterocycle containing 1 to 4 heteroatoms selected from nitrogen, oxygen, and sulphur, wherein said 5 to 7 membered heterocycle is substituted with 0–3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{5c}$, at each occurrence, is independently selected from H, OH, Cl, F, —$NR^{15}R^{16}$, $CF_3$, acetyl, $SCH_3$, $S(=O)_2CH_3$, methyl, and methoxy;

$R^{11}$ is selected from
H, $NR^{18}R^{19}$, $CF_3$;
$C_1$–$C_6$ alkyl substituted with 0–1 $R^{11a}$;
phenyl substituted with 0–3 $R^{11b}$;
$C_3$–$C_6$ carbocycle substituted with 0–3 $R^{11b}$; or
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, Br, CN, $NO_2$, $NR^{15}R^{16}$, $CF_3$, phenyl substituted with 0–3 $R^{11b}$;
$C_3$–$C_6$ carbocycle substituted with 0–3 $R^{11b}$; or
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

W is —(CHR$^8$)$_p$—;

p is 0 or 1;

$R^8$ is H, methyl, or ethyl;

X is a bond;
  phenyl substituted with 0–2 $R^{Xb}$;
  $C_3$–$C_6$ cycloalkyl substituted with 0–3 $R^{Xb}$; or
  5 to 6 membered heterocycle containing 1 to 4 heteroatoms selected from nitrogen, oxygen, and sulphur, wherein said 5 to 6 membered heterocycle is substituted with 0–1 $R^{Xb}$;

$R^{Xb}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

Y is a bond, —V—, —CH$_2$—V—, —V—CH$_2$—, or —CH$_2$—V—CH$_2$—;

V is a bond, —C(=O)—, —O—, —S—, —S(=O)—, —S(=O)$_2$—, —N(R$^{19}$)—, —C(=O)NH—, or —NHC(=O)—;

Z is H;
  $C_1$–$C_6$ alkyl substituted with 0–2 $R^{12}$;
  $C_2$–$C_6$ alkenyl substituted with 0–2 $R^{12}$;
  $C_2$–$C_6$ alkynyl substituted with 0–2 $R^{12}$;
  phenyl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, methyl, ethyl, methoxy, ethoxy, Cl, F, Br, $NO_2$, or $CF_3$;

$R^{14}$, at each occurrence, is independently selected from H, phenyl, benzyl, $C_1$–$C_4$ alkyl, or $C_2$–$C_4$ alkoxyalkyl;

$R^{15}$, at each occurrence, is independently selected from H, methyl, ethyl, propyl, butyl, phenyl, benzyl, and phenethyl;

$R^{16}$, at each occurrence, is independently selected from H, OH, methyl, ethyl, propyl, butyl, phenyl, benzyl, phenethyl, $CH_3CH_2C(=O)$—, $CH_3C(=O)$—, $CH_3CH_2OC(=O)$—, $CH_3OC(=O)$—, $CH_3CH_2S(=O)_2$— and $CH_3S(=O)_2$—;

$R^{18}$, at each occurrence, is independently selected from H, methyl, ethyl, propyl, butyl, phenyl, benzyl, and phenethyl;

$R^{19}$, at each occurrence, is independently selected from H, OH, methyl, ethyl, propyl, and butyl; and $R^{20}$ is H, methyl, ethyl, propyl, or butyl.

5. A compound of claim 4 of Formula (Ia)

(Ia)

wherein:
Q is $C_1$–$C_4$ alkyl substituted with 0–1 $R^{1a}$;
  phenyl substituted with 0–3 $R^{1b}$;
  naphthyl substituted with 0–3 $R^{1b}$; or
  5 to 10 membered heterocycle containing 1 to 2 heteroatoms selected from nitrogen, oxygen, and sulphur, wherein said 5 to 10 membered heterocycle is substituted with 0–3 $R^{1b}$; wherein said 5 to 10 membered heterocycle is selected from pyridinyl, quinolinyl, pyrimidinyl, triazinyl, furanyl, thienyl, thiazolyl, imidazolyl, oxazolyl, and isoxazolyl;

$R^{1a}$, at each occurrence, is independently selected from H, Cl, F, Br, $CF_3$, and phenyl substituted with 0–3 $R^{1b}$;

$R^{1b}$, at each occurrence, is independently selected from H, methyl, ethyl, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy; —C(=O)—$R^{1d}$, —O—$R^{1d}$, —S(=O)$_2$—$R^{1d}$, —N(R$^{19}$)—$R^{1d}$, —C(=O)NR$^{19b}$R$^{1d}$, —NR$^{19b}$C(=O)—$R^{1d}$, —NR$^{19b}$S(=O)$_2$—$R^{1d}$, —S(=O)$_2$NR$^{19b}$—$R^{1d}$, —C(=O) O—$R^{1d}$, —OC(=O)—$R^{1d}$;
  $C_1$–$C_6$ alkyl substituted with 0–3 $R^{1c}$;
  phenyl substituted with 0–3 $R^{1f}$; and
  5 to 6 membered heterocycle containing 1 to 4 heteroatoms selected from nitrogen, oxygen, and sulphur, wherein said 5 to 6 membered heterocycle is substituted with 0–3 $R^{1f}$;

$R^{1c}$, at each occurrence, is independently selected from H, C(=O)—$R^{1d}$, O—$R^{1d}$, —S—$R^{1d}$, —S(=O)—$R^{1d}$, —S(=O)$_2$—$R^{1d}$, —N(R$^{19}$)—$R^{1d}$, —C(=O)NR$^{19b}$R$^{1d}$, —NR$^{19b}$C(=O)—$R^{1d}$, —NR$^{19b}$S(=O)$_2$—$R^{1d}$, and —S(=O)$_2$NR$^{19b}$—$R^{1d}$;

$R^{1d}$, at each occurrence, is independently selected from H, $C_1$–$C_6$ alkyl; and phenyl substituted with 0–3 $R^{1f}$;

$R^{1f}$, at each occurrence, is independently selected from H, Cl, F, Br, $NO_2$, $CF_3$, —$OCF_3$, methyl, ethyl, methoxy, and ethoxy;

$R^5$ is methyl substituted with 0–1 $R^{5b}$;
  ethyl substituted with 0–1 $R^{5b}$;
  propyl substituted with 0–1 $R^{5b}$; or
  butyl substituted with 0–1 $R^{5b}$;

$R^{5b}$, at each occurrence, is independently selected from: H, methyl, ethyl, and $NR^{15}R^{16}$;

$R^{11}$ is selected from
  H, $NR^{18}R^{19}$, $CF_3$;
  $C_1$–$C_4$ alkyl substituted with 0–1 $R^{11a}$;
  phenyl substituted with 0–3 $R^{11b}$;
  $C_3$–$C_6$ carbocycle substituted with 0–3 $R^{11b}$; or
  5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, $NR^{15}R^{16}$, $CF_3$;
phenyl substituted with 0–3 $R^{11b}$;
$C_3$–$C_6$ carbocycle substituted with 0–3 $R^{11b}$; or
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, $NR^{15}R^{16}$, $CF_3$, methyl, ethyl, propyl, methoxy, and ethoxy;

W is a bond, —$CH_2$—, or —$CH(CH_3)$—;

X is a bond;
phenyl substituted with 0–1 $R^{Xb}$;
$C_3$–$C_6$ cycloalkyl substituted with 0–3 $R^{Xb}$; or
5 to 6 membered heterocycle containing 1 to 3 heteroatoms selected from nitrogen, oxygen, and sulphur; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, and isoxazolyl;

Y is a bond, —V—, —$CH_2$—V—, or —V—$CH_2$—;

V is a bond, —C(=O)—, —O—, —S—, —S(=O)—, —S(=O)$_2$—, —N($R^{19}$)—, —C(=O)NH—, or —NHC(=O)—;

Z is H;
$C_1$–$C_6$ alkyl substituted with 0–2 $R^{12}$;
$C_2$–$C_6$ alkenyl substituted with 0–2 $R^{12}$;
$C_2$–$C_6$ alkynyl substituted with 0–2 $R^{12}$;
phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, $NR^{15}R^{16}$, $CF_3$, $OCF_3$, acetyl, $SCH_3$, S(=O)$CH_3$, S(=O)$_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, methyl, methoxy, Cl, F, Br, and $CF_3$;

$R^{14}$, at each occurrence, is independently selected from H, phenyl, benzyl, methyl, ethyl, propyl, and butyl;

$R^{15}$, at each occurrence, is independently selected from H, methyl, ethyl, propyl, or butyl;

$R^{16}$, at each occurrence, is independently selected from H, OH, methyl, ethyl, propyl, butyl, phenyl, benzyl, and phenethyl;

$R^{18}$, at each occurrence, is independently selected from H, methyl, ethyl, propyl, butyl, phenyl, benzyl, and phenethyl;

$R^{19}$, at each occurrence, is independently selected from H, OH, methyl, ethyl, propyl, and butyl; and $R^{20}$ is H, methyl, ethyl, propyl, or butyl.

6. A compound of claim 4 wherein:

Q is —$CH_3$, —$CH_2CH_3$, —$CH_2CH_2CH_3$, —$CH_2CH_2CH_2CH_3$, —$CH(CH_3)_2$, —$CH(CH_3)CH_2CH_3$, —$CH_2CH(CH_3)_2$, —$CH_2CF_3$, —$CH_2CH_2CF_3$, —$CH_2CH_2CH_2CF_3$, phenyl-, 4-tBu-phenyl-, 4-iPr-phenyl-, 4-Et-phenyl-, 2-F-phenyl-, 3-F-phenyl-, 4-F-phenyl-, 2-Cl-phenyl-, 3-Cl-phenyl-, 4-Cl-phenyl-, 2-Br-phenyl-, 3-Br-phenyl-, 4-Br-phenyl-, 2-$NO_2$-phenyl-, 3-$NO_2$-phenyl-, 4-$NO_2$-phenyl-, 2-$CH_3$-phenyl-, 3-$CH_3$-phenyl-, 4-$CH_3$-phenyl-, 2-$CH_3O$-phenyl-, 3-$CH_3O$-phenyl-, 4-$CH_3O$-phenyl-, 2-$CF_3$-phenyl-, 3-$CF_3$-phenyl-, 4-$CF_3$-phenyl-, 2-$CF_3O$-phenyl-, 3-$CF_3O$-phenyl-, 4-$CF_3O$-phenyl-, 2-$CH_3CONH$-phenyl, 3-$CH_3CONH$-phenyl, 4-$CH_3CONH$-phenyl, 2-methyoxycarbonyl-phenyl-, 4-phenyl-phenyl-, 2,3-diF-phenyl-, 2,4-diF-phenyl-, 2,5-diF-phenyl-, 2,6-diF-phenyl-, 3,4-diF-phenyl-, 3,5-diF-phenyl-, 2,3-diCl-phenyl-, 2,4-diCl-phenyl-, 2,5-diCl-phenyl-, 2,6-diCl-phenyl-, 3,4-diCl-phenyl-, 3,5-diCl-phenyl-, 3-F-4-Cl-phenyl-, 3-F-5-Cl-phenyl-, 3-Cl-4-F-phenyl-, 2,3-diMe-phenyl-, 2,4-diMe-phenyl-, 2,5-diMe-phenyl-, 2,6-diMe-phenyl-, 3,4-diMe-phenyl-, 3,5-diMe-phenyl-, 2,3-diMeO-phenyl-, 2,4-diMeO-phenyl-, 2,5-diMeO-phenyl-, 2,6-diMeO-phenyl-, 3,4-diMeO-phenyl-, 3,5-diMeO-phenyl-, 2,3-di$CF_3$-phenyl-, 2,4-di$CF_3$-phenyl-, 2,5-di$CF_3$-phenyl-, 2,6-di$CF_3$-phenyl-, 3,4-di$CF_3$-phenyl-, 3,5-di$CF_3$-phenyl-, 2-$NO_2$-4-$CF_3$-phenyl-, 2-Me-5-Cl-phenyl-, 2,4,6-triMe-phenyl-, benzyl-, naphth-1-yl-, naphth-2-yl-, beta-styrene-, furanyl-, thienyl-, pyridyl-, thiazolyl-, imidazol-1-yl-, oxazolyl-, isoxazolyl-, quinolin-8-yl-, 3-methyl-isoxazol-4-yl-, 3,5-dimethyl-isoxazol-4-yl-, 3-bromo-5-chloro-thiophen-2-yl-, 2,3-dichlorothiophen-5-yl-, 4-bromo-5-chlorothiophen-2-yl-, 5-[(benzoylamino)methyl]-thiophen-2-yl-, 4-phenylsulfonylthiophen-2-yl-, 5-(phenylsulfonyl)thiophen-2-yl-, 2-(1-methyl-(5-trifluoromethyl)pyrazole)thiophen-5-yl-, 5-(2-pyridyl)thiophen-2-yl-, 1-methyl-5-(trifluoromethyl)imidazol-3-yl-, 2-(2-methylthio-pyrimdin-3-yl)-thiophen-5-yl-, or dibenzofuran-2-yl-;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, (3-$CH_3$-cyclobutyl)$CH_2CH_2$—, phenyl-$CH_2$—, (2-F-phenyl)$CH_2$—, (3-F-phenyl)$CH_2$—, (4-F-phenyl)$CH_2$—, furanyl-$CH_2$—, thienyl-$CH_2$—, pyridyl-$CH_2$—, 1-imidazolyl-$CH_2$—, oxazolyl-$CH_2$—, isoxazolyl-$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, or isoxazolyl-$CH_2CH_2$—, W is a bond, —$CH_2$—, or —$CH(CH_3)$—;

X is a bond;

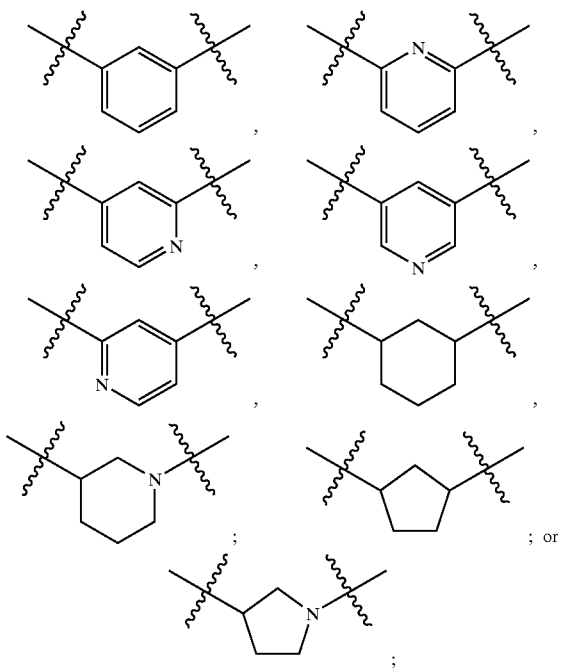

; or

Y is a bond, —CH$_2$—V—, —V—, or —V—CH$_2$—;
V is a bond, —C(=O)—, —O—, —S—, —S(=O)—, —S(=O)$_2$—, —NH—, —N(CH$_3$)—, —C(=O)NH—, or —NHC(=O)—,
Z is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$, —CH$_2$C(CH$_3$)$_3$, —C(CH$_3$)$_2$CH$_2$CH$_3$, —CH(CH$_3$)CH(CH$_3$)$_2$, —CH$_2$CH$_2$CH$_2$CH$_2$CH$_2$CH$_3$, —CH(CH$_3$)CH$_2$CH$_2$CH$_2$CH$_3$, —CH$_2$CH(CH$_3$)CH$_2$CH$_2$CH$_3$, —CH$_2$CH$_2$CH(CH$_3$)CH$_2$CH$_3$, —CH$_2$CH$_2$CH$_2$CH(CH$_3$)$_2$, —CH$_2$CH(CH$_2$CH$_3$)$_2$, —CH$_2$CH$_2$C(CH$_3$)$_3$, —CH(CH$_2$CH$_3$)CH$_2$CH$_2$CH$_3$, —CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, cyclopropyl-, (cyclopropyl)CH$_2$—, (cyclopropyl)CH$_2$CH$_2$—, cyclobutyl-, (cyclobutyl)CH$_2$—, (cyclobutyl)CH$_2$CH$_2$—, cyclopentyl-, (cyclopentyl)CH$_2$—, (cyclopentyl)CH$_2$CH$_2$—, cyclohexyl-, (cyclohexyl)CH$_2$—, (cyclohexyl)CH$_2$CH$_2$—, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, morpholino)CH$_2$—, (N-piperidinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, or (N-piperidinyl)CH$_2$CH$_2$—;

R$^{11}$ is selected from H, methyl, ethyl, propyl, butyl, phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, 4-F-phenyl, 4-Cl-phenyl, 4-CH$_3$-phenyl, 4-CF$_3$-phenyl, 4-CH$_3$O-phenyl, 4-CF$_3$O-phenyl, 3-F-phenyl, 3-Cl-phenyl, 3-CH$_3$-phenyl, 3-CF$_3$-phenyl, 3-CH$_3$O-phenyl, 3-CF$_3$O-phenyl, 2-F-phenyl, 2-Cl-phenyl, 2-CH$_3$-phenyl, 2-CF$_3$-phenyl, 2-CH$_3$O-phenyl, 2-CF$_3$O-phenyl, (4-F-phenyl)methyl-, (4-Cl-phenyl)methyl-, (4-CH$_3$-phenyl)methyl-, (4-CF$_3$-phenyl)methyl-, (4-CH$_3$O-phenyl)methyl-, (4-CF$_3$O-phenyl)methyl-, (3-F-phenyl)methyl-, (3-Cl-phenyl)methyl-, (3-CH$_3$-phenyl)methyl-, (3-CF$_3$-phenyl)methyl-, (3-CH$_3$O-phenyl)methyl-, (3-CF$_3$O-phenyl)methyl-, (2-F-phenyl)methyl-, (2-Cl-phenyl)methyl-, (2-CH$_3$-phenyl)methyl-, (2-CF$_3$-phenyl)methyl-, (2-CH$_3$O-phenyl)methyl-, (2-CF$_3$O-phenyl)methyl-, 2-pyridyl-, 3-pyridyl-, 4-pyridyl-, 1-piperidinyl, 1-homopiperidinyl, and 1-morpholino; and $R^{13}$, at each occurrence, is independently selected from H, F, Cl, and methoxy.

7. A compound of claim 5 wherein:

Q is —$CH_3$, —$CH_2CH_3$, —$CH_2CH_2CH_3$, —$CH(CH_3)_2$, phenyl-, 2-F-phenyl-, 2-Cl-phenyl-, 2-Br-phenyl-, 2-$NO_2$-phenyl-, 2-$CH_3$-phenyl-, 2-$CH_3CH_2$-phenyl-, 2-$CH_3O$-phenyl-, 2-$CF_3$-phenyl-, 2-$CF_3O$-phenyl-, 2-$CH_3CONH$-phenyl, or 3,5-dimethyl-isoxazol-4-yl;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$,

W is a bond, —$CH_2$—, or —$CH(CH_3)$—;

X is a bond;

Y is a bond, —$CH_2$—V—, —V—, or —V—$CH_2$—;

V is a bond, —C(=O)—, —O—, —S—, —S(=O)—, —S(=O)$_2$—, —NH—, —N($CH_3$)—, —C(=O)NH—, or —NHC(=O)—, Z is H, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, —$CH_2C(CH_3)_3$, —$C(CH_3)_2CH_2CH_3$, —$CH(CH_3)CH(CH_3)_2$, —$CH_2CH_2CH_2CH_2CH_2CH_3$, —$CH(CH_3)CH_2CH_2CH_2CH_3$, —$CH_2CH(CH_3)CH_2CH_2CH_3$, —$CH_2CH_2CH(CH_3)CH_2CH_3$, —$CH_2CH_2CH_2CH(CH_3)_2$, —$CH_2CH(CH_2CH_3)_2$, —$CH_2CH_2C(CH_3)_3$, —$CH(CH_2CH_3)CH_2CH_2CH_3$, —$CF_3$, —$CH_2CF_3$, —$CH_2CH_2CF_3$, —$CH_2CH_2CH_2CF_3$, —$CH_2CH_2CH_2CH_2CF_3$, cyclopropyl-, (cyclopropyl)$CH_2$—, (cyclopropyl)$CH_2CH_2$—, cyclobutyl-, (cyclobutyl)$CH_2$—, (cyclobutyl)$CH_2CH_2$—, cyclopentyl-, (cyclopentyl)$CH_2$—, (cyclopentyl)$CH_2CH_2$—, cyclohexyl-, (cyclohexyl)$CH_2$—, (cyclohexyl)$CH_2CH_2$—, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3O$-phenyl, 3-$CF_3O$-phenyl, 4-$CF_3O$-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidinyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, (2-MeO-phenyl)$CH_2$—, (3-MeO-phenyl)$CH_2$—, (4-MeO-phenyl)$CH_2$—, (2-Me-phenyl)$CH_2$—, (3-Me-phenyl)$CH_2$—, (4-Me-phenyl)$CH_2$—, (2-MeS-phenyl)$CH_2$—, (3-MeS-phenyl)$CH_2$—, 4-MeS-phenyl)$CH_2$—, (2-$CF_3O$-phenyl)$CH_2$—, (3-$CF_3O$-phenyl)$CH_2$—, (4-$CF_3O$-phenyl)$CH_2$—, (furanyl)$CH_2$—, (thienyl)$CH_2$—, (pyridyl)$CH_2$—, (2-Me-pyridyl)$CH_2$—, (3-Me-pyridyl)$CH_2$—, (4-Me-pyridyl)$CH_2$—, (1-imidazolyl)$CH_2$—, (oxazolyl)$CH_2$—, (isoxazolyl)$CH_2$—, (1-benzimidazolyl)$CH_2$—, morpholino)$CH_2$—, (N-piperidinyl)$CH_2$—, phenyl-$CH_2CH_2$—, (phenyl)$_2CHCH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, (3-F-5-Cl-phenyl)$CH_2CH_2$—, (3-Cl-4-F-phenyl)$CH_2CH_2$—, (2-MeO-phenyl)$CH_2CH_2$—, (3-MeO-phenyl)$CH_2CH_2$—, (4-MeO-phenyl)$CH_2CH_2$—, (2-Me-phenyl)$CH_2CH_2$—, (3-Me-phenyl)$CH_2CH_2$—, (4-Me-phenyl)$CH_2CH_2$—, (2-MeS-phenyl)$CH_2CH_2$—, (3-MeS-phenyl)$CH_2CH_2$—, (4-MeS-phenyl)$CH_2CH_2$—, (2-$CF_3O$-phenyl)$CH_2CH_2$—, (3-$CF_3O$-phenyl)$CH_2CH_2$—, (4-$CF_3O$-phenyl)$CH_2CH_2$—, (furanyl)$CH_2CH_2$—, (thienyl)$CH_2CH_2$—, (pyridyl)$CH_2CH_2$—, (2-Me-pyridyl)$CH_2CH_2$—, (3-Me-pyridyl)$CH_2CH_2$—, (4-Me-pyridyl)$CH_2CH_2$—, (imidazolyl)$CH_2CH_2$—, (oxazolyl)$CH_2CH_2$—, (isoxazolyl)$CH_2CH_2$—, (benzimidazolyl)$CH_2CH_2$—, (cyclopropyl)$CH_2CH_2$—, (cyclobutyl)$CH_2CH_2$—, (cyclopentyl)$CH_2CH_2$—, (cyclohexyl)$CH_2CH_2$—, (morpholino)$CH_2CH_2$—, or (N-piperidinyl)$CH_2CH_2$—;

$R^{11}$ is selected from H, methyl, ethyl, propyl, butyl, phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, 4-F-phenyl, 4-Cl-phenyl, 4-$CH_3$-phenyl, 4-$CF_3$-phenyl, 4-$CH_3O$-phenyl, 4-$CF_3O$-phenyl, 3-F-phenyl, 3-Cl-phenyl, 3-$CH_3$-phenyl, 3-$CF_3$-phenyl, 3-$CH_3O$-phenyl, 3-$CF_3O$-phenyl, 2-F-phenyl, 2-Cl-phenyl, 2-$CH_3$-phenyl, 2-$CF_3$-phenyl, 2-$CH_3O$-phenyl, 2-$CF_3O$-phenyl, (4-F-phenyl)methyl-, (4-Cl-phenyl)methyl-, (4-$CH_3$-phenyl)methyl-, (4-$CF_3$-phenyl)methyl-, (4-$CH_3O$-phenyl)methyl-, (4-$CF_3O$-phenyl)methyl-, (3-F-phenyl)methyl-, (3-Cl-phenyl)methyl-, (3-$CH_3$-phenyl)methyl-, (3-$CF_3$-phenyl)methyl-, (3-$CH_3O$-phenyl)methyl-, (3-$CF_3O$-phenyl)methyl-, (2-F-phenyl)methyl-, (2-Cl-phenyl)methyl-, (2-$CH_3$-phenyl)methyl-, (2-$CF_3$-phenyl)methyl-, (2-$CH_3O$-phenyl)methyl-, (2-$CF_3O$-phenyl)methyl-, 2-pyridyl-, 3-pyridyl-, 4-pyridyl-, 1-piperidinyl, 1-homopiperidinyl, and 1-morpholino; and $R^{13}$, at each occurrence, is independently selected from H, F, Cl, and methoxy.

8. A compound, according to claim 1 or a pharmaceutically acceptable salt thereof, wherein $R^2$ is H, $R^{5a}$ is H, and $R^6$ is H.

9. A compound of claim 1 wherein $R^5$ is $OR^{14}$.

10. A compound of claim 1 wherein $R^5$ is $C_1$–$C_4$ alkoxy substituted with 0–3 $R^{5b}$.

11. A compound selected from:

2-(3,5-dimethyl-isoxazole-4-sulfonylamino)-4-methyl-pentanoic Acid (1-Methyl-2-oxo-5-phenyl-2,3-dihydro-1H-benzo[e][1,4]diazepin-3-yl)-amide;

2-(3,5-dimethyl-isoxazole-4-sulfonylamino)-N-(1-methyl-2-oxo-5-phenyl-2,3-dihydro-1H-benzo[e][1,4]diazepin-3-yl)-propionamide;

2-(3-bromo-5-chloro-thiophene-2-sulfonylamino)-4-methyl-pentanoic Acid (1-Methyl-2-oxo-5-phenyl-2,3-dihydro-1H-benzo[e][1,4]diazepin-3-yl)-amide;

2-(naphthalene-1-sulfonylamino)-4-methyl-pentanoic acid (1-methyl-2-oxo-5-phenyl-2,3-dihydro-1H-benzo[e][1,4]diazepin-3-yl)-amide;

2-(5-dimethylamino naphthalene-1-sulfonylamino)-4-methyl-pentanoic acid (1-Methyl-2-oxo-5-phenyl-2,3-dihydro-1H-benzo[e][1,4]diazepin-3-yl)-amide;

2-(naphthalene-2-sulfonylamino)-4-methyl-pentanoic acid (1-methyl-2-oxo-5-phenyl-2,3-dihydro-1H-benzo[e][1,4]diazepin-3-yl)-amide;

2-(2-acetamido-4-methylthiazole-5-sulfonylamino)-4-methyl-pentanoic acid (1-Methyl-2-oxo-5-phenyl-2,3-dihydro-1H-benzo[e][1,4]diazepin-3-yl)-amide;

2-(thiophene-2-sulfonylamino)-4-methyl-pentanoic acid (1-methyl-2-oxo-5-phenyl-2,3-dihydro-1H-benzo[e][1,4]diazepin-3-yl)-amide;

2-(quinoline-8-sulfonylamino)-4-methyl-pentanoic acid (1-methyl-2-oxo-5-phenyl-2,3-dihydro-1H-benzo[e][1,4]diazepin-3-yl)-amide;

2-(phenyl-sulfonylamino)-4-methyl-pentanoic acid (1-methyl-2-oxo-5-phenyl-2,3-dihydro-1H-benzo[e][1,4]diazepin-3-yl)-amide;

2-(2,5-dichlorophenyl sulfonylamino)-4-methyl-pentanoic acid (1-Methyl-2-oxo-5-phenyl-2,3-dihydro-1H-benzo[e][1,4]diazepin-3-yl)-amide;

2-(mesitylene-2-sulfonylamino)-4-methyl-pentanoic acid (1-methyl-2-oxo-5-phenyl-2,3-dihydro-1H-benzo[e][1,4]diazepin-3-yl)-amide;

2-(3-nitrophenyl-sulfonylamino)-4-methyl-pentanoic acid (1-methyl-2-oxo-5-phenyl-2,3-dihydro-1H-benzo[e][1,4]diazepin-3-yl)-amide;

2-(4-bromophenyl-sulfonylamino)-4-methyl-pentanoic acid (1-methyl-2-oxo-5-phenyl-2,3-dihydro-1H-benzo[e][1,4]diazepin-3-yl)-amide;

2-(4-fluorophenyl-sulfonylamino)-4-methyl-pentanoic acid (1-methyl-2-oxo-5-phenyl-2,3-dihydro-1H-benzo[e][1,4]diazepin-3-yl)-amide;

2-(4-chlorophenyl-sulfonylamino)-4-methyl-pentanoic acid (1-methyl-2-oxo-5-phenyl-2,3-dihydro-1H-benzo[e][1,4]diazepin-3-yl)-amide;

2-(4-acetamidophenyl-sulfonylamino)-4-methyl-pentanoic acid (1-methyl-2-oxo-5-phenyl-2,3-dihydro-1H-benzo[e][1,4]diazepin-3-yl)-amide;

2-(4-nitrophenyl-sulfonylamino)-4-methyl-pentanoic acid (1-methyl-2-oxo-5-phenyl-2,3-dihydro-1H-benzo[e][1,4]diazepin-3-yl)-amide;

2-(4-methoxyphenyl-sulfonylamino)-4-methyl-pentanoic acid (1-methyl-2-oxo-5-phenyl-2,3-dihydro-1H-benzo[e][1,4]diazepin-3-yl)-amide;

2-(4-tert-butylphenyl-sulfonylamino)-4-methyl-pentanoic acid (1-Methyl-2-oxo-5-phenyl-2,3-dihydro-1H-benzo[e][1,4]diazepin-3-yl)-amide;

2-(p-toluene-sulfonylamino)-4-methyl-pentanoic acid (1-methyl-2-oxo-5-phenyl-2,3-dihydro-1H-benzo[e][1,4]diazepin-3-yl)-amide;

2-(benzyl-sulfonylamino)-4-methyl-pentanoic acid (1-methyl-2-oxo-5-phenyl-2,3-dihydro-1H-benzo[e][1,4]diazepin-3-yl)-amide;

2-(beta-styrene-sulfonylamino)-4-methyl-pentanoic acid (1-methyl-2-oxo-5-phenyl-2,3-dihydro-1H-benzo[e][1,4]diazepin-3-yl)-amide;

2-((2-methoxycarbonyl)phenyl-sulfonylamino)-4-methyl-pentanoic Acid (1-Methyl-2-oxo-5-phenyl-2,3-dihydro-1H-benzo[e][1,4]diazepin-3-yl)-amide;

2-(2-nitro-4-(trifluoromethyl)phenyl-sulfonylamino)-4-methyl-pentanoic acid (1-Methyl-2-oxo-5-phenyl-2,3-dihydro-1H-benzo[e][1,4]diazepin-3-yl)-amide;

2-(3-(trifluoromethyl)phenyl-sulfonylamino)-4-methyl-pentanoic acid (1-Methyl-2-oxo-5-phenyl-2,3-dihydro-1H-benzo[e][1,4]diazepin-3-yl)-amide;

2-(2,5-dimethoxyphenyl-sulfonylamino)-4-methyl-pentanoic acid (1-Methyl-2-oxo-5-phenyl-2,3-dihydro-1H-benzo[e][1,4]diazepin-3-yl)-amide;

2-(2-methylphenyl-sulfonylamino)-4-methyl-pentanoic acid (1-methyl-2-oxo-5-phenyl-2,3-dihydro-1H-benzo[e][1,4]diazepin-3-yl)-amide;

2-(3,4-dichlorophenyl-sulfonylamino)-4-methyl-pentanoic acid (1-Methyl-2-oxo-5-phenyl-2,3-dihydro-1H-benzo[e][1,4]diazepin-3-yl)-amide;

2-(4-(trifluoromethoxy)phenyl-sulfonylamino)-4-methyl-pentanoic acid (1-Methyl-2-oxo-5-phenyl-2,3-dihydro-1H-benzo[e][1,4]diazepin-3-yl)-amide;

2-(3,4-dimethoxyphenyl-sulfonylamino)-4-methyl-pentanoic acid (1-Methyl-2-oxo-5-phenyl-2,3-dihydro-1H-benzo[e][1,4]diazepin-3-yl)-amide;

2-(2-bromophenyl-sulfonylamino)-4-methyl-pentanoic acid (1-methyl-2-oxo-5-phenyl-2,3-dihydro-1H-benzo[e][1,4]diazepin-3-yl)-amide;

2-(3,5-bis(trifluoromethylphenyl-2-sulfonylamino)-4-methyl-pentanoic acid (1-Methyl-2-oxo-5-phenyl-2,3-dihydro-1H-benzo[e][1,4]diazepin-3-yl)-amide;

2-(4-ethylphenyl-sulfonylamino)-4-methyl-pentanoic acid (1-methyl-2-oxo-5-phenyl-2,3-dihydro-1H-benzo[e][1,4]diazepin-3-yl)-amide;

2-(4-isopropylphenyl-sulfonylamino)-4-methyl-pentanoic acid (1-Methyl-2-oxo-5-phenyl-2,3-dihydro-1H-benzo[e][1,4]diazepin-3-yl)-amide;

2-(2,5-dichlorothiophene-3-sulfonylamino)-4-methyl-pentanoic acid (1-Methyl-2-oxo-5-phenyl-2,3-dihydro-1H-benzo[e][1,4]diazepin-3-yl)-amide;

2-(5-chlorothiophene-2-sulfonylamino)-4-methyl-pentanoic Acid (1-Methyl-2-oxo-5-phenyl-2,3-dihydro-1H-benzo[e][1,4]diazepin-3-yl)-amide;

2-(2-(trifluoromethyl)phenyl-sulfonylamino)-4-methyl-pentanoic acid (1-Methyl-2-oxo-5-phenyl-2,3-dihydro-1H-benzo[e][1,4]diazepin-3-yl)-amide;

2-(3-methylphenyl-sulfonylamino)-4-methyl-pentanoic acid (1-methyl-2-oxo-5-phenyl-2,3-dihydro-1H-benzo[e][1,4]diazepin-3-yl)-amide;

2-(2,3-dichlorothiophene-5-sulfonylamino)-4-methyl-pentanoic Acid (1-Methyl-2-oxo-5-phenyl-2,3-dihydro-1H-benzo[e][1,4]diazepin-3-yl)-amide;

2-(4-bromo-5-chlorothiophene-2-sulfonylamino)-4-methyl-pentanoic acid (1-Methyl-2-oxo-5-phenyl-2,3-dihydro-1H-benzo[e][1,4]diazepin-3-yl)-amide;

2-(5-[(benzoylamino)methyl]-thiophene-2-sulfonylamino)-4-methyl-pentanoic acid (1-Methyl-2-oxo-5-phenyl-2,3-dihydro-1H-benzo[e][1,4]diazepin-3-yl)-amide;

2-(4-phenylsulfonylthiophene-2-sulfonylamino)-4-methyl-pentanoic acid (1-Methyl-2-oxo-5-phenyl-2,3-dihydro-1H-benzo[e][1,4]diazepin-3-yl)-amide;

2-(5-(phenylsulfonyl)thiophene-2-sulfonylamino)-4-methyl-pentanoic acid (1-methyl-2-oxo-5-phenyl-2,3-dihydro-1H-benzo[e][1,4]diazepin-3-yl)-amide;

2-[2-(1-methyl-(5-trifluoromethyl)pyrazole)thiophene-5-sulfonylamino]-4-methyl-pentanoic acid (1-Methyl-2-oxo-5-phenyl-2,3-dihydro-1H-benzo[e][1,4]diazepin-3-yl)-amide;

2-(5-(2-pyridyl)thiophene-2-sulfonylamino)-4-methyl-pentanoic acid (1-Methyl-2-oxo-5-phenyl-2,3-dihydro-1H-benzo[e][1,4]diazepin-3-yl)-amide;

2-2-(3,5-dimethyl-isoxazole-4-sulfonylamino)-4-methyl-pentanoic acid [5-(4-fluoro-phenyl)-1-methyl-2-oxo-2,3-dihydro-1H-benzo[e][1,4]diazepin-3-yl]-amide;

2-(3,5-dimethyl-isoxazole-4-sulfonylamino)-N-[5-(4-fluoro-phenyl)-1-methyl-2-oxo-2,3-dihydro-1H-benzo[e][1,4]diazepin-3-yl]-propionamide;

2-(2-fluoro-benzenesulfonylamino)-N-[5-(4-fluoro-phenyl)-1-methyl-2-oxo-2,3-dihydro-1H-benzo[e][1,4]diazepin-3-yl]-propionamide;

N-(1-methyl-2-oxo-5-phenyl-2,3-dihydro-1H-benzo[e][1,4]diazepin-3-yl)-2-(2-trifluoromethyl-benzenesulfonylamino)-propionamide;

2-(2-fluoro-benzenesulfonylamino)-4-methyl-pentanoic acid(1-methyl-2-oxo-5-phenyl-2,3-dihydro-1H-benzo[e][1,4]diazepin-3-yl)-amide;

4-methyl-2-(2-trifluoromethyl-benzenesulfonylamino)-pentanoic acid (1-Methyl-2-oxo-5-phenyl-2,3-dihydro-1H-benzo[e][1,4]diazepin-3-yl)-amide;

4-methyl-2-(propane-1-sulfonylamino)-pentanoic acid (1-methyl-2-oxo-5-phenyl-2,3-dihydro-1H-benzo[e][1,4]diazepin-3-yl)-amide;

4-methyl-2-(propane-1-sulfonylamino)-pentanoic acid (1-methyl-2-oxo-5-phenyl-2,3-dihydro-1H-benzo[e][1,4]diazepin-3-yl)-amide;

2-(3,5-dimethyl-isoxazole-4-sulfonylamino)-N-[1-methyl-2-oxo-5-(4-trifluoromethyl-phenyl)-2,3-dihydro-1H-benzo[e][1,4]diazepin-3-yl]-propionamide;

2-(3,5-dimethyl-isoxazole-4-sulfonylamino)-4-methyl-pentanoic acid (7-chloro-1-methyl-2-oxo-5-phenyl-2,3-dihydro-1H-benzo[e][1,4]diazepin-3-yl)-amide;

4-methyl-2-(propane-1-sulfonylamino)-pentanoic acid [5-(4-chloro-phenyl)-1-methyl-2-oxo-2,3-dihydro-1H-benzo[e][1,4]diazepin-3-yl]-amide;

2-(3,5-dimethyl-isoxazole-4-sulfonylamino)-4-methyl-pentanoic acid (1-Methyl-2-oxo-5-pyridin-2-yl-2,3-dihydro-1H-benzo[e][1,4]diazepin-3-yl)-amide;

2-[(3,5-dimethyl-isoxazole-4-sulfonyl)-methyl-amino]-N-(1-methyl-2-oxo-5-phenyl-2,3-dihydro-1H-benzo[e][1,4]diazepin-3-yl)-propionamide;

3-dimethylamino-2-(3,5-dimethyl-isoxazole-4-sulfonylamino)-N-(1-methyl-2-oxo-5-phenyl-2,3-dihydro-1H-benzo[e][1,4]diazepin-3-yl)-propionamide;

N-[1-methyl-2-oxo-5-(4-trifluoromethyl-phenyl)-2,3-dihydro-1H-benzo[e][1,4]diazepin-3-yl]-2-(propane-1-sulfonylamino)-propionamide;

N-(7-chloro-1-methyl-2-oxo-5-phenyl-2,3-dihydro-1H-benzo[e][1,4]diazepin-3-yl)-2-(3,5-dimethyl-isoxazole-4-sulfonylamino)-propionamide;

2-(3,5-dimethyl-isoxazole-4-sulfonylamino)-4-methyl-pentanoic acid [5-(4-chloro-phenyl)-1-methyl-2-oxo-2,3-dihydro-1H-benzo[e][1,4]diazepin-3-yl]-amide; and 2-methanesulfonylamino-N-[1-methyl-2-oxo-5-(4-trifluoromethyl-phenyl)-2,3-dihydro-1H-benzo[e][1,4]diazepin-3-yl]-propionamide.

12. A compound of claim 1 of Formula (I):

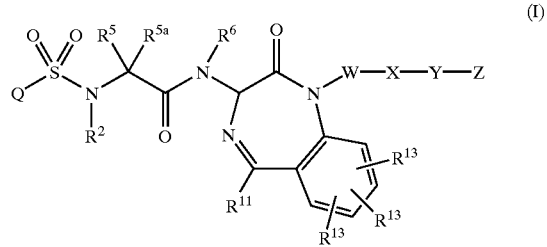

(I)

or a pharmaceutically acceptable salt form thereof, wherein:

Q is $C_1-C_6$ alkyl substituted with 0–3 $R^{1a}$;
$C_3-C_{10}$ cycloalkyl substituted with 0–3 $R^{1b}$;
aryl substituted with 0–3 $R^{1b}$; or
5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1a}$, at each occurrence, is independently selected from H, Cl, F, Br, $NR^{19}R^{20}$, $CF_3$, $C_1-C_4$ alkyl; $C_1-C_4$ haloalkyl; aryl substituted with 0–3 $R^{1b}$; and
5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1b}$, at each occurrence, is independently selected from H, $OR^{14}$, Cl, F, Br, $NO_2$, $NR^{19}R^{20}$, $CF_3$, $OCF_3$, $C_1-C_4$ alkoxy, $C_1-C_4$ haloalkoxy;
—C(=O)—$R^{1d}$, —O—$R^{1d}$, —S—$R^{1d}$, —S(=O)—$R^{1d}$, —S(=O)$_2$—$R^{1d}$, —N($R^{19}$)—$R^{1d}$, —C(=O)NR$^{19b}$R$^{1d}$, —NR$^{19b}$C(=O)—$R^{1d}$, NR$^{19b}$S(=O)$_2$—$R^{1d}$, —S(=O)$_2$NR$^{19b}$—$R^{1d}$, —NR$^{19b}$S(=O)—$R^{1d}$, —S(=O)NR$^{19b}$—$R^{1d}$, —C(=O) O—$R^{1d}$, —OC(=O)—$R^{1d}$;
$C_1-C_6$ alkyl substituted with 0–3 $R^{1c}$;
$C_3-C_{10}$ cycloalkyl substituted with 0–3 $R^{1f}$;
aryl substituted with 0–3 $R^{1f}$; and 5 to 14 membered heterocycle containing 1 to 4 heteroatoms selected from nitrogen, oxygen, and sulphur, wherein said 5 to 14 membered heterocycle is substituted with 0–3 $R^{1f}$;

$R^{1c}$, at each occurrence, is independently selected from H, $OR^{14}$, Cl, F, Br, $NO_2$, $NR^{19}R^{20}$, $CF_3$, $C_1-C_4$ alkoxy, $C_1-C_4$ haloalkoxy; —C(=O)—$R^{1d}$, O—$R^{1d}$, —S—$R^{1d}$, —S(=O)—$R^{1d}$, —S(=O)$_2$—$R^{1d}$, —N($R^{19}$)—$R^{1d}$, —C(=O)NR$^{19b}$R$^{1d}$, —NR$^{19b}$C(=O)—$R^{1d}$, —NR$^{19b}$S(=O)$_2$—$R^{1d}$, —S(=O)$_2$NR$^{19b}$—$R^{1d}$, —NR$^{19b}$S(=O)—$R^{1d}$, —S(=O)NR$^{19b}$—$R^{1d}$, —C(=O)O—$R^{1d}$, —OC(=O)—$R^{1d}$;
$C_3-C_{10}$ cycloalkyl substituted with 0–3 $R^{1f}$;
$C_3-C_{10}$ carbocycle substituted with 0–3 $R^{1f}$;
aryl substituted with 0–3 $R^{1f}$; and
5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1d}$, at each occurrence, is independently selected from H, $C_1-C_6$ alkyl, and aryl substituted with 0–3 $R^{1f}$;

$R^{1f}$, at each occurrence, is independently selected from H, Cl, F, Br, $NO_2$, $CF_3$, $C_1-C_4$ alkyl, $C_1-C_4$ haloalkyl, $C_1$–$C_4$ alkoxy, $C_1$–$C_4$ haloalkoxy, and $C_1$–$C_4$ haloalkyl-S—;

$R^2$ is H, methyl, or ethyl;

$R^5$ is $C_1$–$C_6$ alkyl substituted with 0–3 $R^{5b}$;
  $C_2$–$C_6$ alkenyl substituted with 0–3 $R^{5b}$; or
  $C_2$–$C_6$ alkynyl substituted with 0–3 $R^{5b}$;

$R^{5a}$ is H or $C_1$–$C_4$ alkyl;

$R^{5b}$, at each occurrence, is independently selected from:
  H, $C_1$–$C_6$ alkyl, $CF_3$, $OR^{14}$, Cl, F, Br, I, =O, CN, $NO_2$, $NR^{15}R^{16}$, acetyl, —S($C_1$–$C_4$ alkyl), S(=O)($C_1$–$C_4$ alkyl), S(=O)$_2$($C_1$–$C_4$ alkyl);
  $C_3$–$C_{10}$ cycloalkyl substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^6$ is H, methyl or ethyl;

$R^{11}$ is selected from
  H, $C_1$–$C_4$ alkoxy, Cl, F, Br, I, CN, $NO_2$, $NR^{18}R^{19}$, $CF_3$;
  $C_1$–$C_6$ alkyl substituted with 0–1 $R^{11a}$;
  aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, phenyl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

W is a bond;
X is a bond;
Y is a bond;
Z is H;
  $C_1$–$C_6$ alkyl substituted with 0–2 $R^{12}$;
  $C_2$–$C_6$ alkenyl substituted with 0–2 $R^{12}$;
  $C_2$–$C_6$ alkynyl substituted with 0–2 $R^{12}$;
  phenyl substituted with 0–4 $R^{12}b$;
  $C_3$–$C_6$ carbocycle substituted with 0–4 $R^{12}b$; or
  5 to 10 membered heterocycle containing 1 to 4 heteroatoms selected from nitrogen, oxygen, and sulphur, wherein said 5 to 10 membered heterocycle is substituted with 0–3 $R^{12}b$;

$R^{12}$ is phenyl substituted with 0–4 $R^{12}b$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12}b$;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, OH, $C_1$–$C_4$ alkyl, $C_1$–$C_4$ alkoxy, Cl, F, Br, CN, $NO_2$, and $CF_3$;

$R^{14}$, at each occurrence, is independently selected from H, phenyl, benzyl, $C_1$–$C_6$ alkyl, or $C_2$–$C_6$ alkoxyalkyl;

$R^{15}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_1$–$C_6$ alkyl);

$R^{16}$, at each occurrence, is independently selected from H, OH, $C_1$–$C_6$ alkyl, phenyl, benzyl, phenethyl, —C(=O)—($C_{1-6}$ alkyl) and —S(=O)$_2$—($C_1$–$C_6$ alkyl);

alternatively, —$NR^{15}R^{16}$ may be a heterocyclic ring selected from the group piperidinyl, morpholinyl, thiomorpholinyl, pyrrolidinyl, homopiperidinyl, piperazinyl, and N-methylpiperizinyl;

$R^{18}$, at each occurrence, is independently selected from H, $C_1$–$C_6$ alkyl, phenyl, benzyl, phenethyl, —C(=O)—($C_1$–$C_6$ alkyl) and —S(=O)$_2$—($C_{1-6}$ alkyl);

$R^{19}$, at each occurrence, is independently selected from H, OH, $C_1$–$C_6$ alkyl, phenyl, benzyl, phenethyl, —C(=O)—($C_{1-6}$ alkyl) and —S(=O)$_2$—($C_1$–$C_6$ alkyl); and $R^{20}$ is H or $C_1$–$C_4$.

13. A compound of claim 12 of Formula (Ia)

(Ia)

wherein:

Q is $C_1$–$C_6$ alkyl substituted with 0–1 $R^{1a}$;
  phenyl substituted with 0–3 $R^{1b}$;
  naphthyl substituted with 0–3 $R^{1b}$; or
  5 to 10 membered heterocycle containing 1 to 2 heteroatoms selected from nitrogen, oxygen, and sulphur, wherein said 5 to 10 membered heterocycle is substituted with 0–3 $R^{1b}$;

$R^{1a}$, at each occurrence, is independently selected from H, Cl, F, Br, —$NR^{19}R^{20}$, —$CF_3$; and
  phenyl substituted with 0–3 $R^{1b}$;

$R^{1b}$, at each occurrence, is independently selected from H, methyl, ethyl, $OR^{14}$, Cl, F, Br, $NO_2$, $NR^{19}R^{20}$, $CF_3$, $OCF_3$, $C_1$–$C_4$ alkoxy, $C_1$–$C_4$ haloalkoxy;
  —C(=O)—$R^{1d}$, —O—$R^{1d}$, —S(=O)$_2$—$R^{1d}$, —N($R^{19}$)—$R^{1d}$, —C(=O)$NR^{19b}R^{1d}$, —$NR^{19b}$C(=O)—$R^{1d}$, —$NR^{19b}$S(=O)$_2$—$R^{1d}$, —S(=O)$_2$$NR^{19b}$—$R^{1d}$, —C(=O)O—$R^{1d}$, —OC(=O)—$R^{1d}$;
  $C_1$–$C_6$ alkyl substituted with 0–3 $R^{1c}$;
  phenyl substituted with 0–3 $R^{1f}$; and
  5 to 10 membered heterocycle containing 1 to 4 heteroatoms selected from nitrogen, oxygen, and sulphur, wherein said 5 to 10 membered heterocycle is substituted with 0–3 $R^{1f}$;

$R^{1c}$, at each occurrence, is independently selected from H, —C(=O)—$R^{1d}$, —O—$R^{1d}$, —S—$R^{1d}$, —S(=O)—

$R^{1d}$, —S(=O)$_2$—$R^{1d}$, —N($R^{19}$)—$R^{1d}$, —C(=O)NR$^{19b}$R$^{1d}$, —NR$^{19b}$C(=O)—$R^{1d}$, —NR$^{19b}$S(=O)$_2$—$R^{1d}$, and —S(=O)$_2$NR$^{19b}$—$R^{1d}$;

$R^{1d}$, at each occurrence, is independently selected from H, $C_1$–$C_6$ alkyl; and phenyl substituted with 0–3 $R^{1f}$;

$R^{1f}$, at each occurrence, is independently selected from H, Cl, F, Br, NO$_2$, CF$_3$, methyl, ethyl, propyl, methoxy, ethoxy, propoxy, $C_1$–$C_2$ haloalkyl, and $C_1$–$C_2$ haloalkoxy;

$R^5$ is $C_1$–$C_4$ alkyl substituted with 0–1 $R^{5b}$;

$R^{5b}$, at each occurrence, is independently selected from: H, methyl, ethyl, propyl, butyl, —NR$^{15}$R$^{16}$; $C_3$–$C_7$ cycloalkyl substituted with 0–3 $R^{5c}$; phenyl substituted with 0–3 $R^{5c}$; or
5 to 7 membered heterocycle containing 1 to 4 heteroatoms selected from nitrogen, oxygen, and sulphur, wherein said 5 to 7 membered heterocycle is substituted with 0–3 $R^{5c}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{5c}$, at each occurrence, is independently selected from H, OH, Cl, F, —NR$^{15}$R$^{16}$, CF$_3$, acetyl, SCH$_3$, S(=O)$_2$CH$_3$, methyl, and methoxy;

$R^{11}$ is selected from H, NR$^{18}$R$^{19}$, CF$_3$; $C_1$–$C_6$ alkyl substituted with 0–1 $R^{11a}$; phenyl substituted with 0–3 $R^{11b}$; $C_3$–$C_6$ carbocycle substituted with 0–3 $R^{11b}$; or
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11a}$, at each occurrence, is independently selected from H, methyl, ethyl, propyl, butyl, methoxy, ethoxy, propoxy, Cl, F, Br, CN, NO$_2$, NR$^{15}$R$^{16}$, CF$_3$, phenyl substituted with 0–3 $R^{11b}$; $C_3$–$C_6$ carbocycle substituted with 0–3 $R^{11b}$; or
5 to 7 membered heterocycle containing 1 to 4 heteroatoms selected from nitrogen, oxygen, and sulphur, wherein said 5 to 7 membered heterocycle is substituted with 0–3 $R^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

$R^{11b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, $C_1$–$C_2$ haloalkyl, and $C_1$–$C_2$ haloalkoxy;

W is a bond;
X is a bond;
Y is a bond;
Z is H;
$C_1$–$C_6$ alkyl substituted with 0–2 $R^{12}$;
$C_2$–$C_6$ alkenyl substituted with 0–2 $R^{12}$;
$C_2$–$C_6$ alkynyl substituted with 0–2 $R^{12}$;

phenyl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ is phenyl substituted with 0–4 $R^{12b}$; $C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{13}$, at each occurrence, is independently selected from H, methyl, ethyl, methoxy, ethoxy, Cl, F, Br, NO$_2$, or CF$_3$;

$R^{14}$, at each occurrence, is independently selected from H, phenyl, benzyl, $C_1$–$C_4$ alkyl, or $C_2$–$C_4$ alkoxyalkyl;

$R^{15}$, at each occurrence, is independently selected from H, methyl, ethyl, propyl, butyl, phenyl, benzyl, and phenethyl;

$R^{16}$, at each occurrence, is independently selected from H, OH, methyl, ethyl, propyl, butyl, phenyl, benzyl, phenethyl, CH$_3$CH$_2$C(=O)—, CH$_3$C(=O)—, CH$_3$CH$_2$OC(=O)—, CH$_3$OC(=O)—, CH$_3$CH$_2$S(=O)$_2$ — and CH$_3$S(=O)$_2$—;

$R^{18}$, at each occurrence, is independently selected from H, methyl, ethyl, propyl, butyl, phenyl, benzyl, and phenethyl;

$R^{19}$, at each occurrence, is independently selected from H, OH, methyl, ethyl, propyl, and butyl; and $R^{20}$ is H, methyl, ethyl, propyl, or butyl.

14. A compound of claim 13 of Formula (Ia)

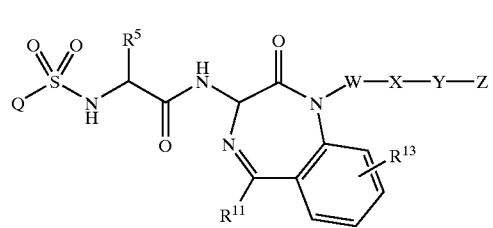

(Ia)

wherein:
Q is $C_1$–$C_4$ alkyl substituted with 0–1 $R^{1a}$;
phenyl substituted with 0–3 $R^{1b}$;
naphthyl substituted with 0–3 $R^{1b}$; or
5 to 10 membered heterocycle containing 1 to 2 heteroatoms selected from nitrogen, oxygen, and sulphur, wherein said 5 to 10 membered heterocycle is substituted with 0–3 $R^{1b}$; wherein said 5 to 10 membered heterocycle is selected from pyridinyl, quinolinyl, pyrimidinyl, triazinyl, furanyl, thienyl, thiazolyl, imidazolyl, oxazolyl, and isoxazolyl;

$R^{1a}$, at each occurrence, is independently selected from H, Cl, F, Br, CF$_3$, and phenyl substituted with 0–3 $R^{1b}$;

$R^{1b}$, at each occurrence, is independently selected from H, methyl, ethyl, OR$^{14}$, Cl, F, Br, NO$_2$, NR$^{19}$R$^{20}$, CF$_3$, OCF$_3$, $C_1$–$C_4$ alkoxy, $C_1$–$C_4$ haloalkoxy; —C(=O)—$R^{1d}$, —O—$R^{1d}$, —S(=O)$_2$—$R^{1d}$, —N($R^{19}$)—$R^{1d}$, —C(=O)NR$^{19b}$R$^{1d}$, —NR$^{19b}$C(=O)—$R^{1d}$, —NR$^{19b}$S(=O)$_2$—R$^{1d}$, —S(=O)$_2$NR$^{19b}$—R$^{1d}$, —C(=O)O—R$^{1d}$, —OC(=O)—R$^{1d}$;
C$_1$–C$_6$ alkyl substituted with 0–3 R$^{1c}$;
phenyl substituted with 0–3 R$^{1f}$; and
5 to 6 membered heterocycle containing 1 to 4 heteroatoms selected from nitrogen, oxygen, and sulphur, wherein said 5 to 6 membered heterocycle is substituted with 0–3 R$^{1f}$;

R$^{1c}$, at each occurrence, is independently selected from H, —C(=O)—R$^{1d}$, —O—R$^{1d}$, —S—R$^{1d}$, —S(=O)—R$^{1d}$, —S(=O)$_2$—R$^{1d}$, —N(R$^{19}$)—R$^{1d}$, —C(=O)NR$^{19b}$R$^{1d}$, —NR$^{19b}$C(=O)—R$^{1d}$, —NR$^{19b}$S(=O)$_2$—R$^{1d}$, and —S(=O)$_2$NR$^{19b}$—R$^{1d}$, R$^{1d}$, at each occurrence, is independently selected from H, C$_1$–C$_6$ alkyl; and phenyl substituted with 0–3 R$^{1f}$;

R$^{1f}$, at each occurrence, is independently selected from H, Cl, F, Br, NO$_2$, CF$_3$, —OCF$_3$, methyl, ethyl, methoxy, and ethoxy;

R$^5$ is methyl substituted with 0–1 R$^{5b}$;
ethyl substituted with 0–1 R$^{5b}$;
propyl substituted with 0–1 R$^{5b}$; or butyl substituted with 0–1 R$^{5b}$;

R$^{5b}$, at each occurrence, is independently selected from: H, methyl, ethyl, and NR$^{15}$R$^{16}$;

R$^{11}$ is selected from
H, NR$^{18}$R$^{19}$, CF$_3$;
C$_1$–C$_4$ alkyl substituted with 0–1 R$^{11a}$;
phenyl substituted with 0–3 R$^{11b}$;
C$_3$–C$_6$ carbocycle substituted with 0–3 R$^{11b}$; or
5 to 7 membered heterocycle containing 1 to 4 heteroatoms selected from nitrogen, oxygen, and sulphur, wherein said 5 to 7 membered heterocycle is substituted with 0–3 R$^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R$^{11a}$, at each occurrence, is independently selected from H, methyl, ethyl, propyl, butyl, methoxy, ethoxy, propoxy, Cl, F, NR$^{15}$R$^{16}$, CF$_3$;
phenyl substituted with 0–3 R$^{11b}$;
C$_3$–C$_6$ carbocycle substituted with 0–3 R$^{11b}$; or
5 to 7 membered heterocycle containing 1 to 4 heteroatoms selected from nitrogen, oxygen, and sulphur, wherein said 5 to 7 membered heterocycle is substituted with 0–3 R$^{11b}$; wherein said 5 to 7 membered heterocycle is selected from pyridinyl, pyrimidinyl, triazinyl, furanyl, thienyl, thiazolyl, pyrrolyl, piperazinyl, piperidinyl, homopiperidinyl, pyrazolyl, imidazolyl, oxazolyl, isoxazolyl, and tetrazolyl;

R$^{11b}$, at each occurrence, is independently selected from H, OH, Cl, F, NR$^{15}$R$^{16}$, CF$_3$, methyl, ethyl, propyl, methoxy, and ethoxy;

W is a bond;
X is a bond;
Y is a bond;
Z is H;
C$_1$–C$_6$ alkyl substituted with 0–2 R$^{12}$;
C$_2$–C$_6$ alkenyl substituted with 0–2 R$^{12}$;
C$_2$–C$_6$ alkynyl substituted with 0–2 R$^{12}$;
phenyl substituted with 0–4 R$^{12b}$;
C$_3$–C$_6$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12}$ is phenyl substituted with 0–4 R$^{12b}$;
C$_3$–C$_6$ carbocycle substituted with 0–4 R$^{12b}$; or
5 to 10 membered heterocycle containing 1 to 4 heteroatoms selected from nitrogen, oxygen, and sulphur, wherein said 5 to 10 membered heterocycle is substituted with 0–3 R$^{12b}$;

R$^{12b}$, at each occurrence, is independently selected from H, OH, Cl, F, Br, NR$^{15}$R$^{16}$, CF$_3$, OCF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

R$^{13}$, at each occurrence, is independently selected from H, methyl, methoxy, Cl, F, Br, and CF$_3$;

R$^{14}$, at each occurrence, is independently selected from H, phenyl, benzyl, methyl, ethyl, propyl, and butyl;

R$^{15}$, at each occurrence, is independently selected from H, methyl, ethyl, propyl, or butyl;

R$^{16}$, at each occurrence, is independently selected from H, OH, methyl, ethyl, propyl, butyl, phenyl, benzyl, and phenethyl;

R$^{18}$, at each occurrence, is independently selected from H, methyl, ethyl, propyl, butyl, phenyl, benzyl, and phenethyl;

R$^{19}$, at each occurrence, is independently selected from H, OH, methyl, ethyl, propyl, and butyl; and R$^{20}$ is H, methyl, ethyl, propyl, or butyl.

15. A compound of claim 13 wherein:

Q is —CH$_3$, —CH$_2$CH$_3$, —CH$_2$CH$_2$CH$_3$, —CH$_2$CH$_2$CH$_2$CH$_3$, —CH(CH$_3$)$_2$, —CH(CH$_3$)CH$_2$CH$_3$, —CH$_2$CH(CH$_3$)$_2$, —CH$_2$CF$_3$, —CH$_2$CH$_2$CF$_3$, —CH$_2$CH$_2$CH$_2$CF$_3$, phenyl-, 4-tBu-phenyl-, 4-iPr-phenyl-, 4-Et-phenyl-, 2-F-phenyl-, 3-F-phenyl-, 4-F-phenyl-, 2-Cl-phenyl-, 3-Cl-phenyl-, 4-Cl-phenyl-, 2-Br-phenyl-, 3-Br-phenyl-, 4-Br-phenyl-, 2-NO$_2$-phenyl-, 3-NO$_2$-phenyl-, 4-NO$_2$-phenyl-, 2-CH$_3$-phenyl-, 3-CH$_3$-phenyl-, 4-CH$_3$-phenyl-, 2-CH$_3$O-phenyl-, 3-CH$_3$O-phenyl-, 4-CH$_3$O-phenyl-, 2-CF$_3$-phenyl-, 3-CF$_3$-phenyl-, 4-CF$_3$-phenyl-, 2-CF$_3$O-phenyl-, 3-CF$_3$O-phenyl-, 4-CF$_3$O-phenyl-, 2-CH$_3$CONH-phenyl, 3-CH$_3$CONH-phenyl, 4-CH$_3$CONH-phenyl, 2-methyoxycarbonyl-phenyl-, 4-phenyl-phenyl-, 2,3-diF-phenyl-, 2,4-diF-phenyl-, 2,5-diF-phenyl-, 2,6-diF-phenyl-, 3,4-diF-phenyl-, 3,5-diF-phenyl-, 2,3-diCl-phenyl-, 2,4-diCl-phenyl-, 2,5-diCl-phenyl-, 2,6-diCl-phenyl-, 3,4-diCl-phenyl-, 3,5-diCl-phenyl-, 3-F-4-Cl-phenyl-, 3-F-5-Cl-phenyl-, 3-Cl-4-F-phenyl-, 2,3-diMe-phenyl-, 2,4-diMe-phenyl-, 2,5-diMe-phenyl-, 2,6-diMe-phenyl-, 3,4-diMe-phenyl-, 3,5-diMe-phenyl-, 2,3-diMeO-phenyl-, 2,4-diMeO-phenyl-, 2,5-diMeO-phenyl-, 2,6-diMeO-phenyl-, 3,4-diMeO-phenyl-, 3,5-diMeO-phenyl-, 2,3-diCF$_3$-phenyl-, 2,4-diCF$_3$-phenyl-, 2,5-diCF$_3$-phenyl-, 2,6-diCF$_3$-phenyl-, 3,4-diCF$_3$-phenyl-, 3,5-diCF$_3$-phenyl-, 2-NO$_2$-4-CF$_3$-phenyl-, 2-Me-5-Cl-phenyl-, 2,4,6-triMe-phenyl, benzyl-, naphth-1-yl-, naphth-2-yl-, beta-styrene-, furanyl-, thienyl-, pyridyl-, thiazolyl-, imidazol-1-yl-, oxazolyl-, isoxazolyl-, quinolin-8-yl-, 3-methyl-isoxazol-4-yl-, 3,5-dimethyl-isoxazol-4-yl-, 3-bromo-5-chloro-thiophen-2-yl-, 2,3-dichlorothiophen-5-yl-, 4-bromo-5-chlorothiophen-2-yl-, 5-[(benzoylamino)methyl]-thiophen-2-yl-, 4-phenylsulfonylthiophen-2-yl-, 5-(phenylsulfonyl)thiophen-2-yl-, 2-(1-methyl-(5-trifluoromethyl)

pyrazole)thiophen-5-yl-, 5-(2-pyridyl)thiophen-2-yl-, 1-methyl-5-(trifluoromethyl)imidazol-3-yl-, 2-(2-methylthio-pyrimdin-3-yl)-thiophen-5-yl-, or dibenzofuran-2-yl-;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, or (3-$CH_3$-cyclobutyl)$CH_2CH_2$—;

W is a bond;

X is a bond;

Y is a bond;

Z is H, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, —$CH_2C(CH_3)_3$, —$C(CH_3)_2CH_2CH_3$, —$CH(CH_3)CH(CH_3)_2$, —$CH_2CH_2CH_2CH_2CH_2CH_3$, —$CH(CH_3)CH_2CH_2CH_2CH_3$, —$CH_2CH(CH_3)CH_2CH_2CH_3$, —$CH_2CH_2CH(CH_3)CH_2CH_3$, —$CH_2CH_2CH_2CH(CH_3)_2$, —$CH_2CH(CH_2CH_3)_2$, —$CH_2CH_2C(CH_3)_3$, —$CH(CH_2CH_3)CH_2CH_2CH_3$, —$CF_3$, —$CH_2CF_3$, —$CH_2CH_2CF_3$, —$CH_2CH_2CH_2CF_3$, —$CH_2CH_2CH_2CH_2CF_3$, cyclopropyl-, (cyclopropyl)$CH_2$—, (cyclopropyl)$CH_2CH_2$—, cyclobutyl-, (cyclobutyl)$CH_2$—, (cyclobutyl)$CH_2CH_2$—, cyclopentyl-, (cyclopentyl)$CH_2$—, (cyclopentyl)$CH_2CH_2$—, cyclohexyl-, (cyclohexyl)$CH_2$—, (cyclohexyl)$CH_2CH_2$—, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-$CF_3$O-phenyl, 3-$CF_3$O-phenyl, 4-$CF_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidinyl, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, (2-MeO-phenyl)$CH_2$—, (3-MeO-phenyl)$CH_2$—, (4-MeO-phenyl)$CH_2$—, (2-Me-phenyl)$CH_2$—, (3-Me-phenyl)$CH_2$—, (4-Me-phenyl)$CH_2$—, (2-MeS-phenyl)$CH_2$—, (3-MeS-phenyl)$CH_2$—, 4-MeS-phenyl)$CH_2$—, (2-$CF_3$O-phenyl)$CH_2$—, (3-$CF_3$O-phenyl)$CH_2$—, (4-$CF_3$O-phenyl)$CH_2$—, (furanyl)$CH_2$—, (thienyl)$CH_2$—, (pyridyl)$CH_2$—, (2-Me-pyridyl)$CH_2$—, (3-Me-pyridyl)$CH_2$—, (4-Me-pyridyl)$CH_2$—, (1-imidazolyl)$CH_2$—, (oxazolyl)$CH_2$—, (isoxazolyl)$CH_2$—, (1-benzimidazolyl)$CH_2$—, morpholino)$CH_2$—, (N-piperidinyl)$CH_2$—, phenyl-$CH_2CH_2$—, (phenyl)$_2$CHCH$_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, (3-F-5-Cl-phenyl)$CH_2CH_2$—, (3-Cl-4-F-phenyl)$CH_2CH_2$—, (2-MeO-phenyl)$CH_2CH_2$—, (3-MeO-phenyl)$CH_2CH_2$—, (4-MeO-phenyl)$CH_2CH_2$—, (2-Me-phenyl)$CH_2CH_2$—, (3-Me-phenyl)$CH_2CH_2$—, (4-Me-phenyl)$CH_2CH_2$—, (2-MeS-phenyl)$CH_2CH_2$—, (3-MeS-phenyl)$CH_2CH_2$—, (4-MeS-phenyl)$CH_2CH_2$—, (2-$CF_3$O-phenyl)$CH_2CH_2$—, (3-$CF_3$O-phenyl)$CH_2CH_2$—, (4-$CF_3$O-phenyl)$CH_2CH_2$—, (furanyl)$CH_2CH_2$—, (thienyl)$CH_2CH_2$—, (pyridyl)$CH_2CH_2$—, (2-Me-pyridyl)$CH_2CH_2$—, (3-Me-pyridyl)$CH_2CH_2$—, (4-Me-pyridyl)$CH_2CH_2$—, (imidazolyl)$CH_2CH_2$—, (oxazolyl)$CH_2CH_2$—, (isoxazolyl)$CH_2CH_2$—, (benzimidazolyl)$CH_2CH_2$—, (cyclopropyl)$CH_2CH_2$—, (cyclobutyl)$CH_2CH_2$—, (cyclopentyl)$CH_2CH_2$—, (cyclohexyl)$CH_2CH_2$—, (morpholino)$CH_2CH_2$—, or (N-piperidinyl)$CH_2CH_2$—;

$R^{11}$ is selected from H, methyl, ethyl, propyl, butyl, phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, 4-F-phenyl, 4-Cl-phenyl, 4-$CH_3$-phenyl, 4-$CF_3$-phenyl, 4-$CH_3$O-phenyl, 4-$CF_3$O-phenyl, 3-F-phenyl, 3-Cl-phenyl, 3-$CH_3$-phenyl, 3-$CF_3$-phenyl, 3-$CH_3$O-phenyl, 3-$CF_3$O-phenyl, 2-F-phenyl, 2-Cl-phenyl, 2-$CH_3$-phenyl, 2-$CF_3$-phenyl, 2-$CH_3$O-phenyl, 2-$CF_3$O-phenyl, (4-F-phenyl)methyl-, (4-Cl-phenyl)methyl-, (4-$CH_3$-phenyl)methyl-, (4-$CF_3$-phenyl)methyl-, (4-$CH_3$O-phenyl)methyl-, (4-$CF_3$O-phenyl)methyl-, (3-F-phenyl)methyl-, (3-Cl-phenyl)methyl-, (3-$CH_3$-phenyl)methyl-, (3-$CF_3$-phenyl)methyl-, (3-$CH_3$O-phenyl)methyl-, (3-$CF_3$O-phenyl)methyl-, (2-F-phenyl)methyl-, (2-Cl-phenyl)methyl-, (2-$CH_3$-phenyl)methyl-, (2-$CF_3$-phenyl)methyl-, (2-$CH_3$O-phenyl)methyl-, (2-$CF_3$O-phenyl)methyl-, 2-pyridyl-, 3-pyridyl-, 4-pyridyl-, 1-piperidinyl, 1-homopiperidinyl, and 1-morpholino; and $R^{13}$, at each occurrence, is independently selected from H, F, Cl, and methoxy.

16. A compound of claim 14 wherein:

Q is —$CH_3$, —$CH_2CH_3$, —$CH_2CH_2CH_3$, —$CH(CH_3)_2$, phenyl-, 2-F-phenyl-, 2-Cl-phenyl-, 2-Br-phenyl-, 2-$NO_2$-phenyl-, 2-$CH_3$-phenyl-, 2-$CH_3CH_2$-phenyl-, 2-$CH_3$O-phenyl-, 2-$CF_3$-phenyl-, 2-$CF_3$O-phenyl-, 2-$CH_3$CONH-phenyl, or 3,5-dimethyl-isoxazol-4-yl-;

$R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$,

W is a bond;
X is a bond;
Y is a bond;
Z is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$, —CH$_2$C(CH$_3$)$_3$, —C(CH$_3$)$_2$CH$_2$CH$_3$, —CH(CH$_3$)CH(CH$_3$)$_2$, —CH$_2$CH$_2$CH$_2$CH$_2$CH$_2$CH$_3$, —CH(CH$_3$)CH$_2$CH$_2$CH$_2$CH$_3$, —CH$_2$CH(CH$_3$)CH$_2$CH$_2$CH$_3$, —CH$_2$CH$_2$CH(CH$_3$)CH$_2$CH$_3$, —CH$_2$CH$_2$CH$_2$CH(CH$_3$)$_2$, —CH$_2$CH(CH$_2$CH$_3$)$_2$, —CH$_2$CH$_2$C(CH$_3$)$_3$, —CH(CH$_2$CH$_3$)CH$_2$CH$_2$CH$_3$, —CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, cyclopropyl-, (cyclopropyl)CH$_2$—, (cyclopropyl)CH$_2$CH$_2$—, cyclobutyl-, (cyclobutyl)CH$_2$—, (cyclobutyl)CH$_2$CH$_2$—, cyclopentyl-, (cyclopentyl)CH$_2$—, (cyclopentyl)CH$_2$CH$_2$—, cyclohexyl-, (cyclohexyl)CH$_2$—, (cyclohexyl)CH$_2$CH$_2$—, phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, morpholino, N-piperidinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, morpholino CH$_2$—, (N-piperidinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, or (N-piperidinyl)CH$_2$CH$_2$—;

$R^{11}$ is selected from H, methyl, ethyl, propyl, butyl, phenyl, benzyl, phenethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, 4-F-phenyl, 4-Cl-phenyl, 4-CH$_3$-phenyl, 4-CF$_3$-phenyl, 4-CH$_3$O-phenyl, 4-CF$_3$O-phenyl, 3-F-phenyl, 3-Cl-phenyl, 3-CH$_3$-phenyl, 3-CF$_3$-phenyl, 3-CH$_3$O-phenyl, 3-CF$_3$O-phenyl, 2-F-phenyl, 2-Cl-phenyl, 2-CH$_3$-phenyl, 2-CF$_3$-phenyl, 2-CH$_3$O-phenyl, 2-CF$_3$O-phenyl, (4-F-phenyl)methyl-, (4-Cl-phenyl)methyl-, (4-CH$_3$-phenyl)methyl-, (4-CF$_3$-phenyl)methyl-, (4-CH$_3$O-phenyl)methyl-, (4-CF$_3$O-phenyl)methyl-, (3-F-phenyl)methyl-, (3-Cl-phenyl)methyl-, (3-CH$_3$-phenyl)methyl-, (3-CF$_3$-phenyl)methyl-, (3-CH$_3$O-phenyl)methyl-, (3-CF$_3$O-phenyl)methyl-, (2-F-phenyl)methyl-, (2-Cl-phenyl)methyl-, (2-CH$_3$-phenyl)methyl-, (2-CF$_3$-phenyl)methyl-, (2-CH$_3$O-phenyl)methyl-, (2-CF$_3$O-phenyl)methyl-, 2-pyridyl-, 3-pyridyl-, 4-pyridyl-, 1-piperidinyl, 1-homopiperidinyl, and 1-morpholino; and $R^{13}$, at each occurrence, is independently selected from H, F, Cl, and methoxy.

17. A pharmaceutical composition comprising a compound of claim 1 and a pharmaceutically acceptable carrier.

18. A pharmaceutical composition comprising a compound of claim 2 and a pharmaceutically acceptable carrier.

19. A pharmaceutical composition comprising a compound of claim 3 and a pharmaceutically acceptable carrier.

20. A pharmaceutical composition comprising a compound of claim 4 and a pharmaceutically acceptable carrier.

21. A pharmaceutical composition comprising a compound of claim 5 and a pharmaceutically acceptable carrier.

22. A pharmaceutical composition comprising a compound of claim 6 and a pharmaceutically acceptable carrier.

23. A pharmaceutical composition comprising a compound of claim 7 and a pharmaceutically acceptable carrier.

24. A pharmaceutical composition comprising a compound of claim 8 and a pharmaceutically acceptable carrier.

25. A pharmaceutical composition comprising a compound of claim 12 and a pharmaceutically acceptable carrier.

26. A pharmaceutical composition comprising a compound of claim 13 and a pharmaceutically acceptable carrier.

27. A pharmaceutical composition comprising a compound of claim 14 and a pharmaceutically acceptable carrier.

28. A pharmaceutical composition comprising a compound of claim 15 and a pharmaceutically acceptable carrier.

29. A pharmaceutical composition comprising a compound of claim 16 and a pharmaceutically acceptable carrier.

30. A method for the treatment of Alzheimer's Disease comprising administering to a host in need of such treatment a therapeutically effective amount of a compound of claim 1.

31. A method for the treatment of Alzheimer's Disease comprising administering to a host in need of such treatment a therapeutically effective amount of a compound of claim 2.

32. A method for the treatment of Alzheimer's Disease comprising administering to a host in need of such treatment a therapeutically effective amount of a compound of claim 3.

33. A method for the treatment of Alzheimer's Disease comprising administering to a host in need of such treatment a therapeutically effective amount of a compound of claim 4.

34. A method for the treatment of Alzheimer's Disease comprising administering to a host in need of such treatment a therapeutically effective amount of a compound of claim 5.

35. A method for the treatment of Alzheimer's Disease comprising administering to a host in need of such treatment a therapeutically effective amount of a compound of claim 6.

36. A method for the treatment of Alzheimer's Disease comprising administering to a host in need of such treatment a therapeutically effective amount of a compound of claim 7.

37. A method for the treatment of Alzheimer's Disease comprising administering to a host in need of such treatment a therapeutically effective amount of a compound of claim 8.

38. A method for the treatment of Alzheimer's Disease comprising administering to a host in need of such treatment a therapeutically effective amount of a compound of claim 12.

39. A method for the treatment of Alzheimer's Disease comprising administering to a host in need of such treatment a therapeutically effective amount of a compound of claim 13.

40. A method for the treatment of Alzheimer's Disease comprising administering to a host in need of such treatment a therapeutically effective amount of a compound of claim 14.

41. A method for the treatment of Alzheimer's Disease comprising administering to a host in need of such treatment a therapeutically effective amount of a compound of claim 15.

42. A method for the treatment of Alzheimer's Disease comprising administering to a host in need of such treatment a therapeutically effective amount of a compound of claim 16.

* * * * *